US008603201B2

(12) United States Patent
Tsuchida et al.

(10) Patent No.: US 8,603,201 B2
(45) Date of Patent: Dec. 10, 2013

(54) METHOD OF SYNTHESIZING CHEMICAL INDUSTRY RAW MATERIALS AND FUEL COMPOSITIONS

(75) Inventors: Takashi Tsuchida, Tokyo (JP); Shuji Sakuma, Tokyo (JP); Tetsuya Yoshioka, Tokyo (JP); Jun Kubo, Tokyo (JP)

(73) Assignee: Kabushiki Kaisha Sangi, Tokyo (JP)

( * ) Notice: Subject to any disclaimer, the term of this patent is extended or adjusted under 35 U.S.C. 154(b) by 608 days.

(21) Appl. No.: 12/391,254

(22) Filed: Feb. 23, 2009

(65) Prior Publication Data

US 2009/0205246 A1 Aug. 20, 2009

Related U.S. Application Data

(63) Continuation-in-part of application No. 12/198,059, filed on Aug. 25, 2008, now abandoned, which is a continuation-in-part of application No. PCT/JP2008/002295, filed on Aug. 25, 2008.

(30) Foreign Application Priority Data

Aug. 24, 2007 (JP) .................................. 2007-219064

(51) Int. Cl.
*C07C 29/34* (2006.01)
*C10L 1/18* (2006.01)

(52) U.S. Cl.
USPC ............. 44/452; 568/902; 568/903; 568/904; 568/905; 568/906

(58) Field of Classification Search
USPC ............ 44/452, 307; 568/902, 903, 904, 905, 568/906
See application file for complete search history.

(56) References Cited

U.S. PATENT DOCUMENTS

| 2,050,788 | A | 8/1936 | Fuchs et al. | |
| 2,971,033 | A | 2/1961 | Farrar | |
| 3,972,952 | A | 8/1976 | Clark | |
| 5,300,695 | A | 4/1994 | Radlowski | |
| 6,323,383 | B1 | 11/2001 | Tsuchida et al. | |
| 6,858,048 | B1 * | 2/2005 | Jimeson et al. | 44/452 |
| 2007/0255079 | A1 | 11/2007 | Tsuchida et al. | |
| 2009/0090046 | A1 * | 4/2009 | O'Connor et al. | 44/307 |

FOREIGN PATENT DOCUMENTS

| CA | 2319006 | * | 8/1999 |
| CA | 2319006 | A1 | 8/1999 |
| CA | 2589123 | A1 | 6/2006 |
| EP | 1052234 | A1 | 1/1999 |
| EP | 1 052 234 | A1 | 11/2000 |
| JP | 57-102822 | A | 6/1982 |
| JP | 58-59928 | A | 4/1983 |
| JP | 3279336 | A | 12/1991 |
| JP | 418042 | A | 1/1992 |
| JP | 5-305238 | A | 11/1993 |
| JP | 2004261751 | A | 9/2004 |
| WO | WO-99/38822 | A | 8/1999 |
| WO | WO-2006/059729 | A1 | 6/2006 |
| WO | WO-2009/028166 | A1 | 3/2009 |
| WO | WO-2009/034719 | A1 | 3/2009 |

OTHER PUBLICATIONS

Ancillotti, F. et al. (Aug. 1, 1998). "Oxygenate Fuels: Market Expansion and Catalytic Aspect of Synthesis," *Fuel Processing Technology* 57:163-194.
Anonymous. (Dec. 20, 2001). "Gasoline Blending Streams Test Plan," Submitted to the US EPA by The American Petroleum Institute Petroleum HPV Testing Group, pp. 1-38.
Anonymous. (May 2005). "Motor Fuels Understanding the Factors that Influence the Retail Price of Gasoline," *United States Government Accountability Office*, GAO-05-525SP, pp. 1-60.
Baker, B.G. et al. (1988). "Synthesis Gas to Motor Fuel via Light Alkenes," in *Methane Conversion*, Bibby, D.M. et al. eds., Elsevier Science Publishers B.V., Amsterdam, pp. 497-501.
Bhattacharyya, S.K. et al. (Mar. 12, 1962). "One-Step Catalytic Conversion of Ethanol to Butadiene in the Fixed Bed I. Single-Oxide Catalysis," *J. Appl. Chem.* pp. 97-104.
Bhattacharyya, S.K. et al. (Mar. 12, 1962). "One-Step Catalytic Conversion of Ethanol to Butadiene in the Fixed Bed II. Binary and Ternary-Oxide Catalysis," *J. Appl. Chem.* pp. 105-110.
Burk, P.L. et al. (1985). "The Rhodium-Promoted Guerbet Reaction Part 1. Higher Alcohols from Lower Alcohols," *J. of Molecular Catalysis* 33:1-14.
Corson, B.B. et al. (Feb. 1950). "Butadiene from Ethyl Alcohol Catalysis in the One-and Two-Step Processes," *Industrial and Engineering Chemistry* 42(2):359-373.
Demirbas, A. (2007, e-pub. Aug. 22, 2006). "Progress and Recent Trends in Biofuels," *Progress in Energy and Combustion Science* 33:1-18.
Hamelinck, C.N. et al. (2006, e-pub. Aug. 8, 2005). "Outlook for Advanced Biofuels," *Energy Policy* 34:3268-3283.
Knothe, G. (Sep. 2002). "Synthesis, Applications, and Characterization of Guerbet Compounds and Their Derivatives," *Lipid Technology* pp. 101-104.
Maiden, C.J. et al. (1988). "The New Zealand Gas-to-Gasoline Project," in *Methane Conversion*, Bibby, D.M. et al. eds., Elsevier Science Publishers B.V., Amsterdam, pp. 1-16.
Malça, J. et al. (Mar. 13, 2006). "Renewability and Life-Cycle Energy Efficiency of Bioethanol and Bio-Ethyl Tertiary Butyl Ether (bioETBE): Assessing the Implications of Allocation," *Energy* 31:3362-3380.

(Continued)

*Primary Examiner* — Prem C Singh
*Assistant Examiner* — Chantel Graham
(74) *Attorney, Agent, or Firm* — Hodgson Russ LLP

(57) ABSTRACT

The present invention is to provide a novel method for manufacturing various organic compounds from two or more kinds of alcohol, or one kind of alcohol having three or more carbon atoms. It is a method for synthesizing one kind of, or two or more kinds of organic compounds comprising allowing two or more kinds of alcohol or one kind of alcohol having three or more carbon atoms to contact a calcium phosphate catalyst such as hydroxyapatite, or hydrotalcite.

16 Claims, 19 Drawing Sheets

(56) References Cited

OTHER PUBLICATIONS

Meisel, S.L. et al. (Feb. 1976). "Gasoline from Methanol in One Step," *Chemtech.* pp. 86-89.

Mysov, V.M. et al. (2005). "Synthesis Gas Conversion Into Hydrocarbons (Gasoline Range) Over Bifunctional Zeolite-Containing Catalyst: Experimental Study and Mathematical Modelling," *Chemical Engineering Journal* 107:63-71.

Nagarajan, V. (Oct. 1971). "Kinetics of a Complex Reaction System-Preparation of *n*-Butanol from Ethanol in One Step," *Indian Journal of Technology* 9:380-386.

Ndou, A.S. et al. (2003). "Dimerisation of Ethanol to Butanol Over Solid-Base Catalysts," *Applied Catalysis A: General* 251:337-345.

Olson, E.S. et al. (2004). "Higher-Alcohols Biorefinery Improvement of Catalyst for Ethanol Conversion," *Applied Biochemistry and Biotechnology* 113-1 16:913-932.

Snelling, J. et al. (Jan. 21, 2003). "Synthesis of Higher Carbon Ethers from Olefins and Alcohols I. Reactions with Methanol," *Fuel Processing Technology* 83:219-234.

Ueda, W. et al. (1990). "A Low-Pressure Guerbet Reaction over Magnesium Oxide Catalyst," *J. Chem. Soc., Chem. Commun.* pp. 1558-1559.

Ueda, W. et al. (1992). "Condensation of Alcohol over Solid-Base Catalyst to Form Higher Alcohols," *Catal. Letters* 12:97-104.

Yang, C. et al. (1993). "Bimolecular Condensation of Ethanol to 1-Butanol Catalyzed by Alkali Cation Zeolites," *Journal of Catalysis* 142:37-44.

Supplementary European Search Report for EP Application No. 08790499.1 based on PCT/JP2008002295 dated Aug. 1, 2013.

\* cited by examiner (ethanol : 1-propanol = 1 : 1)

Yield of alcohol

Fig. 2
(ethanol : 1 propanol = 1 : 4)
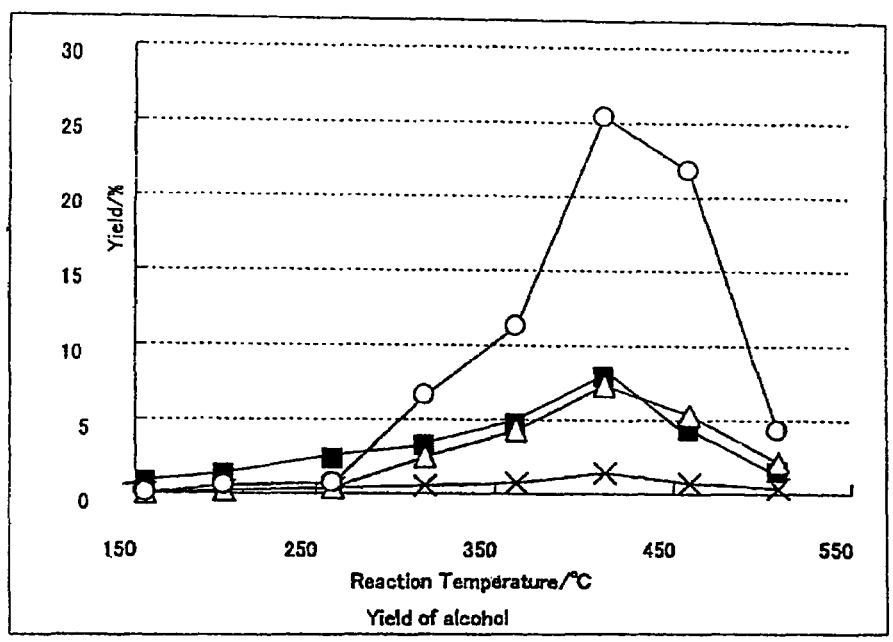
Yield of alcohol
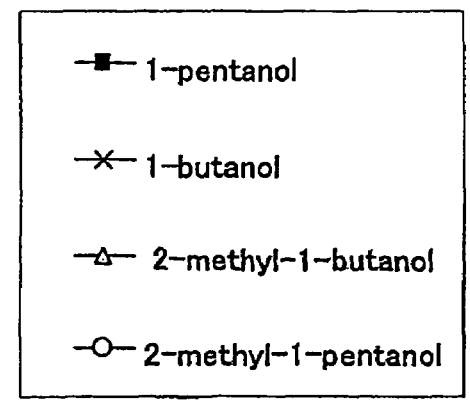

Fig. 3
(ethanol : 1-propanol = 4 : 1)
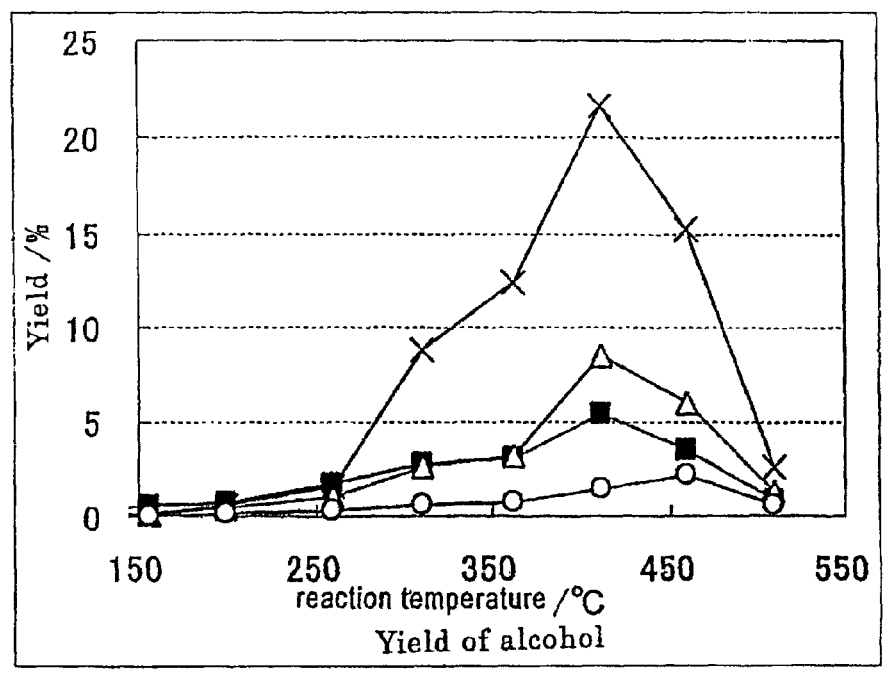
Yield of alcohol
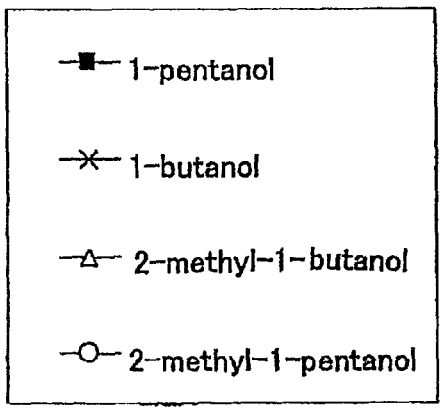
- ■ 1-pentanol
- ✕ 1-butanol
- △ 2-methyl-1-butanol
- ○ 2-methyl-1-pentanol in situ FT-IR spectra after emission
following adsorption of ethanol to HAP in situ FT-IR spectrum after 30 min emission following adsorption of ethanol to HAP

| wave number / cm$^{-1}$ | assignment | oscillation |
| --- | --- | --- |
| 2974 | -C-CH$_3$ | antisymmetric stretching oscillation |
| 2882 | -C-CH$_3$ | symmetric stretching oscillation |
| 2921 | -CH$_2$- | antisymmetric stretching oscillation |
| 2857 | -CH$_2$- | symmetric stretching oscillation |

Table - Product selectivity from mixed alcohols (methanol and ethanol) over HAP catalyst
<Conditions> 20 vol.% alcohols / He., Contact time 1.0 sec.
<Alcohols> ethanol : methanol = 1 : 1

| Reaction temp (°C) | 155 | 257 | 308 | 359 | 409 | 459 | 509 |
|---|---|---|---|---|---|---|---|
| Methanol conversion (%) | 0.0 | 1.5 | 9.9 | 28.6 | 31.6 | 75.0 | 95.1 |
| Ethanol conversion (%) | 0.1 | 3.1 | 29.0 | 32.8 | 66.8 | 98.9 | 99.9 |
| Selectivity / C-wt% | | | | | | | |
| methane | 0.0 | 0.0 | 0.0 | 0.0 | 0.1 | 0.2 | 0.7 |
| ethane | 0.0 | 0.0 | 0.0 | 0.0 | 0.1 | 0.3 | 0.6 |
| Paraffins | 0.0 | 0.0 | 0.0 | 0.0 | 0.2 | 0.4 | 1.4 |
| ethylene | 0.0 | 0.1 | 0.1 | 0.4 | 1.4 | 2.1 | 2.4 |
| propylene | 0.0 | 0.0 | 0.0 | 0.1 | 0.6 | 1.6 | 3.4 |
| butene | 0.0 | 0.0 | 0.1 | 0.6 | 0.9 | 3.0 | 6.2 |
| pentenes | 0.0 | 0.0 | 0.0 | 0.1 | 0.7 | 3.3 | 3.6 |
| hexenes | 0.0 | 0.0 | 0.0 | 0.0 | 0.3 | 1.0 | 0.9 |
| heptenes | 0.0 | 0.0 | 0.0 | 0.0 | 0.0 | 0.4 | 0.4 |
| octenes | | | | | | | |
| Olefins | 0.0 | 0.1 | 0.3 | 1.3 | 4.0 | 11.5 | 17.0 |
| Dimethylether | 0.0 | 0.2 | 0.1 | 0.3 | 0.4 | 0.4 | 0.3 |
| Ethylmethylether | 0.0 | 0.2 | 0.1 | 0.3 | 0.4 | 0.4 | 0.4 |
| Diethylether | | | | | | | |
| Methylpropylether | 0.0 | 0.0 | 0.0 | 0.0 | 0.0 | 0.0 | 0.0 |
| iso-butylmethylether | 0.0 | 0.0 | 0.0 | 0.0 | 0.0 | 0.0 | 0.0 |
| Butylethylether | | | | | | | |
| Ethers | 0.0 | 0.5 | 0.2 | 0.6 | 0.9 | 0.8 | 0.7 |
| 2-butanone | 0.0 | 0.0 | 0.0 | 0.0 | 0.1 | 0.1 | 0.1 |
| $C_7$ ketone | | | | | | | |
| Ketones | 0.0 | 0.0 | 0.0 | 0.0 | 0.1 | 0.1 | 0.1 |
| 2-propen-1-ol | 2.3 | 9.1 | 1.6 | 1.5 | 0.8 | 0.1 | 0.0 |
| 1-propanol | 43.3 | 19.3 | 22.0 | 15.9 | 13.7 | 1.1 | 0.2 |
| $C_4^=$ alcohols | 44.8 | 17.6 | 2.9 | 1.5 | 0.4 | 0.0 | 0.0 |
| 2-methyl-1-propanol | 0.0 | 0.7 | 2.9 | 2.8 | 7.6 | 12.8 | 3.7 |
| 1-butanol | 9.3 | 37.7 | 36.1 | 28.1 | 16.7 | 0.6 | 0.2 |
| $C_5^=$ alcohols | 0.0 | 0.5 | 0.2 | 0.2 | 0.1 | 0.0 | 0.0 |
| 2-methyl-1-butanol | 0.0 | 3.3 | 7.4 | 7.3 | 13.4 | 8.7 | 1.1 |
| 2,2-dimethyl-1-propanol | | | | | | | |
| 1-pentanol | 0.0 | 0.2 | 1.4 | 1.5 | 1.9 | 0.2 | 0.0 |
| $C_6$-alcohols | 0.0 | 4.0 | 6.8 | 6.4 | 7.6 | 3.7 | 0.7 |
| $C_7$-alcohols | 0.0 | 0.2 | 1.1 | 1.2 | 3.6 | 4.5 | 1.2 |
| $C_8$-alcohols | 0.0 | 0.0 | 1.5 | 1.2 | 2.4 | 2.4 | 0.8 |
| other alcohols | | | | | | | |
| Total alcohols | 99.7 | 92.5 | 84.0 | 67.6 | 68.2 | 34.1 | 7.9 |
| benzene | 0.0 | 0.0 | 0.2 | 0.4 | 1.0 | 1.3 | 1.6 |
| toluene | 0.0 | 0.0 | 0.2 | 0.3 | 0.8 | 1.7 | 2.9 |
| xylenes | 0.0 | 0.0 | 0.0 | 0.0 | 0.3 | 1.1 | 1.9 |
| propylbenzene | | | | | | | |
| butylbenzene | | | | | | | |
| other aromatics | 0.0 | 0.0 | 1.4 | 0.9 | 1.2 | 2.9 | 11.0 |
| Aromatics | 0.0 | 0.0 | 1.8 | 1.6 | 3.3 | 7.0 | 17.4 |
| Others | 0.3 | 3.2 | 10.6 | 20.8 | 9.7 | 17.2 | 20.4 |
| acetaldehyde | 0.0 | 0.0 | 1.0 | 2.0 | 1.3 | 0.0 | 0.0 |
| propanal | 0.0 | 0.0 | 0.2 | 0.4 | 0.9 | 0.5 | 0.5 |
| 2-methylpropanal | 0.0 | 0.0 | 0.0 | 0.6 | 1.1 | 6.8 | 13.3 |
| butyraldehyde | 0.0 | 0.0 | 0.3 | 0.9 | 1.2 | 0.3 | 0.5 |
| 2-methylbutanal | 0.0 | 0.0 | 0.4 | 1.5 | 1.5 | 5.5 | 5.6 |
| pentanal | 0.0 | 0.0 | 0.0 | 0.0 | 0.2 | 0.1 | 0.2 |
| other aldehydes | 0.0 | 1.9 | 0.6 | 1.2 | 2.8 | 6.9 | 5.3 |
| Aldehydes | 0.0 | 1.9 | 2.5 | 6.6 | 9.0 | 20.2 | 25.3 |
| 1,3-butadiene | 0.0 | 1.6 | 0.4 | 0.4 | 2.2 | 3.3 | 2.8 |
| pentadiene | 0.0 | 0.0 | 0.0 | 0.1 | 0.5 | 1.7 | 2.7 |
| hexadiene | 0.0 | 0.0 | 0.2 | 0.8 | 1.3 | 2.3 | 2.7 |
| heptadiene | 0.0 | 0.2 | 0.1 | 0.2 | 0.6 | 1.3 | 1.6 |
| octadiene | 0.0 | 0.0 | 0.0 | 0.0 | 0.0 | 0.2 | 0.1 |
| Dienes | 0.0 | 1.7 | 0.7 | 1.5 | 4.6 | 8.8 | 9.8 |
| Subsets | 0.0 | 3.6 | 3.2 | 8.1 | 13.6 | 28.9 | 35.1 |
| Total | 100.0 | 100.0 | 100.0 | 100.0 | 100.0 | 100.0 | 100.0 |

*FIG. 6*

Table  Product selectivity from mixed alcohols (methanol and ethanol) over HAP catalys
<Conditions> 20 vol.% alcohols / He., Contact time 1.0 sec.
<Alcohols> ethanol : methanol = 1 : 20

| Reaction temp (°C) | 155 | 256 | 307 | 358 | 407 | 457 | 505 |
|---|---|---|---|---|---|---|---|
| Methanol conversion (%) | 0.1 | (0.0) | 0.2 | 4.1 | 11.8 | 44.8 | 85.3 |
| Ethanol conversion (%) | 0.3 | 7.8 | 57.7 | 88.4 | 99.3 | 99.6 | 99.8 |
| Selectivity / C-wt% | | | | | | | |
| methane | 0.0 | 0.1 | 0.0 | 0.0 | 0.1 | 0.3 | 0.6 |
| ethane | 0.0 | 0.0 | 0.0 | 0.0 | 0.1 | 0.1 | 0.1 |
| Paraffins | 0.0 | 0.1 | 0.0 | 0.0 | 0.2 | 0.4 | 0.6 |
| ethylene | 0.2 | 0.1 | 0.1 | 0.1 | 0.1 | 0.1 | 0.1 |
| propylene | 0.0 | 0.0 | 0.0 | 0.1 | 0.2 | 0.2 | 0.3 |
| butene | 0.0 | 0.0 | 0.0 | 0.2 | 1.0 | 3.0 | 4.2 |
| pentenes | 1.2 | 0.1 | 0.0 | 0.1 | 0.3 | 0.7 | 1.5 |
| hexenes | 0.6 | 0.1 | 0.0 | 0.0 | 0.1 | 0.1 | 0.2 |
| heptenes | 0.0 | 0.0 | 0.0 | 0.0 | 0.1 | 0.1 | 0.2 |
| octenes | | | | | | | |
| Olefins | 2.0 | 0.3 | 0.1 | 0.4 | 1.8 | 4.3 | 6.5 |
| Dimethylether | 8.7 | 5.9 | 2.8 | 4.2 | 9.9 | 15.5 | 13.4 |
| Ethylmethylether | 4.2 | 0.7 | 0.2 | 0.1 | 0.1 | 0.2 | 0.3 |
| Diethylether | | | | | | | |
| Methylpropylether | 0.0 | 0.0 | 0.1 | 0.1 | 0.1 | 0.1 | 0.1 |
| iso-butylmethylether | 0.0 | 0.0 | 0.0 | 0.1 | 0.6 | 1.0 | 0.8 |
| Butylethylether | | | | | | | |
| Ethers | 12.8 | 6.6 | 3.1 | 4.4 | 10.7 | 16.8 | 14.6 |
| 2-butanone | 0.0 | 0.0 | 0.0 | 0.0 | 0.0 | 0.0 | 0.0 |
| $C_7$ ketone | 0.0 | 0.0 | 0.0 | 0.0 | 0.2 | 0.5 | 0.5 |
| Ketones | 0.0 | 0.0 | 0.0 | 0.0 | 0.2 | 0.5 | 0.5 |
| 2-propen-1-ol | 4.8 | 23.6 | 5.3 | 1.4 | 0.0 | 0.0 | 0.0 |
| 1-propanol | 1.8 | 32.7 | 36.1 | 13.3 | 0.0 | 0.0 | 0.0 |
| $C_4^=$ alcohols | 23.3 | 9.8 | 4.8 | 2.8 | 0.1 | 0.0 | 0.0 |
| 2-methyl-1-propanol | 0.0 | 10.1 | 34.2 | 57.3 | 48.4 | 8.4 | 1.0 |
| 1-butanol | 3.6 | 4.8 | 1.8 | 0.4 | 0.0 | 0.0 | 0.0 |
| $C_5^=$ alcohols | 0.0 | 0.0 | 0.1 | 0.1 | 0.2 | 0.1 | 0.0 |
| 2-methyl-1-butanol | 0.0 | 2.9 | 3.5 | 3.1 | 1.4 | 0.3 | 0.0 |
| 2,2-dimethyl-1-propanol | 0.0 | 0.0 | 0.0 | 0.0 | 0.7 | 1.1 | 0.1 |
| 1-pentanol | 0.0 | 0.7 | 0.6 | 0.2 | 0.0 | 0.0 | 0.0 |
| $C_6$-alcohols | 1.5 | 0.5 | 1.9 | 1.9 | 1.0 | 0.1 | 0.0 |
| $C_7$-alcohols | 0.0 | 0.0 | 0.4 | 1.3 | 1.4 | 0.2 | 0.0 |
| $C_8$-alcohols | | | | | | | |
| other alcohols | | | | | | | |
| Total alcohols | 35.0 | 85.1 | 88.7 | 82.0 | 53.2 | 10.2 | 1.2 |
| benzene | 0.0 | 0.0 | 0.0 | 0.0 | 0.0 | 0.1 | 0.0 |
| toluene | 0.0 | 0.0 | 0.0 | 0.1 | 0.1 | 0.1 | 0.1 |
| xylenes | | | | | | | |
| propylbenzene | | | | | | | |
| butylbenzene | | | | | | | |
| other aromatics | 9.3 | 1.5 | 1.0 | 0.7 | 0.2 | 0.0 | 0.0 |
| Aromatics | 9.3 | 1.5 | 1.0 | 0.8 | 0.4 | 0.1 | 0.1 |
| Others | 34.9 | 4.9 | 2.6 | 2.8 | 2.7 | 2.7 | 3.3 |
| acetaldehyde | | | | | | | |
| propanal | 0.0 | 0.0 | 0.3 | 0.7 | 0.0 | 0.0 | 0.0 |
| 2-methylpropanal | 0.0 | 0.0 | 0.5 | 3.9 | 11.0 | 6.7 | 2.0 |
| butyraldehyde | 0.0 | 0.0 | 0.0 | 0.0 | 0.1 | 0.0 | 0.0 |
| 2-methylbutanal | 0.0 | 0.0 | 0.1 | 0.3 | 0.6 | 0.4 | 0.2 |
| pentanal | 0.0 | 0.0 | 0.0 | 0.0 | 0.0 | 0.0 | 0.0 |
| other aldehydes | 0.0 | 0.0 | 0.0 | 0.2 | 0.9 | 1.4 | 0.4 |
| Aldehydes | 0.0 | 0.0 | 0.9 | 5.1 | 12.5 | 8.5 | 2.6 |
| 1,3-butadiene | 4.6 | 1.7 | 0.3 | 0.3 | 0.4 | 1.8 | 2.3 |
| pentadiene | 0.0 | 0.0 | 0.0 | 0.0 | 0.1 | 0.1 | 0.2 |
| hexadiene | 1.4 | 0.0 | 0.0 | 0.0 | 0.2 | 0.1 | 0.1 |
| heptadiene | 0.0 | 0.0 | 0.0 | 0.0 | 0.1 | 0.2 | 0.3 |
| octadiene | 0.0 | 0.0 | 0.0 | 0.0 | 0.0 | 0.0 | 0.0 |
| Dienes | 6.0 | 1.7 | 0.4 | 0.3 | 0.9 | 2.2 | 3.0 |
| Subsets | 6.0 | 1.7 | 1.3 | 5.5 | 13.4 | 10.7 | 5.6 |
| Total | 100.0 | 100.0 | 100.0 | 100.0 | 100.0 | 100.0 | 100.0 |
| Carbon oxide | 0.0 | 0.0 | 3.2 | 4.2 | 17.5 | 54.2 | 67.7 |

*FIG. 7*

Table  Product selectivity from mixed alcohols (ethanol and 1-propanol) over HAP catalyst
<Conditions> 20 vol.% alcohols / He., Contact time 1.0 sec.
<Alcohols> ethanol : 1-propanol = 4 : 1

| Reaction temp (°C) | 261 | 311 | 362 | 411 | 460 | 510 |
|---|---|---|---|---|---|---|
| Ethanol conversion (%) | 3.7 | 24.8 | 33.5 | 65.8 | 95.9 | 99.9 |
| 1-propanol conversion (%) | 1.6 | 19.4 | 27.4 | 56.5 | 92.4 | 99.4 |
| Selectivity / C-wt% | | | | | | |
| methane | 0.0 | 0.0 | 0.0 | 0.0 | 0.1 | 0.7 |
| ethane | 0.0 | 0.0 | 0.0 | 0.1 | 0.3 | 1.3 |
| butane | 0.0 | 0.0 | 0.0 | 0.1 | 0.1 | 0.3 |
| Paraffins | 0.0 | 0.0 | 0.0 | 0.2 | 0.6 | 2.3 |
| ethylene | 0.1 | 0.1 | 0.4 | 1.3 | 2.6 | 3.4 |
| propylene | 0.0 | 0.0 | 0.2 | 0.8 | 2.3 | 4.3 |
| butene | 0.0 | 0.0 | 0.1 | 0.5 | 1.5 | 3.2 |
| pentene | 0.0 | 0.0 | 0.1 | 0.7 | 3.2 | 4.2 |
| hexenes | 0.0 | 0.0 | 0.0 | 0.3 | 1.9 | 2.0 |
| heptenes | 0.0 | 0.0 | 0.0 | 0.2 | 1.6 | 1.5 |
| octenes | 0.0 | 0.2 | 0.1 | 0.5 | 1.3 | 1.0 |
| Olefins | 0.1 | 0.3 | 0.9 | 4.4 | 14.4 | 19.7 |
| diethylether | 0.0 | 0.0 | 0.1 | 0.2 | 0.1 | 0.1 |
| ethylpropylether | 0.0 | 0.0 | 0.1 | 0.1 | 0.1 | 0.0 |
| di-n-propylether | 0.0 | 0.0 | 0.1 | 0.1 | 0.0 | 0.0 |
| ethyl-n-butylether | 0.5 | 0.3 | 0.2 | 0.2 | 0.1 | 0.1 |
| Ethers | 0.5 | 0.4 | 0.5 | 0.6 | 0.3 | 0.2 |
| 2-butanone | 0.0 | 0.1 | 0.1 | 0.1 | 0.1 | 0.5 |
| Ketones | 0.0 | 0.1 | 0.1 | 0.1 | 0.1 | 0.5 |
| 2-methyl-1-propanol | 0.0 | 0.1 | 0.1 | 0.2 | 0.5 | 0.2 |
| $C_4^=$alcohols | 10.6 | 3.4 | 3.7 | 1.0 | 0.2 | 0.0 |
| 1-butanol | 35.3 | 37.9 | 37.3 | 25.7 | 4.9 | 0.8 |
| 2-methyl-1-butanol | 6.3 | 10.3 | 10.0 | 9.9 | 5.2 | 0.3 |
| $C_5^=$alcohols | 5.9 | 2.0 | 1.5 | 0.6 | 0.2 | 0.1 |
| 1-pentanol | 13.5 | 13.0 | 10.3 | 7.0 | 2.3 | 0.3 |
| 2-methyl-1-pentanol | 1.1 | 2.0 | 1.6 | 1.8 | 1.5 | 0.2 |
| 2-ethyl-1-butanol | 2.6 | 3.5 | 3.6 | 4.6 | 2.5 | 0.3 |
| 1-hexanol | 0.7 | 3.9 | 4.2 | 5.3 | 1.6 | 0.1 |
| $C_7$-alcohols | 1.5 | 5.0 | 4.4 | 6.1 | 4.8 | 1.3 |
| $C_8$-alcohols | 0.1 | 2.1 | 1.9 | 3.5 | 4.0 | 1.1 |
| $C_9$-alcohols | 0.0 | 1.3 | 1.0 | 1.5 | 1.6 | 0.8 |
| $C_{10}$-alcohols | 0.0 | 0.0 | 0.0 | 0.0 | 0.0 | 0.0 |
| other alcohols | 0.3 | 0.2 | 0.1 | 0.1 | 0.0 | 0.0 |
| Total alcohols | 77.8 | 84.7 | 79.8 | 67.2 | 29.4 | 5.6 |
| benzene | 0.0 | 0.1 | 0.3 | 0.9 | 2.1 | 3.9 |
| toluene | 0.0 | 0.2 | 0.3 | 0.7 | 1.9 | 4.9 |
| ethylbenzene | 0.0 | 0.0 | 0.1 | 0.3 | 1.3 | 2.9 |
| xylenes | 0.0 | 0.0 | 0.0 | 0.4 | 0.8 | 1.5 |
| propylbenzene | 0.0 | 0.2 | 0.2 | 0.3 | 1.0 | 2.6 |
| $C_{10}$-aromatics | 0.1 | 0.3 | 0.3 | 0.2 | 0.5 | 1.4 |
| Aromatics | 0.1 | 0.8 | 1.2 | 2.8 | 7.6 | 17.3 |
| Others | 4.2 | 7.3 | 6.5 | 7.6 | 19.1 | 25.7 |
| acetaldehyde | 16.1 | 3.2 | 4.1 | 2.9 | 1.6 | 0.7 |
| propanal | 0.8 | 0.7 | 1.4 | 1.3 | 1.2 | 1.1 |
| butyraldehyde | 0.0 | 0.4 | 1.0 | 2.0 | 2.4 | 1.4 |
| 2-methylbutanal | 0.0 | 0.3 | 0.8 | 1.6 | 1.9 | 1.6 |
| pentanal | 0.0 | 0.1 | 0.3 | 0.5 | 0.6 | 0.5 |
| 2-methylpentanal | 0.0 | 0.2 | 0.5 | 0.6 | 0.3 | 0.3 |
| 2-ethylbutanal | 0.0 | 0.3 | 0.9 | 1.1 | 1.1 | 1.5 |
| $C_8$-aldehydes | 0.0 | 0.6 | 0.5 | 0.9 | 1.8 | 1.1 |
| Aldehydes | 16.9 | 5.7 | 9.5 | 10.8 | 11.0 | 8.3 |
| 1,3-butadiene | 0.3 | 0.3 | 0.7 | 2.5 | 5.9 | 6.3 |
| pentadiene | 0.0 | 0.2 | 0.4 | 1.3 | 3.3 | 4.2 |
| hexadiene | 0.0 | 0.1 | 0.3 | 1.4 | 4.6 | 5.1 |
| heptadiene | 0.0 | 0.0 | 0.1 | 0.7 | 2.1 | 2.7 |
| octadiene | 0.0 | 0.0 | 0.1 | 0.3 | 1.5 | 2.0 |
| Dienes | 0.3 | 0.6 | 1.5 | 6.2 | 17.4 | 20.4 |
| Subsets | 17.3 | 6.3 | 11.0 | 17.1 | 28.4 | 28.6 |
| Total | 100.0 | 100.0 | 100.0 | 100.0 | 100.0 | 100.0 |

*FIG. 8*

Table Product selectivity from mixed alcohols (ethanol and 1-propanol) over HAP catalyst
<Conditions> 20 vol.% alcohols / He., Contact time 1.0 sec.
<Alcohols> ethanol : 1-propanol = 1 : 1

| Reaction temp (°C) | | 255 | 305 | 355 | 405 | 454 | 503 |
|---|---|---|---|---|---|---|---|
| Ethanol conversion (%) | | 2.0 | 12.1 | 29.1 | 55.9 | 93.7 | 99.8 |
| 1-propanol conversion (%) | | (0.1) | 7.9 | 20.3 | 42.9 | 86.5 | 98.3 |
| Selectivity / C-wt% | | | | | | | |
| | methane | 0.0 | 0.0 | 0.0 | 0.0 | 0.1 | 0.4 |
| | ethane | 0.0 | 0.0 | 0.0 | 0.0 | 0.2 | 0.9 |
| | butane | 0.0 | 0.0 | 0.0 | 0.0 | 0.1 | 0.2 |
| Paraffins | | 0.0 | 0.0 | 0.0 | 0.1 | 0.3 | 1.5 |
| | ethylene | 0.2 | 0.1 | 0.4 | 1.0 | 1.7 | 2.1 |
| | propylene | 0.2 | 0.1 | 0.7 | 2.3 | 5.1 | 7.0 |
| | butene | 0.0 | 0.0 | 0.1 | 0.4 | 1.5 | 2.6 |
| | pentene | 0.0 | 0.0 | 0.1 | 1.0 | 4.8 | 6.2 |
| | hexenes | 0.0 | 0.0 | 0.0 | 0.5 | 3.2 | 4.7 |
| | heptenes | 0.0 | 0.0 | 0.0 | 0.2 | 1.9 | 2.4 |
| | octenes | 2.6 | 1.3 | 0.7 | 0.7 | 2.1 | 2.0 |
| Olefins | | 2.9 | 1.5 | 2.1 | 6.2 | 20.3 | 27.0 |
| | diethylether | 0.0 | 0.0 | 0.1 | 0.0 | 0.0 | 0.0 |
| | ethylpropylether | 0.5 | 0.2 | 0.2 | 0.2 | 0.1 | 0.1 |
| | di-n-propylether | 0.0 | 0.0 | 0.1 | 0.1 | 0.1 | 0.1 |
| | ethyl-n-butylether | 2.0 | 0.7 | 0.3 | 0.2 | 0.1 | 0.1 |
| Ethers | | 2.6 | 0.9 | 0.7 | 0.6 | 0.3 | 0.3 |
| | 2-butanone | 0.0 | 0.1 | 0.1 | 0.1 | 0.1 | 0.5 |
| Ketones | | 0.0 | 0.1 | 0.1 | 0.1 | 0.1 | 0.5 |
| | 2-methyl-1-propanol | 0.0 | 0.1 | 0.1 | 0.3 | 0.7 | 0.2 |
| | $C_4$-alcohols | 9.0 | 2.2 | 1.5 | 0.8 | 0.1 | 0.0 |
| | 1-butanol | 14.6 | 18.0 | 16.3 | 11.4 | 2.6 | 1.1 |
| | 2-methyl-1-butanol | 8.5 | 16.2 | 17.7 | 15.9 | 7.5 | 0.9 |
| | $C_5$-alcohols | 16.2 | 4.8 | 2.5 | 1.0 | 0.2 | 0.0 |
| | 1-pentanol | 24.7 | 26.8 | 21.6 | 15.6 | 4.7 | 0.3 |
| | 2-methyl-1-pentanol | 5.7 | 11.6 | 12.0 | 11.4 | 7.9 | 1.5 |
| | 2-ethyl-1-butanol | 0.5 | 0.9 | 1.0 | 1.1 | 0.9 | 0.4 |
| | 1-hexanol | 0.0 | 0.7 | 1.0 | 1.4 | 0.8 | 0.1 |
| | $C_7$-alcohols | 0.6 | 3.2 | 4.1 | 5.6 | 4.8 | 0.5 |
| | $C_8$-alcohols | 0.0 | 2.0 | 2.4 | 3.3 | 3.9 | 1.5 |
| | $C_9$-alcohols | 0.0 | 0.3 | 0.5 | 1.0 | 1.5 | 0.0 |
| | $C_{10}$-alcohols | 0.0 | 0.2 | 0.4 | 0.7 | 1.2 | 0.0 |
| | other alcohols | | | | | | |
| Total alcohols | | 79.9 | 86.9 | 81.3 | 69.7 | 36.7 | 6.6 |
| | benzene | 0.0 | 0.0 | 0.1 | 0.3 | 0.5 | 0.8 |
| | toluene | 0.0 | 0.1 | 0.3 | 0.6 | 1.6 | 3.6 |
| | ethylbenzene | 0.0 | 0.0 | 0.0 | 0.0 | 0.2 | 0.4 |
| | xylenes | 0.0 | 0.0 | 0.1 | 0.2 | 0.7 | 1.8 |
| | propylbenzene | 0.0 | 0.1 | 0.1 | 0.1 | 0.3 | 0.7 |
| | $C_{10}$-aromatics | 0.0 | 0.0 | 0.1 | 0.2 | 0.4 | 1.4 |
| Aromatics | | 0.0 | 0.2 | 0.7 | 1.4 | 3.6 | 8.7 |
| Others | | 6.3 | 4.3 | 4.7 | 5.5 | 11.9 | 20.5 |
| | acetaldehyde | 3.5 | 1.8 | 2.6 | 2.3 | 1.1 | 0.5 |
| | propanal | 4.6 | 2.4 | 3.9 | 3.8 | 3.0 | 2.5 |
| | butyraldehyde | 0.0 | 0.2 | 0.4 | 0.6 | 0.8 | 0.7 |
| | 2-methylbutanal | 0.0 | 0.3 | 0.9 | 1.7 | 2.2 | 2.5 |
| | pentanal | 0.0 | 0.2 | 0.4 | 0.8 | 1.1 | 1.3 |
| | 2-methylpentanal | 0.0 | 0.0 | 0.0 | 0.2 | 1.3 | 3.6 |
| | 2-ethylbutanal | 0.0 | 0.0 | 0.0 | 0.0 | 0.1 | 0.4 |
| | $C_8$-aldehydes | 0.0 | 0.6 | 0.6 | 0.4 | 0.5 | 0.8 |
| Aldehydes | | 8.1 | 5.5 | 8.8 | 9.8 | 10.0 | 12.2 |
| | 1,3-butadiene | 0.1 | 0.2 | 0.4 | 1.3 | 2.2 | 2.4 |
| | pentadiene | 0.0 | 0.2 | 0.9 | 3.0 | 6.5 | 8.3 |
| | hexadiene | 0.0 | 0.1 | 0.3 | 1.2 | 4.1 | 6.0 |
| | heptadiene | 0.0 | 0.0 | 0.1 | 0.8 | 2.5 | 3.3 |
| | octadiene | 0.0 | 0.0 | 0.0 | 0.2 | 1.4 | 2.7 |
| Dienes | | 0.1 | 0.5 | 1.7 | 6.6 | 16.7 | 22.7 |
| Subsets | | 8.3 | 6.0 | 10.5 | 16.4 | 26.8 | 34.9 |
| Total | | 100.0 | 100.0 | 100.0 | 100.0 | 100.0 | 100.0 |

*FIG. 9*

Table Product selectivity from mixed alcohols (ethanol and 1-propanol) over HAP catalyst
<Conditions> 20 vol.% alcohols / He., Contact time 1.0 sec.
<Alcohols> ethanol : 1-propanol = 1 : 4

| Reaction temp (°C) | 261 | 311 | 362 | 411 | 460 | 510 |
|---|---|---|---|---|---|---|
| Ethanol conversion (%) | 10.5 | 32.7 | 48.5 | 82.7 | 99.0 | 99.9 |
| 1-propanol conversion (%) | 0.5 | 16.2 | 27.8 | 62.2 | 94.1 | 99.7 |
| Selectivity / C-wt% | | | | | | |
| methane | 0.0 | 0.0 | 0.0 | 0.0 | 0.1 | 0.4 |
| ethane | 0.0 | 0.0 | 0.0 | 0.1 | 0.3 | 1.2 |
| butane | 0.0 | 0.0 | 0.0 | 0.0 | 0.1 | 0.2 |
| Paraffins | 0.0 | 0.0 | 0.0 | 0.1 | 0.4 | 1.8 |
| ethylene | 0.0 | 0.0 | 0.1 | 0.2 | 0.4 | 0.8 |
| propylene | 0.1 | 0.1 | 0.6 | 1.9 | 4.3 | 7.0 |
| butene | 0.0 | 0.0 | 0.1 | 0.2 | 0.4 | 1.1 |
| pentene | 0.0 | 0.0 | 0.1 | 0.6 | 2.3 | 3.6 |
| hexenes | 0.0 | 0.0 | 0.1 | 0.8 | 4.2 | 4.7 |
| heptenes | 0.0 | 0.0 | 0.0 | 0.1 | 0.5 | 0.6 |
| octenes | 0.0 | 0.0 | 0.0 | 0.4 | 1.3 | 1.5 |
| Olefins | 0.1 | 0.1 | 1.0 | 4.2 | 13.4 | 19.4 |
| diethylether | 0.0 | 0.0 | 0.0 | 0.0 | 0.0 | 0.0 |
| ethylpropylether | 0.0 | 0.0 | 0.1 | 0.1 | 0.1 | 0.0 |
| di-n-propylether | 0.0 | 0.1 | 0.1 | 0.2 | 0.1 | 0.1 |
| ethyl-n-butylether | 1.6 | 0.4 | 0.3 | 0.2 | 0.1 | 0.1 |
| Ethers | 1.6 | 0.6 | 0.5 | 0.4 | 0.3 | 0.2 |
| 2-butanone | 0.0 | 0.1 | 0.2 | 0.1 | 0.1 | 0.3 |
| Ketones | 0.0 | 0.1 | 0.2 | 0.1 | 0.1 | 0.3 |
| 2-methyl-1-propanol | 0.1 | 0.1 | 0.2 | 0.5 | 1.0 | 0.9 |
| $C_4^=$alcohols | 0.9 | 0.2 | 0.3 | 0.1 | 0.0 | 0.0 |
| 1-butanol | 3.7 | 2.9 | 2.7 | 1.6 | 0.5 | 0.2 |
| 2-methyl-1-butanol | 8.9 | 12.9 | 13.2 | 9.9 | 3.3 | 0.3 |
| $C_5^=$alcohols | 10.1 | 2.7 | 1.7 | 0.6 | 0.2 | 0.1 |
| 1-pentanol | 21.0 | 17.5 | 15.0 | 9.7 | 1.7 | 0.0 |
| 2-methyl-1-pentanol | 24.1 | 39.4 | 38.1 | 36.2 | 18.0 | 2.7 |
| 2-ethyl-1-butanol | 0.1 | 0.3 | 0.3 | 0.4 | 0.6 | 0.5 |
| 1-hexanol | 0.0 | 0.0 | 0.0 | 0.0 | 0.0 | 0.0 |
| $C_7$-alcohols | 0.5 | 2.1 | 2.3 | 2.9 | 2.6 | 0.6 |
| $C_8$-alcohols | 1.2 | 4.4 | 4.5 | 7.2 | 6.3 | 2.8 |
| $C_9$-alcohols | 0.0 | 0.0 | 0.1 | 0.1 | 0.1 | 0.0 |
| $C_{10}$-alcohols | 0.0 | 0.0 | 0.0 | 0.0 | 0.0 | 0.0 |
| other alcohols | 7.8 | 3.2 | 2.2 | 1.0 | 0.4 | 0.1 |
| Total alcohols | 78.5 | 85.7 | 80.5 | 70.3 | 34.8 | 8.4 |
| benzene | 0.0 | 0.0 | 0.0 | 0.0 | 0.1 | 0.1 |
| toluene | 0.2 | 0.1 | 0.2 | 0.3 | 0.5 | 1.2 |
| ethylbenzene | 0.0 | 0.0 | 0.0 | 0.0 | 0.0 | 0.1 |
| xylenes | 0.0 | 0.0 | 0.1 | 0.4 | 1.1 | 2.4 |
| propylbenzene | 0.0 | 0.1 | 0.1 | 0.2 | 0.2 | 0.3 |
| $C_{10}$-aromatics | 0.0 | 0.1 | 0.1 | 0.2 | 0.6 | 1.4 |
| Aromatics | 0.2 | 0.3 | 0.6 | 1.1 | 2.4 | 5.5 |
| Others | 13.0 | 8.1 | 7.1 | 10.6 | 20.0 | 28.0 |
| acetaldehyde | 1.0 | 0.6 | 0.9 | 0.5 | 0.2 | 0.1 |
| propanal | 4.9 | 3.0 | 5.7 | 4.7 | 3.2 | 2.6 |
| butyraldehyde | 0.0 | 0.1 | 0.2 | 0.3 | 0.6 | 2.0 |
| 2-methylbutanal | 0.0 | 0.1 | 0.4 | 0.6 | 1.9 | 2.5 |
| pentanal | 0.1 | 0.2 | 0.5 | 0.9 | 1.0 | 1.8 |
| 2-methylpentanal | 0.0 | 0.1 | 0.7 | 1.6 | 10.7 | 11.9 |
| 2-ethylbutanal | 0.0 | 0.0 | 0.0 | 0.0 | 0.0 | 0.0 |
| $C_8$-aldehydes | 0.5 | 0.7 | 0.7 | 1.1 | 1.5 | 1.5 |
| Aldehydes | 6.6 | 4.8 | 9.0 | 9.6 | 19.1 | 22.4 |
| 1,3-butadiene | 0.0 | 0.0 | 0.0 | 0.1 | 0.3 | 0.5 |
| pentadiene | 0.0 | 0.1 | 0.5 | 1.1 | 2.5 | 3.5 |
| hexadiene | 0.0 | 0.1 | 0.5 | 2.0 | 5.5 | 7.7 |
| heptadiene | 0.0 | 0.0 | 0.1 | 0.3 | 0.6 | 1.1 |
| octadiene | 0.0 | 0.0 | 0.0 | 0.1 | 0.6 | 1.1 |
| Dienes | 0.0 | 0.3 | 1.1 | 3.5 | 9.5 | 13.9 |
| Subsets | 6.6 | 5.1 | 10.1 | 13.2 | 28.7 | 36.4 |
| Total | 100.0 | 100.0 | 100.0 | 100.0 | 100.0 | 100.0 |

*FIG. 10*

Table Product selectivity from mixed alcohols (ethanol, methanol and 1-propanol) over HAP catalyst
<Conditions> 20 vol.% alcohols / He., Contact time 1.0 sec.
<Alcohols> ethanol : methanol : 1-propanol = 1 : 5 : 1
<Catalyst> HAP

| Reaction temp (°C) | 257 | 308 | 358 | 409 | 458 | 507 |
|---|---|---|---|---|---|---|
| Methanol conversion (%) | 0.0 | 6.1 | 12.2 | 29.3 | 56.7 | 81.1 |
| Ethanol conversion (%) | 3.8 | 24.6 | 42.9 | 77.9 | 100.0 | 100.0 |
| 1-propanol conversion (%) | 1.1 | 19.2 | 31.0 | 68.9 | 99.9 | 99.9 |
| Selectivity / C-wt% | | | | | | |
| methane | 0.4 | 0.0 | 0.1 | 0.1 | 0.2 | 0.6 |
| ethane | 0.0 | 0.0 | 0.0 | 0.1 | 0.1 | 0.3 |
| Paraffins | 0.4 | 0.0 | 0.1 | 0.1 | 0.3 | 0.8 |
| ethylene | 0.1 | 0.1 | 0.2 | 0.4 | 0.4 | 0.5 |
| propylene | 0.2 | 0.1 | 0.2 | 0.7 | 1.2 | 2.1 |
| butene | 0.0 | 0.0 | 0.4 | 0.6 | 5.4 | 11.7 |
| pentenes | 0.0 | 0.0 | 0.1 | 0.3 | 1.3 | 2.3 |
| hexenes | 0.0 | 0.0 | 0.0 | 0.3 | 1.3 | 1.2 |
| heptenes | 0.0 | 0.0 | 0.0 | 0.1 | 0.4 | 0.6 |
| octenes | | | | | | |
| Olefins | 0.2 | 0.1 | 0.8 | 2.4 | 10.0 | 18.3 |
| Dimethylether | 1.8 | 0.5 | 0.8 | 1.0 | 1.2 | 1.5 |
| Ethylmethylether | 0.4 | 0.1 | 0.6 | 0.3 | 0.3 | 0.5 |
| Diethylether | 0.0 | 0.0 | 0.0 | 0.1 | 0.0 | 0.0 |
| Methylpropylether | 0.7 | 0.2 | 0.3 | 0.3 | 0.2 | 0.1 |
| iso-butylmethylether | 0.0 | 0.0 | 0.0 | 0.1 | 0.4 | 0.5 |
| Ethylpropylether | 0.0 | 0.0 | 0.0 | 0.0 | 0.0 | 0.0 |
| Butylethylether | | | | | | |
| Ethers | 2.9 | 0.8 | 1.7 | 1.8 | 2.2 | 2.7 |
| 2-butanone | 0.0 | 0.0 | 0.0 | 0.0 | 0.0 | 0.0 |
| 3-methyl-2-butanone | 0.0 | 0.0 | 0.0 | 0.0 | 0.0 | 0.0 |
| 3-pentanone | 0.0 | 0.0 | 0.0 | 0.0 | 0.0 | 0.0 |
| $C_6^*$ ketone | | | | | | |
| $C_6$ ketone | | | | | | |
| $C_7$ ketone | 0.0 | 0.0 | 0.0 | 0.2 | 0.4 | 1.0 |
| $C_8$ ketone | | | | | | |
| Ketones | 0.0 | 0.0 | 0.0 | 0.2 | 0.5 | 1.0 |
| 2-propen-1-ol | 7.3 | 1.8 | 1.2 | 0.6 | 0.0 | 0.0 |
| 2-propanol | | | | | | |
| $C_4^*$ alcohols | 25.5 | 6.0 | 3.1 | 0.5 | 0.0 | 0.0 |
| 2-butanol | | | | | | |
| 2-methyl-1-propanol | 26.4 | 49.1 | 49.7 | 52.8 | 30.7 | 9.9 |
| 1-butanol | 6.8 | 5.7 | 4.7 | 1.9 | 0.1 | 0.2 |
| $C_5^*$ alcohols | 5.9 | 1.5 | 1.0 | 0.3 | 0.0 | 0.0 |
| 2-methyl-1-butanol | 3.8 | 7.8 | 7.7 | 7.2 | 2.4 | 0.8 |
| 2,2-dimethyl-1-propanol | 0.0 | 0.0 | 0.0 | 0.0 | 0.4 | 0.4 |
| 1-pentanol | 8.9 | 7.1 | 4.8 | 1.4 | 0.1 | 0.1 |
| $C_6^*$-alcohols | 2.6 | 1.5 | 1.3 | 0.8 | 0.1 | 0.0 |
| 2-methyl-1-pentanol | 3.1 | 8.3 | 7.5 | 7.4 | 2.1 | 0.1 |
| 2-ethyl-1-butanol | 0.0 | 0.4 | 0.3 | 0.2 | 0.1 | 0.1 |
| 1-pentanol | 0.0 | 0.2 | 0.2 | 0.1 | 0.0 | 0.0 |
| $C_7$-alcohols | 0.0 | 1.2 | 1.4 | 2.9 | 2.3 | 0.6 |
| $C_8$-alcohols | 0.0 | 1.1 | 1.0 | 0.9 | 0.2 | 0.0 |
| other alcohols | | | | | | |
| Total alcohols | 90.4 | 91.6 | 84.0 | 77.1 | 38.6 | 12.0 |
| benzene | 0.0 | 0.0 | 0.0 | 0.0 | 0.1 | 0.1 |
| toluene | 0.0 | 0.1 | 0.1 | 0.2 | 0.2 | 0.3 |
| $C_8$-aromatics | 0.0 | 0.7 | 1.0 | 1.1 | 1.2 | 1.5 |
| $C_9$-aromatics | 0.0 | 0.4 | 0.6 | 0.7 | 0.6 | 0.9 |
| $C_{10}$-aromatics | 0.0 | 0.1 | 0.1 | 0.2 | 0.2 | 0.2 |
| other aromatics | 0.0 | 0.0 | 0.1 | 0.1 | 0.2 | 0.3 |
| Aromatics | 0.0 | 1.2 | 2.0 | 2.3 | 2.4 | 3.2 |
| Others | 0.0 | 1.4 | 2.2 | 3.0 | 6.1 | 6.3 |
| acetaldehyde | 0.0 | 0.0 | 0.0 | 0.0 | 0.1 | 0.1 |
| propanal | 4.4 | 1.5 | 3.5 | 1.9 | 0.0 | 0.0 |
| 2-methylpropanal | 1.1 | 0.5 | 2.0 | 5.8 | 24.6 | 25.0 |
| butyraldehyde | 0.0 | 0.0 | 0.1 | 0.2 | 0.0 | 0.0 |
| 2-methylbutanal | 0.0 | 0.0 | 0.1 | 0.4 | 3.2 | 3.3 |
| pentanal | 0.0 | 0.1 | 0.2 | 0.2 | 0.0 | 0.0 |
| 2-methylpentanal | 0.0 | 0.1 | 0.4 | 0.9 | 2.0 | 0.6 |
| other aldehydes | 0.0 | 1.0 | 1.0 | 0.9 | 0.5 | 1.0 |
| Aldehydes | 5.5 | 3.2 | 7.3 | 10.3 | 30.4 | 30.1 |
| 1,3-butadiene | 0.6 | 0.3 | 0.3 | 0.7 | 2.3 | 5.2 |
| pentadiene | 0.0 | 0.0 | 0.3 | 0.6 | 0.7 | 1.0 |
| hexadiene | 0.0 | 0.1 | 0.2 | 0.5 | 0.9 | 1.0 |
| heptadiene | 0.0 | 0.0 | 0.0 | 0.2 | 0.9 | 1.1 |
| octadiene | | | | | | |
| Dienes | 0.6 | 0.3 | 0.8 | 2.0 | 4.8 | 8.3 |
| Subsets | 6.1 | 3.6 | 8.1 | 12.3 | 35.3 | 38.5 |
| Total | 100.0 | 98.7 | 98.8 | 99.2 | 95.5 | 82.9 |
| Carbon oxide | 0.0 | 1.3 | 1.2 | 0.8 | 4.5 | 17.1 |

*FIG. 11*

Table Product selectivity from mixed alcohols (ethanol, methanol and 1-propanol) over MgO catalyst
<Conditions> 20 vol.% alcohols / He., Contact time 1.0 sec.
<Alcohols> ethanol : methanol : 1-propanol = 1 : 5 : 1
<Catalyst> MgO

| Reaction temp (°C) | 257 | 307 | 357 | 408 | 457 | 506 |
|---|---|---|---|---|---|---|
| Methanol conversion (%) | 0.8 | 1.1 | 8.5 | 24.5 | 55.6 | 72.4 |
| Ethanol conversion (%) | 0.0 | 7.1 | 23.5 | 57.2 | 92.2 | 96.4 |
| 1-propanol conversion (%) | 0.1 | 4.8 | 20.0 | 52.4 | 84.2 | 92.5 |
| Selectivity / C-wt% | | | | | | |
| methane | 0.3 | 0.1 | 0.0 | 0.0 | 0.1 | 0.2 |
| ethane | 0.0 | 0.0 | 0.0 | 0.0 | 0.1 | 0.1 |
| Paraffins | 0.3 | 0.1 | 0.0 | 0.1 | 0.2 | 0.4 |
| ethylene | 0.4 | 1.1 | 0.8 | 0.9 | 1.6 | 2.5 |
| propylene | 0.2 | 0.2 | 0.1 | 0.1 | 0.5 | 1.3 |
| butene | 0.0 | 0.0 | 0.0 | 0.3 | 0.3 | 0.5 |
| pentenes | 0.0 | 0.0 | 0.0 | 0.0 | 0.2 | 0.4 |
| hexenes | 0.0 | 0.0 | 0.2 | 0.1 | 0.1 | 0.2 |
| heptenes | 0.0 | 0.0 | 0.0 | 0.0 | 0.0 | 0.0 |
| octenes | | | | | | |
| Olefins | 0.6 | 1.3 | 1.1 | 1.3 | 2.7 | 4.9 |
| Dimethylether | 0.5 | 0.1 | 0.0 | 0.0 | 0.0 | 0.0 |
| Ethylmethylether | 0.0 | 0.0 | 0.0 | 0.1 | 0.1 | 0.0 |
| Diethylether | | | | | | |
| Methylpropylether | 0.0 | 0.0 | 0.0 | 0.0 | 0.1 | 0.1 |
| iso-butylmethylether | | | | | | |
| Ethylpropylether | 0.0 | 0.0 | 0.0 | 0.0 | 0.0 | 0.0 |
| Butylethylether | | | | | | |
| Ethers | 0.5 | 0.1 | 0.0 | 0.1 | 0.2 | 0.1 |
| 2-butanone | 0.0 | 0.4 | 0.6 | 0.4 | 0.2 | 0.1 |
| 3-methyl-2-butanone | 0.0 | 0.0 | 0.1 | 0.2 | 0.2 | 0.3 |
| 3-pentanone | 0.0 | 0.2 | 0.3 | 0.4 | 0.3 | 0.2 |
| $C_6^+$ ketone | 0.0 | 0.0 | 0.0 | 0.0 | 0.2 | 0.2 |
| $C_6$ ketone | 0.0 | 0.0 | 0.2 | 0.3 | 0.3 | 0.5 |
| $C_7$ ketone | 0.0 | 0.0 | 0.0 | 0.0 | 0.1 | 0.3 |
| $C_8$ ketone | 0.0 | 0.0 | 0.1 | 0.0 | 0.1 | 0.2 |
| Ketones | 0.0 | 0.6 | 1.4 | 1.3 | 1.4 | 1.8 |
| 2-propen-1-ol | 6.9 | 1.1 | 1.0 | 0.6 | 0.1 | 0.0 |
| 2-propanol | 0.7 | 0.6 | 0.3 | 0.1 | 0.0 | 0.0 |
| $C_4^+$ alcohols | 15.7 | 3.5 | 3.7 | 2.9 | 0.3 | 0.1 |
| 2-butanol | 0.0 | 1.8 | 0.9 | 0.2 | 0.1 | 0.0 |
| 2-methyl-1-propanol | 23.0 | 46.6 | 49.3 | 47.0 | 41.9 | 26.8 |
| 1-butanol | 6.5 | 3.9 | 2.6 | 1.0 | 0.2 | 0.1 |
| $C_5^+$ alcohols | 4.3 | 1.6 | 1.1 | 0.6 | 0.0 | 0.0 |
| 2-methyl-1-butanol | 0.6 | 3.3 | 4.1 | 3.6 | 2.6 | 1.4 |
| 2,2-dimethyl-1-propanol | 0.0 | 0.0 | 0.1 | 0.1 | 0.0 | 0.0 |
| 1-pentanol | 4.9 | 3.9 | 3.2 | 1.2 | 0.4 | 0.2 |
| $C_6^+$-alcohols | 0.7 | 0.7 | 1.3 | 1.1 | 0.4 | 0.0 |
| 2-methyl-1-pentanol | 0.8 | 2.1 | 3.4 | 3.5 | 2.8 | 1.3 |
| 2-ethyl-1-butanol | 0.0 | 0.0 | 0.1 | 0.1 | 0.1 | 0.0 |
| 1-hexanol | 0.0 | 0.0 | 0.0 | 0.0 | 0.0 | 0.0 |
| $C_7$-alcohols | 0.0 | 0.0 | 0.2 | 0.6 | 1.1 | 0.7 |
| $C_8$-alcohols | | | | | | |
| other alcohols | 0.5 | 0.6 | 0.4 | 0.2 | 0.1 | 0.0 |
| Total alcohols | 64.7 | 69.6 | 71.7 | 62.9 | 50.1 | 30.6 |
| benzene | 0.0 | 0.0 | 0.0 | 0.0 | 0.1 | 0.1 |
| toluene | 0.0 | 0.0 | 0.1 | 0.2 | 0.3 | 0.2 |
| $C_8$-aromatics | 0.0 | 1.0 | 0.4 | 0.6 | 0.7 | 0.5 |
| $C_9$-aromatics | 0.0 | 0.9 | 0.6 | 0.7 | 0.7 | 0.5 |
| $C_{10}$-aromatics | 0.0 | 0.2 | 0.0 | 0.1 | 0.1 | 0.1 |
| other aromatics | 0.0 | 0.0 | 0.0 | 0.0 | 0.0 | 0.0 |
| Aromatics | 0.0 | 2.2 | 1.1 | 1.6 | 1.9 | 1.3 |
| Others | 0.0 | 0.1 | 1.3 | 2.3 | 2.6 | 2.1 |
| acetaldehyde | 15.4 | 10.5 | 6.6 | 5.6 | 1.3 | 0.9 |
| propanal | 12.3 | 7.1 | 5.2 | 5.3 | 2.1 | 1.7 |
| 2-methylpropanal | 0.0 | 0.5 | 1.6 | 6.7 | 12.4 | 15.4 |
| butyraldehyde | 0.0 | 0.0 | 0.1 | 0.2 | 0.1 | 0.1 |
| 2-methylbutanal | 0.0 | 0.0 | 0.3 | 0.6 | 1.0 | 0.7 |
| pentanal | 0.0 | 0.0 | 0.0 | 0.0 | 0.0 | 0.0 |
| 2-methylpentanal | 0.0 | 0.4 | 0.1 | 0.4 | 0.7 | 0.7 |
| other aldehydes | 0.0 | 0.0 | 1.2 | 1.4 | 1.2 | 1.3 |
| Aldehydes | 27.6 | 18.5 | 15.0 | 20.2 | 18.9 | 20.8 |
| 1,3-butadiene | 0.0 | 1.6 | 0.6 | 0.3 | 0.4 | 0.4 |
| pentadiene | 0.4 | 0.5 | 0.4 | 0.4 | 0.7 | 0.7 |
| hexadiene | 0.0 | 0.0 | 0.2 | 0.3 | 0.8 | 1.3 |
| heptadiene | | | | | | |
| octadiene | 0.0 | 0.0 | 0.0 | 0.0 | 0.1 | 0.3 |
| Dienes | 0.4 | 2.2 | 1.2 | 1.0 | 2.1 | 2.6 |
| Subsets | 28.0 | 20.7 | 16.2 | 21.2 | 21.0 | 23.5 |
| Total | 94.1 | 94.5 | 92.9 | 90.8 | 80.1 | 64.7 |
| Carbon oxide | 5.9 | 5.5 | 7.1 | 9.2 | 19.9 | 35.3 |

*FIG. 12*

Table Product selectivity from mixed alcohols (ethanol, methanol and 1-butanol) over HAP catalyst
<Conditions> 20 vol.% alcohols / He., Contact time 1.0 sec
<Alcohols> ethanol : methanol : 1-butanol = 1 : 6 :
<Catalyst> HAP

| Reaction temp (°C) | 257 | 308 | 358 | 409 | 458 | 508 |
|---|---|---|---|---|---|---|
| Methanol conversion (%) | 0.8 | 12.3 | 15.3 | 33.8 | 52.6 | 84.4 |
| Ethanol conversion (%) | 4.8 | 35.4 | 51.7 | 88.5 | 100.0 | 100.0 |
| 1-butanol conversion (%) | 1.7 | 43.0 | 51.6 | 90.6 | 99.7 | 100.0 |
| Selectivity / C-wt% | | | | | | |
| methane | 0.2 | 0.0 | 0.0 | 0.0 | 0.2 | 0.9 |
| ethane | 0.0 | 0.0 | 0.0 | 0.1 | 0.2 | 0.6 |
| Paraffins | 0.2 | 0.0 | 0.0 | 0.1 | 0.4 | 1.5 |
| ethylene | 0.0 | 0.0 | 0.1 | 0.2 | 0.4 | 0.7 |
| propylene | 0.0 | 0.0 | 0.0 | 0.2 | 0.5 | 1.5 |
| butene | 0.0 | 0.0 | 0.0 | 0.4 | 3.1 | 7.6 |
| pentenes | 0.0 | 0.0 | 0.2 | 1.2 | 7.7 | 10.9 |
| hexenes | 0.0 | 0.0 | 0.1 | 0.4 | 0.7 | 1.1 |
| heptenes | 0.0 | 0.0 | 0.1 | 0.2 | 0.6 | 0.4 |
| octenes | 0.0 | 0.0 | 0.0 | 0.1 | 0.5 | 0.4 |
| Olefins | 0.0 | 0.0 | 0.5 | 2.7 | 13.6 | 22.6 |
| Dimethylether | 1.2 | 0.2 | 0.6 | 0.8 | 1.4 | 1.5 |
| Ethylmethylether | 0.2 | 0.0 | 0.1 | 0.3 | 0.2 | 0.3 |
| Diethylether | | | | | | |
| Methylpropylether | 0.0 | 0.0 | 0.1 | 0.1 | 0.5 | 0.9 |
| iso-butylmethylether | 0.0 | 0.0 | 0.0 | 0.0 | 0.2 | 0.4 |
| Ethylpropylether | 0.0 | 0.0 | 0.0 | 0.0 | 0.0 | 0.0 |
| n-butylmethylether | 0.8 | 0.1 | 0.2 | 0.3 | 0.3 | 0.2 |
| Butylethylether | 0.0 | 0.0 | 0.0 | 0.1 | 0.4 | 0.3 |
| Ethers | 2.1 | 0.4 | 1.0 | 1.6 | 3.0 | 3.5 |
| 2-butanone | 0.0 | 0.0 | 0.0 | 0.0 | 0.2 | 0.2 |
| 3-methyl-2-butanone | 0.0 | 0.0 | 0.0 | 0.0 | 0.0 | 0.0 |
| 3-pentanone | 0.0 | 0.0 | 0.1 | 0.1 | 0.0 | 0.0 |
| $C_6^=$ ketone | 0.0 | 0.0 | 0.0 | 0.0 | 0.0 | 0.0 |
| $C_6$ ketone | 0.0 | 0.0 | 0.0 | 0.1 | 0.1 | 0.3 |
| $C_7$ ketone | 0.0 | 0.0 | 0.0 | 0.0 | 0.2 | 0.5 |
| $C_8$ ketone | | | | | | |
| Ketones | 0.0 | 0.0 | 0.1 | 0.2 | 0.6 | 1.1 |
| 2-propen-1-ol | 6.5 | 0.8 | 0.8 | 0.3 | 0.0 | 0.0 |
| 2-propanol | | | | | | |
| 1-propanol | 15.3 | 10.1 | 10.2 | 3.7 | 0.0 | 0.0 |
| $C_4^=$ alcohols | 0.5 | 0.4 | 0.3 | 0.2 | 0.0 | 0.0 |
| 2-butanol | | | | | | |
| 2-methyl-1-propanol | 1.6 | 0.4 | 6.4 | 14.4 | 12.7 | 4.6 |
| $C_5^=$ alcohols | 14.6 | 2.4 | 1.7 | 0.2 | 0.1 | 0.0 |
| 2-methyl-1-butanol | 31.6 | 54.9 | 46.7 | 43.0 | 17.2 | 2.7 |
| 2,2-dimethyl-1-propanol | | | | | | |
| 2-pentanol | | | | | | |
| 1-pentanol | 0.0 | 0.5 | 0.4 | 0.2 | 0.1 | 0.0 |
| $C_6^=$-alcohols | 4.2 | 0.5 | 0.6 | 0.2 | 0.2 | 0.2 |
| 2-methyl-1-pentanol | 0.0 | 0.4 | 0.6 | 1.1 | 0.8 | 0.5 |
| 2-ethyl-1-butanol | 1.6 | 3.7 | 2.9 | 1.6 | 0.3 | 0.1 |
| 2,2-dimethyl-1-butanol | 0.0 | 0.1 | 0.1 | 0.2 | 0.3 | 0.1 |
| 1-hexanol | 6.3 | 4.2 | 2.6 | 0.2 | 0.0 | 0.0 |
| $C_7$-alcohols | 1.5 | 6.7 | 6.1 | 5.1 | 2.1 | 0.3 |
| 2-ethyl-1-hexanol | 1.7 | 3.8 | 2.7 | 1.4 | 0.2 | 0.0 |
| other $C_8$-alcohols | 0.6 | 0.9 | 1.1 | 1.7 | 0.6 | 0.0 |
| other alcohols | | | | | | |
| Total alcohols | 86.0 | 89.6 | 83.2 | 73.3 | 34.8 | 8.6 |
| benzene | 0.0 | 0.0 | 0.0 | 0.1 | 0.3 | 0.2 |
| toluene | 0.0 | 0.0 | 0.1 | 0.2 | 0.4 | 0.5 |
| $C_8$-aromatics | 0.0 | 0.0 | 0.1 | 0.4 | 0.9 | 1.9 |
| $C_9$-aromatics | 0.0 | 0.0 | 0.0 | 0.2 | 0.4 | 0.9 |
| $C_{10}$-aromatics | 0.0 | 0.0 | 0.0 | 0.1 | 0.1 | 0.3 |
| other aromatics | 0.0 | 0.0 | 0.0 | 0.0 | 0.1 | 0.4 |
| Aromatics | 0.0 | 0.0 | 0.2 | 1.0 | 2.1 | 4.1 |
| Others | 0.7 | 6.1 | 4.9 | 4.3 | 4.9 | 8.7 |
| acetaldehyde | 0.0 | 0.0 | 0.0 | 0.0 | 0.0 | 0.0 |
| propanal | 1.2 | 0.1 | 0.5 | 0.5 | 0.0 | 0.1 |
| 2-methylpropanal | 0.0 | 0.2 | 0.8 | 2.4 | 10.8 | 12.0 |
| butyraldehyde | 2.6 | 0.9 | 2.6 | 0.8 | 0.1 | 0.0 |
| 2-methylbutanal | 0.0 | 0.9 | 2.7 | 7.9 | 18.4 | 8.7 |
| pentanal | | | | | | |
| 2-methylpentanal | 0.0 | 0.0 | 0.1 | 0.3 | 0.8 | 0.7 |
| 2-ethylbutanal | 0.0 | 0.1 | 0.3 | 0.4 | 0.4 | 0.1 |
| other aldehydes | 5.1 | 0.3 | 0.9 | 1.2 | 1.5 | 0.8 |
| Aldehydes | 8.9 | 2.5 | 7.8 | 13.5 | 32.0 | 22.4 |
| 1,3-butadiene | 0.0 | 0.2 | 0.5 | 0.8 | 1.0 | 1.6 |
| pentadiene | 0.0 | 0.0 | 0.1 | 0.2 | 0.8 | 2.4 |
| hexadiene | 0.0 | 0.2 | 0.3 | 0.5 | 0.8 | 1.3 |
| heptadiene | 0.0 | 0.0 | 0.1 | 0.4 | 1.0 | 1.0 |
| octadiene | 0.0 | 0.0 | 0.0 | 0.0 | 0.0 | 0.0 |
| Dienes | 0.0 | 0.4 | 0.9 | 1.9 | 3.5 | 6.4 |
| Subsets | 8.9 | 3.0 | 8.7 | 15.5 | 35.5 | 28.8 |
| Total | 97.9 | 99.1 | 98.7 | 98.7 | 94.8 | 78.9 |
| Carbon oxide | 2.1 | 0.9 | 1.3 | 1.3 | 5.2 | 21.1 |

FIG. 13

Table Product selectivity from mixed alcohols (ethanol, methanol and 1-butanol) over MgO catalyst
<Conditions> 20 vol.% alcohols / He., Contact time 1.0 sec
<Alcohols> ethanol : methanol : 1-butanol = 1 : 6 :
<Catalyst> MgO

| Reaction temp (°C) | 260 | 310 | 361 | 411 | 461 | 510 |
|---|---|---|---|---|---|---|
| Methanol conversion (%) | 0.7 | 1.3 | 11.7 | 25.8 | 54.3 | 71.4 |
| Ethanol conversion (%) | 1.3 | 7.1 | 33.0 | 62.2 | 91.4 | 97.3 |
| 1-butanol conversion (%) | 0.0 | 8.6 | 38.3 | 69.5 | 93.7 | 97.4 |
| Selectivity / C-wt% | | | | | | |
| methane | 0.2 | 0.0 | 0.0 | 0.0 | 0.1 | 0.4 |
| ethane | 0.0 | 0.0 | 0.0 | 0.1 | 0.2 | 0.3 |
| Paraffins | 0.2 | 0.0 | 0.0 | 0.1 | 0.3 | 0.8 |
| ethylene | 0.5 | 0.7 | 0.6 | 0.8 | 1.3 | 2.6 |
| propylene | 0.0 | 0.0 | 0.0 | 0.1 | 0.2 | 0.8 |
| butene | 0.0 | 0.0 | 0.0 | 0.5 | 1.0 | 2.4 |
| pentenes | 0.0 | 0.0 | 0.0 | 0.0 | 0.2 | 0.5 |
| hexenes | 0.0 | 0.1 | 0.1 | 0.1 | 0.1 | 0.2 |
| heptenes | | | | | | |
| octenes | 0.0 | 0.0 | 0.0 | 0.0 | 0.1 | 0.1 |
| Olefins | 0.5 | 0.8 | 0.7 | 1.5 | 2.9 | 6.6 |
| Dimethylether | 0.3 | 0.0 | 0.0 | 0.0 | 0.0 | 0.0 |
| Ethylmethylether | 0.0 | 0.0 | 0.0 | 0.2 | 0.1 | 0.2 |
| Diethylether | 0.0 | 0.0 | 0.0 | 0.0 | 0.1 | 0.1 |
| Methylpropylether | | | | | | |
| iso-butylmethylether | | | | | | |
| Ethylpropylether | 0.0 | 0.0 | 0.0 | 0.0 | 0.0 | 0.0 |
| n-butylmethylether | 0.0 | 0.1 | 0.0 | 0.0 | 0.0 | 0.0 |
| Butylethylether | 0.0 | 0.0 | 0.1 | 0.1 | 0.1 | 0.0 |
| Ethers | 0.3 | 0.1 | 0.1 | 0.4 | 0.3 | 0.4 |
| 2-butanone | | | | | | |
| 3-methyl-2-butanone | 0.0 | 0.0 | 0.0 | 0.0 | 0.1 | 0.2 |
| 3-pentanone | 0.0 | 3.6 | 0.7 | 0.3 | 0.1 | 0.1 |
| $C_5^*$ ketone | | | | | | |
| $C_6$ ketone | 0.0 | 0.0 | 0.0 | 0.0 | 0.0 | 0.1 |
| $C_7$ ketone | | | | | | |
| $C_8$ ketone | | | | | | |
| Ketones | 0.0 | 3.6 | 0.7 | 0.4 | 0.3 | 0.4 |
| 2-propen-1-ol | 4.9 | 1.3 | 0.7 | 0.5 | 0.1 | 0.0 |
| 2-propanol | 0.0 | 0.3 | 0.1 | 0.0 | 0.0 | 0.0 |
| 1-propanol | 22.7 | 15.9 | 13.0 | 8.7 | 3.2 | 1.2 |
| $C_4$ alcohols | 0.0 | 0.1 | 0.3 | 0.7 | 0.2 | 0.1 |
| 2-butanol | 0.0 | 0.0 | 0.1 | 0.0 | 0.0 | 0.0 |
| 2-methyl-1-propanol | 2.6 | 0.9 | 3.4 | 6.9 | 12.6 | 9.7 |
| $C_5$ alcohols | 10.0 | 3.0 | 2.9 | 2.3 | 0.6 | 0.4 |
| 2-methyl-1-butanol | 28.9 | 44.6 | 47.8 | 39.0 | 28.5 | 16.2 |
| 2,2-dimethyl-1-propanol | | | | | | |
| 2-pentanol | 1.1 | 1.4 | 0.4 | 0.1 | 0.0 | 0.0 |
| 1-pentanol | 0.0 | 0.2 | 0.2 | 0.2 | 0.1 | 0.0 |
| $C_6^*$-alcohols | 3.1 | 1.5 | 0.7 | 0.5 | 0.1 | 0.0 |
| 2-methyl-1-pentanol | 0.0 | 0.0 | 0.2 | 0.4 | 0.6 | 0.4 |
| 2-ethyl-1-butanol | 0.6 | 1.5 | 1.6 | 1.0 | 0.6 | 0.3 |
| 2,2-dimethyl-1-butanol | | | | | | |
| 1-hexanol | 5.2 | 4.6 | 2.1 | 0.9 | 0.1 | 0.0 |
| $C_7$-alcohols | 0.8 | 1.1 | 2.7 | 2.4 | 1.9 | 1.0 |
| 2-ethyl-1-hexanol | 1.4 | 1.3 | 1.6 | 0.9 | 0.1 | 0.0 |
| other $C_8$-alcohols | 0.6 | 0.2 | 0.3 | 0.4 | 0.5 | 0.2 |
| other alcohols | | | | | | |
| Total alcohols | 81.9 | 77.9 | 78.2 | 64.8 | 49.2 | 29.6 |
| benzene | 0.0 | 0.0 | 0.0 | 0.0 | 0.1 | 0.1 |
| toluene | 0.0 | 0.0 | 0.1 | 0.2 | 0.4 | 0.6 |
| $C_8$-aromatics | 0.0 | 0.0 | 0.3 | 0.6 | 0.7 | 0.9 |
| $C_9$-aromatics | 0.0 | 0.1 | 0.1 | 0.1 | 0.3 | 0.4 |
| $C_{10}$-aromatics | 0.0 | 0.0 | 0.0 | 0.0 | 0.1 | 0.1 |
| other aromatics | 0.0 | 0.0 | 0.3 | 0.2 | 0.2 | 0.1 |
| Aromatics | 0.0 | 0.1 | 0.8 | 1.3 | 1.7 | 2.3 |
| Others | 1.1 | 2.5 | 2.6 | 3.2 | 3.4 | 3.7 |
| acetaldehyde | 3.7 | 2.2 | 1.6 | 1.7 | 0.6 | 0.3 |
| propanal | 0.0 | 0.2 | 0.5 | 1.3 | 1.1 | 0.8 |
| 2-methylpropanal | 0.0 | 0.0 | 0.6 | 1.7 | 4.5 | 6.4 |
| butyraldehyde | 8.7 | 6.2 | 4.0 | 4.1 | 1.2 | 0.7 |
| 2-methylbutanal | 0.0 | 0.0 | 1.8 | 6.9 | 11.4 | 12.5 |
| pentanal | | | | | | |
| 2-methylpentanal | 0.0 | 0.0 | 0.0 | 0.0 | 0.0 | 0.0 |
| 2-ethylbutanal | 0.0 | 0.0 | 0.3 | 0.5 | 0.5 | 0.5 |
| other aldehydes | 0.0 | 0.4 | 1.2 | 3.1 | 1.5 | 1.5 |
| Aldehydes | 12.4 | 9.1 | 10.0 | 19.4 | 21.0 | 22.6 |
| 1,3-butadiene | 0.0 | 0.1 | 0.7 | 0.5 | 0.4 | 0.7 |
| pentadiene | 0.0 | 0.1 | 0.1 | 0.2 | 0.4 | 0.9 |
| hexadiene | 0.0 | 2.3 | 0.7 | 0.5 | 0.8 | 1.1 |
| heptadiene | 0.0 | 0.0 | 0.0 | 0.0 | 0.0 | 0.0 |
| octadiene | | | | | | |
| Dienes | 0.0 | 2.4 | 1.6 | 1.2 | 1.6 | 2.8 |
| Subsets | 12.4 | 11.5 | 11.6 | 20.6 | 22.6 | 25.4 |
| Total | 96.4 | 96.4 | 94.8 | 92.2 | 80.7 | 69.1 |
| Carbon oxide | 3.6 | 3.6 | 5.2 | 7.8 | 19.3 | 30.9 |

FIG. 14

Table  Ratio of C5 normal alcohol within C5-saturated alcohols over catalysts
* n = normal alcohols, b = branched alcohols, normal ratio = n / (n+b)

Combination of alcohols: (Ethanol : 1-Propanol = 1 : 1 )

Catalyst 1: HAP

| Reaction temperature /°C | 100 | 150 | 200 | 250 | 300 | 350 | 400 | 450 | 500 |
|---|---|---|---|---|---|---|---|---|---|
| Normal ratio /% | - | 82.6 | 78.2 | 74.3 | 62.4 | 54.9 | 49.6 | 38.7 | 27.2 |
| Yield of normal cross Guerbet alcohols /% | 0.0 | 0.8 | 1.1 | 1.4 | 2.5 | 5.2 | 8.4 | 6.2 | 1.0 |

Catalyst 2: Hydrotalcite

| Reaction temperature /°C | 100 | 150 | 200 | 250 | 300 | 350 | 400 | 450 | 500 |
|---|---|---|---|---|---|---|---|---|---|
| Normal ratio /% | - | 83.4 | 79.8 | 77.5 | 77.0 | 74.4 | 62.3 | 47.0 | 22.5 |
| Yield of normal cross Guerbet alcohols /% | 0.0 | 0.1 | 0.3 | 0.6 | 1.0 | 2.3 | 4.1 | 3.6 | 0.9 |

Catalyst 3: MgO

| Reaction temperature /°C | 100 | 150 | 200 | 250 | 300 | 350 | 400 | 450 | 500 |
|---|---|---|---|---|---|---|---|---|---|
| Normal ratio /% | - | - | - | 83.0 | 57.5 | 52.0 | 47.0 | 39.6 | 30.7 |
| Yield of normal cross Guerbet alcohols /% | 0.0 | 0.0 | 0.0 | 0.0 | 0.2 | 0.9 | 2.1 | 2.5 | 1.8 |

Catalyst 4: CaF$_2$

| Reaction temperature /°C | 100 | 150 | 200 | 250 | 300 | 350 | 400 | 450 | 500 |
|---|---|---|---|---|---|---|---|---|---|
| Normal ratio /% | - | - | - | - | - | 92.0 | 84.6 | 82.1 | 78.8 |
| Yield of normal cross Guerbet alcohols /% | 0.0 | 0.0 | 0.0 | 0.0 | 0.0 | 0.6 | 1.2 | 0.5 | 1.1 |

Catalyst 5: CaSiO$_3$

| Reaction temperature /°C | 100 | 150 | 200 | 250 | 300 | 350 | 400 | 450 | 500 |
|---|---|---|---|---|---|---|---|---|---|
| Normal ratio /% | - | - | - | - | - | 83.8 | 83.0 | 83.1 | 75.5 |
| Yield of normal cross Guerbet alcohols /% | 0.0 | 0.0 | 0.0 | 0.0 | 0.0 | 0.1 | 0.6 | 1.1 | 1.6 |

Combination of alcohols: (Ethanol : 1-Propanol = 1 : 4 )

Catalyst 1: HAP

| Reaction temperature /°C | 100 | 150 | 200 | 250 | 300 | 350 | 400 | 450 | 500 |
|---|---|---|---|---|---|---|---|---|---|
| Normal ratio /% | - | 78.1 | 74.5 | 70.3 | 57.6 | 53.2 | 49.6 | 33.5 | 12.0 |
| Yield of normal cross Guerbet alcohols /% | 0.0 | 0.8 | 1.2 | 2.3 | 3.2 | 4.6 | 7.8 | 4.2 | 1.4 |

Catalyst 2: MgO

| Reaction temperature /°C | 100 | 150 | 200 | 250 | 300 | 350 | 400 | 450 | 500 |
|---|---|---|---|---|---|---|---|---|---|
| Normal ratio /% | - | - | - | - | 60.6 | 49.3 | 49.2 | 41.3 | 31.8 |
| Yield of normal cross Guerbet alcohols /% | 0.0 | 0.0 | 0.0 | 0.0 | 0.1 | 0.4 | 1.4 | 1.9 | 1.5 |

Combination of alcohols: (Ethanol : 1-Propanol = 4 : 1 )

Catalyst 1: HAP

| Reaction temperature /°C | 100 | 150 | 200 | 250 | 300 | 350 | 400 | 450 | 500 |
|---|---|---|---|---|---|---|---|---|---|
| Normal ratio /% | - | 75.3 | 71.4 | 68.3 | 55.7 | 50.7 | 41.4 | 31.2 | 52.2 |
| Yield of normal cross Guerbet alcohols /% | 0.0 | 0.6 | 0.7 | 1.8 | 2.8 | 3.1 | 5.5 | 3.5 | 0.9 |

Catalyst 2: MgO

| Reaction temperature /°C | 100 | 150 | 200 | 250 | 300 | 350 | 400 | 450 | 500 |
|---|---|---|---|---|---|---|---|---|---|
| Normal ratio /% | - | - | - | - | 53.7 | 48.9 | 44.5 | 35.1 | 30.9 |
| Yield of normal cross Guerbet alcohols /% | 0.0 | 0.0 | 0.0 | 0.0 | 0.1 | 0.8 | 1.7 | 1.8 | 1.6 |

FIG. 15

METHOD OF SYNTHESIZING CHEMICAL INDUSTRY RAW MATERIALS AND FUEL COMPOSITIONS

CROSS-REFERENCE TO RELATED APPLICATIONS

This application is a continuation-in-part of U.S. patent application Ser. No. 12/198,059, filed Aug. 25, 2008, which is a continuation-in-part of PCT International Application No. PCT/JP2008/002295, filed Aug. 25, 2008, which claims the benefit of Japanese Patent Application No. 2007-219064, filed Aug. 24, 2007. This application is also a continuation-in-part of PCT International Application No. PCT/JP2008/002295, filed Aug. 25, 2008, which claims the benefit of Japanese Patent Application No. 2007-219064, filed Aug. 24, 2007. The contents of the aforementioned applications are incorporated herein by reference in their entireties.

BACKGROUND OF THE INVENTION

Presently, oxo process comprising synthesizing normal aldehyde by oxidation of normal paraffin and hydrogenating the obtained aldehyde is the mainstream of methods for synthesizing industrial linear alcohol. However, as the price of naphtha, raw material of normal paraffin, is escalating, the profitability is decreasing. Besides the oxo method, a method using methanol (alcohol) and synthetic gas (carbon monoxide and hydrogen) as raw materials is known. However, as carbon monoxide which is harmful is used in the method and that it is a high-pressure reaction, the plant is of a large scale and the profitability is not good. Further, Ziegler method comprising oligomerizing ethylene by trialkylaluminum, forming a long-chain aluminum alkoxide by air-oxidation, and hydrolyzing the resultant to obtain a long-chain primary alcohol is used. With that method, only alcohol having even numbers of carbon atoms having a distribution of 2-28 carbon atoms can be obtained. Moreover, a method for synthesizing 1-propanol from methanol and ethanol by Guerbet method has been proposed, while the yield is not good, as the reaction conditions are specific and thus not suitable for practical use. Furthermore, alcohol is also synthesized from plants such as copra oil (oleochemical), while only alcohol having 8 or 16 carbon atoms can be obtained, and for alcohol having other numbers of atoms, it is necessary to depend on naphtha.

As a method for synthesizing higher alcohol from methanol and ethanol, a method using ununiformed catalysts such as MgO can be exemplified (see non-patent documents 1-5, patent documents 1-4), while these methods are not suitable for industrialization as they are many side reaction products, or the reaction conditions are specific. Further, as a method for synthesizing butanol from ethanol, a method using oxidative products of alkaline-earth metals as catalysts (see non-patent document 6), a method using zeolite substituted with alkaline metal (see non-patent document 7), a method using a mixture of metal oxidative products (see non-patent document 8) can be exemplified. As for a method for manufacturing butadiene from ethanol, a method using a metal oxidative product or a mixture thereof (see non-patent documents 9-11), a method using a sepiolite catalyst which is a cellular acicular clay can be exemplified. However, these methods are not industrially suitable as the catalysts are difficult to prepare, or that the reaction temperature is high.

On the other hand, a method for synthesizing butanol, butadiene, or fuel compositions by using a hydroxyapatite catalyst (see patent documents 7, 8) has been proposed, while as it is a method using only ethanol as raw material, organic compounds that can be synthesized were limited. In other words, as ethanol is a material having 2 carbon atoms, it is not suitable for synthesizing organic compounds having odd numbers of carbon atoms, and particularly, alcohol having odd numbers of carbon atoms cannot be synthesized.

The following non-patent documents, as cited above, are incorporated herein in their entirety. Non-patent document 1: Ueda, W.; Kuwabara, T.; Ohshida, T.; Morikawa, Y. A Low-pressure Guerbet Reaction over Magnesium Oxide Catalyst. J. Chem. Soc., Chem. Commun., 1990, 1558-1559; Non-patent document 2: Ueda, W.; Ohshida, T.; Kuwabara, T.; Morikawa, Y. Condensation of alcohol over solid-base catalyst to form higher alcohols. Catal. Letters, 1992, 12, 97-104; Non-patent document 3: Olson, E. S., Sharma, R. K. and Aulich T. R. Higher-Alcohols Biorefinery Improvement of Catalyst for Ethanol Conversion. Applied Biochemistry and Biotechnology, 2004, vol. 113-116, 913-932; Non-patent document 4: Burk, P. L.; Pruett, R. L. and Campo, K. S. The Rhodium-Promoted Guerbet Reaction Part 1. Higher Alcohols from Lower Alcohols. J. of Molecular Catalysis, 1985, 33, 1-14; Non-patent document 5: Knothe, G. Synthesis, applications, and characterization of Guerbet compounds and their derivatives. Lipid Technology, 2002, September, 101-104; Non-patent document 6: "Dimerisation of ethanol to butanol over solid-base catalysts" A. S. Ndou, N. plint, N. J. Coville, Applied catalysis A: General, 251, p. 337-345 (2003); Non-patent document 7: "Bimolecular Condensation of Ethanol to 1-Butanol Catalyzed by Alkali Cation Zeolites" C. Yang, Z. Meng, J. of Catalysis, 142, p. 37-44 (1993); Non-patent document 8: "Kinetics of a Complex Reaction System-Preparation of n-Butanol from Ethanol in One Step", V. NAGARAJAN, Indian Journal of Technology Vol. 9, October 1971, pp. 380-386; Non-patent document 9: "Butadiene from ethyl alcohol" B. B. Corson, H. E. Jones, C. E. Welling, J. A. Hincley, and E. E. Stahly, Industrial and Engineering Chemistry, Vol. 42. No. 2; Non-patent document 10: One-Step Catalytic Conversion of Ethanol to Butadiene in the Fixed Bed. I. Single-Oxide Catalysis, S. K. Bhattacharyya and N. D. Ganguly, J. Appl. Chem., 12, March 1962; Non-patent document 11: One-Step Catalytic Conversion of Ethanol to Butadiene in the Fixed Bed. II. Binary- and Ternary-Oxide Catalysis, S. K. Bhattacharyya and N. D. Ganguly, J. Appl. Chem., 12, March 1962;

The following patent documents, as cited above, are incorporated herein by reference in their entirety. Patent document 1: U.S. Pat. No. 2,971,033; Patent document 2: U.S. Pat. No. 3,972,952; Patent document 3: U.S. Pat. No. 5,300,695; Patent document 4: U.S. Pat. No. 2,050,788; Patent document 5: Japanese Laid-Open Patent Application No. 57-102822; Patent document 6: Japanese Laid-Open Patent Application No. 58-59928; Patent document 7: WO 99/38822; Patent document 8: WO2006/059729;

BRIEF SUMMARY OF THE INVENTION

In one aspect of the invention is a method for synthesizing 1 or more kinds of organic compounds comprising allowing 2 or more kinds of alcohols to contact hydroxyapatite. In some embodiments, the hydroxyapatite supports metal catalysts or metal ion catalysts acting on alcohol, such as one or more of Ti, Mn, Fe, Co, Ni, Cu, Pt, Ir, Rh, Ag, Zn, Al and Sn. In some embodiments, the hydroxyapatite does not support metal catalysts or metal ion catalysts acting on alcohol. In some embodiments, at least 1 kind of alcohol is methanol or ethanol. In some embodiments, the method comprises allowing ethanol and linear alcohol other than ethanol to contact hydroxyapatite to synthesize a linear alcohol having 3 or more carbon atoms. In some embodiments, the linear alcohol other than ethanol is methanol, 1-propanol, 1-butanol, 1-pentanol, 1-hexanol, 1-heptanol, 1-octanol, or unsaturated alcohols thereof. In some embodiments, the yield of the synthesized linear alcohol is 3C-mol % or more. In some embodiments, the method comprises allowing methanol and alcohol having 3 or more carbon atoms to contact hydroxyapatite to synthesize branched-chain alcohol. In some embodiments, the alcohol having 3 or more carbon atoms is a linear alcohol. In some embodiments, the linear alcohol is 1-propanol, 1-butanol, 1-pentanol, 1-hexanol, 1-heptanol, 1-octanol, or unsaturated alcohols thereof.

In another aspect of the invention is a method for synthesizing 1 or more kinds of organic compounds, comprising allowing 1 kind of alcohols having 3 or more carbons to contact hydroxyapatite. In some embodiments, the hydroxyapatite supports metal catalysts or metal ion catalysts acting on alcohol, such as one or more of Ti, Mn, Fe, Co, Ni, Cu, Pt, Ir, Rh, Ag, Zn, Al and Sn. In some embodiments, the hydroxyapatite does not support metal catalysts or metal ion catalysts acting on alcohol. In some embodiments, the alcohol having 3 or more carbon atoms is propanol, butanol, pentanol, hexanol, heptanol, octanol, or unsaturated alcohols thereof. In some embodiments, the synthesized organic compound is a fuel composition. In some embodiments, the reaction is conducted at 200-600° C.

In another aspect of the invention is a method for synthesizing 1 or more kinds of organic compounds comprising allowing 2 or more kinds of alcohols to contact hydrotalcite. In some embodiments, the hydrotalcite supports metal catalysts or metal ion catalysts acting on alcohol such as one or more of Ti, Mn, Fe, Co, Ni, Cu, Pt, Ir, Rh, Ag, Zn, Al and Sn. In some embodiments, the hydrotalcite does not support metal catalysts or metal ion catalysts acting on alcohol. In some embodiments, the method comprises allowing ethanol and linear alcohol other than ethanol to contact hydrotalcite to synthesize a linear alcohol having 3 or more carbon atoms. In some embodiments, the linear alcohol other than ethanol is methanol, 1-propanol, 1-butanol, 1-pentanol, 1-hexanol, 1-heptanol, 1-octanol, or unsaturated alcohols thereof.

Another aspect of the invention provides a method for synthesizing one or more kinds of organic compounds comprising allowing a mixture of two or more kinds of alcohols to contact a catalyst comprising a calcium phosphate compound, wherein the initial molar percentage of each kind of alcohol is at least 5% of the total moles of initial alcohols in the mixture. In some embodiments, the calcium phosphate compound is hydroxyapatite. In some embodiments, the catalyst is hydrotalcite. In some embodiments, the catalyst supports a metal catalyst or metal ion catalyst such as one or more of Ti, Mn, Fe, Co, Ni, Cu, Pt, Ir, Rh, Ag, Zn, Al and Sn. In some embodiments, the catalyst does not support a metal catalyst or metal ion catalyst. In some embodiments, the mixture includes ethanol and a starting linear alcohol other than ethanol, and at least one of the kinds of organic compounds synthesized is a synthesized linear alcohol having three or more carbon atoms. In some embodiments, the starting linear alcohol other than ethanol is methanol, 1-propanol, 1-butanol, 1-pentanol, 1-hexanol, 1-heptanol, 1-octanol, or an unsaturated alcohol thereof. In some embodiments, the yield of the synthesized linear alcohol is 3C-mol % or more.

In some embodiments, the mixture of two or more kinds of alcohols includes methanol and a starting linear alcohol having at least three carbons, and at least one of the kinds of organic compounds synthesized is a synthesized branched alcohol. In some embodiments, the catalyst supports metal catalysts or metal ion catalysts acting on alcohol, such as one or more of Ti, Mn, Fe, Co, Ni, Cu, Pt, Ir, Rh, Ag, Zn, Al and Sn. In some embodiments, the catalyst does not support metal catalysts or metal ion catalysts acting on alcohol. In some embodiments, the starting linear alcohol having three or more carbon atoms is a linear alcohol. In some embodiments, the linear alcohol is 1-propanol, 1-butanol, 1-pentanol, 1-hexanol, 1-heptanol, 1-octanol, or an unsaturated alcohol thereof.

In some embodiments, the mixture of two or more kinds of alcohols includes methanol, ethanol and a starting linear alcohol having at least three carbons, and at least one of the kinds of organic compounds synthesized is a compound having one more carbons than the number of carbons in the starting linear alcohol. In some embodiments, the starting linear alcohol is 1-propanol, 1-butanol, 1-pentanol, 1-hexanol, 1-heptanol, 1-octanol, or an unsaturated alcohol thereof.

Another aspect of the invention provides a method for synthesizing one or more kinds of organic compounds comprising allowing one kind of alcohol having at least three carbons to contact a catalyst comprising a calcium phosphate compound, the one kind of alcohol is initially substantially free of other kinds of alcohol. In some embodiments, the catalyst does not support a metal catalyst or metal ion catalyst. In some embodiments, the catalyst supports metal catalysts or metal ion catalysts acting on alcohol, such as one or more of Ti, Mn, Fe, Co, Ni, Cu, Pt, Ir, Rh, Ag, Zn, Al and Sn. In some embodiments, the calcium phosphate compound is hydroxyapatite. In some embodiments, the catalyst is hydrotalcite. In some embodiments, the one kind of alcohol is propanol, butanol, pentanol, hexanol, heptanol, octanol, or unsaturated alcohols thereof.

In some embodiments of the methods of the present invention, the synthesized organic compound is a fuel composition. In some embodiments of the methods of the present invention, the method reaction is conducted at about 200° C. to about 600° C. In some embodiments of the methods of the present invention, the initial molar percentage of each kind of alcohol is at least 14%, at least 20% or at about 50%, of the total moles of initial alcohols in the mixture.

BRIEF DESCRIPTION OF THE DRAWINGS

FIG. 2 is a figure showing the yield of alcohol against the reaction temperature, when ethanol and 1-propanol (ethanol:1-propanol=1:4) are used as raw material alcohol;

FIG. 3 is a figure showing the yield of alcohol against the reaction temperature, when ethanol and 1-propanol (ethanol:1-propanol=4:1) are used as raw material alcohol;

FIG. 6 is a table showing product selectivity from an exemplary methanol and ethanol (1:1) reaction;

FIG. 7 is a table showing product selectivity from an exemplary methanol and ethanol (20:1) reaction;

FIG. 8 is a table showing product selectivity from an exemplary ethanol and 1-propanol (4:1) reaction;

FIG. 9 is a table showing product selectivity from an exemplary ethanol and 1-propanol (1:1) reaction;

FIG. 10 is a table showing product selectivity from an exemplary ethanol and 1-propanol (1:4) reaction;

FIG. 11 is a table showing product selectivity from an exemplary ethanol, methanol and 1-propanol (1:5:1) reaction over HAP catalyst;

FIG. 12 is a table showing product selectivity from an exemplary ethanol, methanol and 1-propanol (1:5:1) reaction over MgO catalyst;

FIG. 13 is a table showing product selectivity from an exemplary ethanol, methanol and 1-butanol (1:6:1) reaction over HAP catalyst;

FIG. 14 is a table showing product selectivity from an exemplary ethanol, methanol and 1-butanol (1:6:1) reaction over MgO catalyst;

FIG. 15 is a table showing alcohol product composition under the described exemplary reaction conditions.

DETAILED DESCRIPTION OF THE INVENTION

Figure 1:
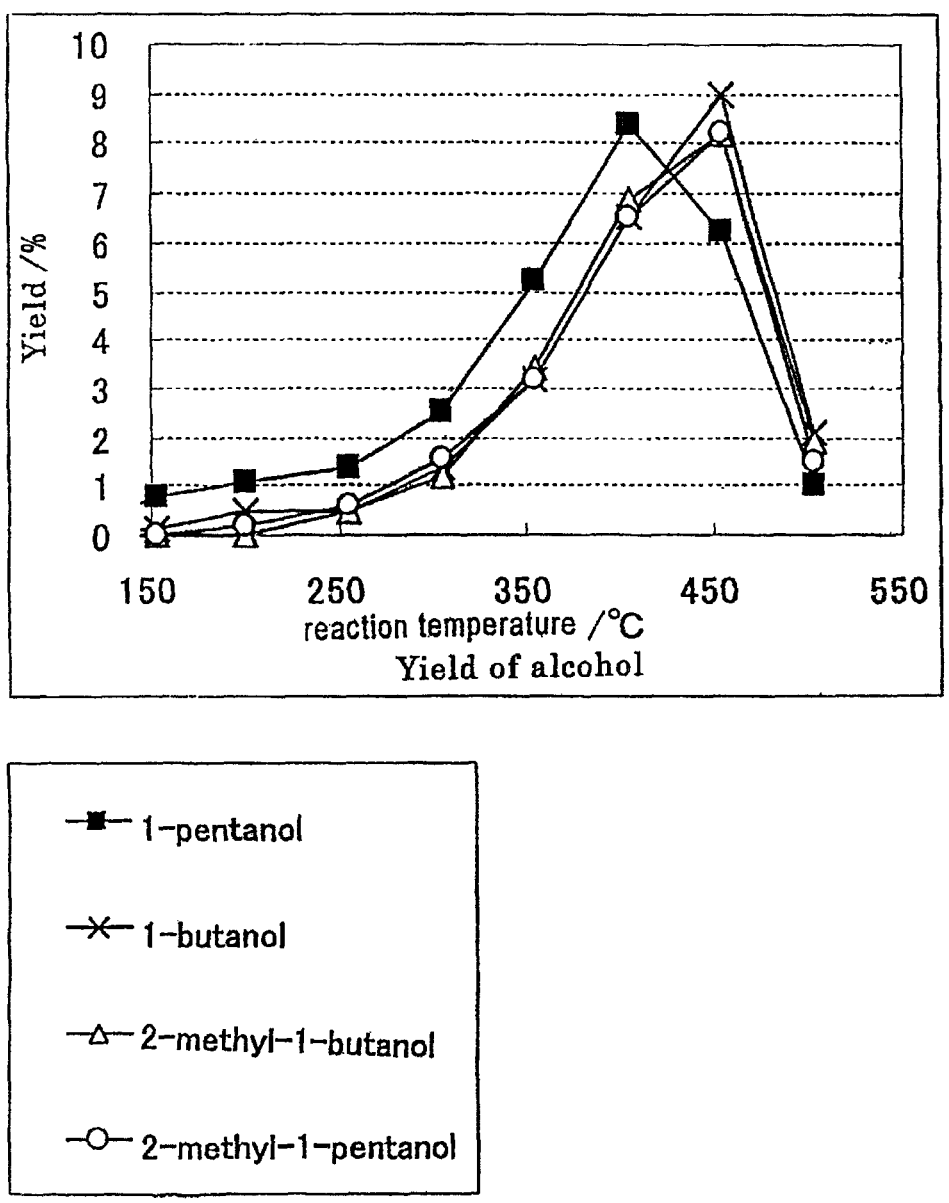
FIG. 1 is a figure showing the yield of alcohol against the reaction temperature, when ethanol and 1-propanol (ethanol:1-propanol=1:1) are used as raw material alcohol.

The present invention relates to a method for synthesizing an organic compound useful as a chemical industry raw material and fuel composition or a mixture thereof.

The object of the present invention is to provide a novel method for manufacturing various organic compounds from 2 or more kinds of alcohol or from 1 kind of alcohol having 3 or more carbon atoms. Particularly, it is to provide a method for synthesizing linear alcohol or branched-chain alcohol in good yield, by using 2 or more kinds of alcohols.

The present inventors made a study for manufacturing organic compounds to be used as a chemical industry raw material, and found out that by using hydroxyapatite or hydrotalcite as a catalyst, various organic compounds can be manufactured from 2 or more kinds of alcohol, or from 1 kind of alcohol having 3 or more carbon atoms. The present invention has been thus completed.

Further, the present inventors made a keen study for synthesizing linear alcohols, under conditions that almost all of the alcohols synthesized by using alcohol raw material were branched-chain alcohols, and that it was estimated to be extremely difficult to synthesize linear alcohols. As a result, they found out that by allowing ethanol and linear alcohol other than ethanol to contact hydroxyapatite or hydrotalcite, a linear alcohol can be synthesized in good yield. Currently, ethanol is synthesized through the conversion of sugars obtained from sugarcanes, beets, etc., by a fermentation method. Recently, a technique for synthesizing ethanol from biomass, agricultural and forestry residues, has been established, and a striking increase in the production of ethanol can be expected in future. Further, as the production cost of ethanol is becoming comparable or less than the crude oil, it is an important object to synthesize chemical industry raw materials using ethanol as a raw material. The process of the present invention uses ethanol derived from plants as a raw material, and the reaction proceeds easily at normal pressure. Thus, comparing with the conventional synthesizing method using fossil or mineral resource, which emit carbon dioxide and promote global heating, as a raw material, it is an important synthesizing method for global environment.

Further, the present inventors found out that by allowing methanol and alcohol having 3 or more carbon atoms to contact hydroxyapatite or hydrotalcite, a branched-chain alcohol can be synthesized in good yield.

In other words, the present invention relates to ("1") a method for synthesizing 1 or more kinds of organic compounds comprising allowing 2 or more kinds of alcohols to contact hydroxyapatite; ("2") the method according to "1", wherein at least 1 kind of alcohol is methanol or ethanol; ("3") the method according to "1" or "2", wherein a linear alcohol having 3 or more carbon atoms is synthesized by allowing ethanol and linear alcohol other than ethanol to contact hydroxyapatite; ("4") the method according to "3", wherein the linear alcohol other than ethanol is methanol, 1-propanol, 1-butanol, 1-pentanol, 1-hexanol, 1-heptanol, 1-octanol, or unsaturated alcohols thereof; ("5") the method according to "3" or "4", wherein the yield of the synthesized linear alcohol is 3C-mol % or more; ("6") the method according to ("1") or ("2"), comprising allowing methanol and alcohol having 3 or more carbon atoms to contact hydroxyapatite to synthesize branched-chain alcohol; ("7") the method according to ("6"), wherein the alcohol having 3 or more carbon atoms is a linear alcohol; ("8") the method according to "7", wherein the linear alcohol is 1-propanol, 1-butanol, 1-pentanol, 1-hexanol, 1-heptanol, 1-octanol, or unsaturated alcohols thereof. In some embodiments of this aspect of the present invention, the hydroxyapatite supports metal catalysts or metal ion catalysts acting on alcohol, such as one or more of Ti, Mn, Fe, Co, Ni, Cu, Pt, Ir, Rh, Ag, Zn, Al and Sn. In some embodiments of this aspect of the present invention, the hydroxyapatite does not support metal catalysts or metal ion catalysts acting on alcohol.

Further, the present invention relates to ("9") a method for synthesizing 1 or more kinds of organic compounds, comprising allowing 1 kind of alcohols having 3 or more carbons to contact hydroxyapatite; ("10") the method according to "9", wherein the alcohol having 3 or more carbon atoms is propanol, butanol, pentanol, hexanol, heptanol, octanol, or unsaturated alcohols thereof; ("11") the method according to "1," "2", "9" or "10", wherein the synthesized organic compound is a fuel composition; ("12") the method according to any one of "1" to "11", wherein the reaction is conducted at 200-600° C. In some embodiments of this aspect of the present invention, the hydroxyapatite supports metal catalysts or metal ion catalysts acting on alcohol, such as one or more of Ti, Mn, Fe, Co, Ni, Cu, Pt, Ir, Rh, Ag, Zn, Al and Sn. In some embodiments of this aspect of the present invention, the hydroxyapatite does not support metal catalysts or metal ion catalysts acting on alcohol.

Further, the present invention relates to ("13") a method for synthesizing 1 or more kinds of organic compounds comprising allowing 2 or more kinds of alcohol to contact hydrotalcite; ("14") the method according to "13", comprising allowing ethanol and linear alcohol other than ethanol to contact hydrotalcite to synthesize a linear alcohol having 3 or more carbon atoms; ("15") the method according to "14", wherein the linear alcohol other than ethanol is methanol, 1-propanol, 1-butanol, 1-pentanol, 1-hexanol, 1-heptanol, 1-octanol, or unsaturated alcohols thereof.

According to the method for synthesizing alcohol of the present invention, various organic compounds can be manufactured from 2 or more kinds of alcohols or from 1 kind of alcohol having 3 or more carbon atoms. Particularly, when using 2 or more kinds of alcohols, linear alcohol or branched-chain alcohol can be synthesized in good yield.

As for a method for synthesizing an organic compound of the present invention (first synthesizing method), it is not particularly limited as long as it is a method comprising allowing 2 or more kinds of alcohols to contact hydroxyapatite. In some embodiments of this aspect of the present invention, the hydroxyapatite supports metal catalysts or metal ion catalysts acting on alcohol, such as one or more of Ti, Mn, Fe, Co, Ni, Cu, Pt, Ir, Rh, Ag, Zn, Al and Sn. In some embodiments of this aspect of the present invention, the hydroxyapatite does not support metal catalysts or metal ion catalysts acting on alcohol. Examples of organic compounds synthesized by the method for synthesizing of the present invention include: paraffins, olefins, dienes, trienes, alcohols, ethers, ketones, aldehydes, and esters. Specific examples include: ethane, ethylene, acetoaldehyde, propylene, propanol, acetone, butene, 1,3-butadiene, 1-butanol, 3-butene-1-ol, t-crotylalcohol, c-crotylalcohol, diethylether, butyraldehyde, 2-butanone, t-crotonaldehyde, c-crotonaldehyde, 1-pentanol, 2-pentanol, 2-pentanone, butylethylether, 1-hexanol, 2-ethyl-1-butanol, hexanal, 1-heptanol, 2-ethyl-1-propanol, octanol, 2-ethyl-1-hexanol, octanol, and nonanol. These organic compounds having 2 or more carbon atoms can be used as a chemical industry raw material, and among these, a mixture of organic compounds having 4 or more carbon atoms can be used as a fuel composition.

As for a raw material alcohol used in the first synthesizing method of the present invention, it is 2 or more kinds of alcohol, and it may be 2 kinds of alcohol, or 3 or more kinds of alcohol. Further, raw material alcohol may be a linear alcohol or branched-chain alcohol, and may be a saturated alcohol or unsaturated alcohol. Further, the number of carbon atoms is not particularly limited, but it is preferred to be an alcohol having 1-22 carbon atoms, from the point of view of easiness to obtain.

Further, it is preferred that at least 1 kind of alcohol of the raw material alcohol, is methanol or ethanol. By using methanol or ethanol for at least 1 kind of alcohol, organic compounds can be synthesized in good yield.

Particularly, according to a method allowing ethanol and linear alcohol other than ethanol to contact hydroxyapatite, it is possible to synthesize a linear alcohol having 3 or more atoms in good yield. The yield is for example, 3C-mol % or more, and preferably 5C-mol % or more. C-mol denotes the number of carbon atoms of the synthesized alcohol/the number of carbon atoms of raw material alcohol used. As for the linear alcohol other than ethanol, from the view point of easiness to obtain or cost, a saturated or unsaturated alcohol having 1-22 carbon atoms is preferred, and a saturated or unsaturated alcohol having 1-8 carbon atoms is more preferred. Specific examples include methanol, 1-propanol, 1-butanol, 1-pentanol, 1-hexanol, 1-heptanol, 1-octanol, and unsaturated alcohol thereof. Further, the amount used (mixing ratio) of ethanol and linear alcohol other than ethanol is not particularly limited, while in order to synthesize linear alcohol more efficiently, it is preferred that the mixing ratio is approximately equimolar (about 1:0.9-1.1) when the conversion rates of the two alcohols are almost the same. When the conversion rates of the two alcohols are different, it is preferred to mix a larger amount of alcohol with the lower conversion rate. Specifically, when using ethanol and 1-propanol, it is particularly preferred to use ethanol in an amount of about 0.9-1.1 (molar ratio) per 1 portion of 1-propanol.

According to a method comprising allowing methanol and alcohol having 3 or more carbon atoms to contact hydroxyapatite, it is possible to synthesize a branched-chain alcohol in good yield. As for the above alcohol having 3 or more carbon atoms, from the view point of easiness to obtain or cost, a saturated or unsaturated alcohol having 3-22 carbon atoms is preferred, and a saturated or unsaturated alcohol having 3-8 carbon atoms is more preferred. Specific examples include propanol, butanol, pentanol, hexanol, heptanol, octanol, and unsaturated alcohol thereof. Among these, linear alcohol is preferred, and specific examples include 1-propanol, 1-butanol, 1-pentanol, 1-hexanol, 1-heptanol, 1-octanol, and unsaturated alcohol thereof. Further, the amount used (mixing ratio) of methanol and alcohol having 3 or more carbon atoms is not particularly limited, while it is preferred to use 0.9 or more (molar ratio) of methanol per 1 alcohol having 3 or more carbon atoms, from the view point that a branched-chain alcohol is synthesized in good yield.

Further, as for a method for synthesizing an organic compound of the present invention (second synthesizing method), is not particularly limited as long as it is a method allowing 1 kind of alcohol having 3 or more carbon atoms to contact hydroxyapatite. In some embodiments of this aspect of the present invention, the hydroxyapatite supports metal catalysts or metal ion catalysts acting on alcohol, such as one or more of Ti, Mn, Fe, Co, Ni, Cu, Pt, Ir, Rh, Ag, Zn, Al and Sn. In some embodiments of this aspect of the present invention, the hydroxyapatite does not support metal catalysts or metal ion catalysts acting on alcohol. Examples of organic compounds synthesized by the synthesizing method of the present invention include, similarly as the above first synthesizing method, paraffins, olefins, dienes, trienes, alcohols, ethers, ketones, aldehydes, and esters. Among these, each organic compound having 2 or more carbon atoms can be used as chemical industry raw material. Further, a mixture of organic compounds having 4 or more carbon atoms can be used as a fuel composition.

As for the above alcohol having 3 or more carbon atoms, it may be a linear alcohol or branched-chain alcohol, and it may be a saturated alcohol or unsaturated alcohol. Further, the number of carbon atoms is not particularly limited, while from the view point of easiness to obtain or cost, a saturated or unsaturated alcohol having 3-22 carbon atoms is preferred, and a saturated or unsaturated alcohol having 3-8 carbon atoms is more preferred. Specific examples include propanol, butanol, pentanol, hexanol, heptanol, octanol, and unsaturated alcohol thereof. Among these, linear alcohol is preferred, and specific examples include 1-propanol, 1-butanol, 1-pentanol, 1-hexanol, 1-heptanol, 1-octanol, and unsaturated alcohol thereof.

Hydroxyapatite used in the synthesizing method of the present invention (first and second synthesizing methods) is one kind of calcium phosphate, and is generally indicated by the stoichiometric composition $Ca_{10}(PO_4)_6(OH)_2$. However, it can form an apatite structure, showing a property of hydroxyapatite, even it is a hydroxyapatite with a non-stoichiometric composition wherein the Ca/P molar ratio does not reach 1.67. Such synthesized hydroxyapatite with a Ca/P molar ratio of approximately 1.4-1.8 is also encompassed within the hydroxyapatite of the present invention. Particularly, in a method for synthesizing an organic compound of the present invention, a hydroxyapatite with a Ca/P molar ratio of 1.60-1.80 is preferred. The hydroxyapatite may be in any form including granule, sphere, pellet, and honeycomb.

Further, in some embodiments, the hydroxyapatite used in the synthesizing method of the present invention does not encompass those supporting metal catalysts or metal ion catalysts acting on alcohol. In some embodiments of this aspect of the present invention, the hydroxyapatite supports metal catalysts or metal ion catalysts acting on alcohol, such as one or more of Ti, Mn, Fe, Co, Ni, Cu, Pt, Ir, Rh, Ag, Zn, Al and Sn. Examples of metal catalyst or metal ion catalyst acting on alcohol include metals or metal ions described in Japanese Laid-Open Patent Application No. 5-305238.

The hydroxyapatite used in the synthesizing method of the present invention may support in advance 1 kind of raw material alcohol such as methanol or ethanol. In other words, before conducting the synthesizing reaction of organic compounds, it is possible to allow hydroxyapatite to react with 1 kind of raw material alcohol, and to use alcohol-supported hydroxyapatite, wherein hydroxyapatite is supporting alcohol. The absorption peak derived from alcohol of the alcohol-supported hydroxyapatite can be observed by infrared spectroscopy. By using the alcohol-supported hydroxyapatite, distribution of reaction products can be controlled. In other words, many products derived from supported alcohol can be synthesized.

In the synthesizing method of the present invention, at least one compound selected from the group consisting of metal oxidative product, zeolite, silica light, clay mineral of the family of kaolin, clay mineral of the family of pyrophyllite, clay mineral of the family of smectite, hydrotalcite, sepiolite, calcium silicate, calcium fluoride, calcium sulfate, apatite fluoride, magnesium hydroxide, chitin, lithium phosphate, aluminum phosphate, and magnesium phosphate, can be mixed to the above hydroxyapatite for controlling the reaction. 2 or more of these compounds can be used in combination.

In the present invention, when synthesizing an organic compound useful as a chemical industry raw material, in order to increase the selectivity of desired organic compounds, the size, surface area, reaction conditions (contact time, reaction temperature, pressure, etc.) of granules used can be appropriately selected.

As for a reaction form in the present invention, it may be a batch method or a sequential method, while a continuous method is preferred from the view point of industrial economic efficiency. Further, a reactor in any form including a fixed bed, a moving bed, a fluidized bed or a slurry bed can be used. Moreover, it may be a liquid phase reaction or a gas phase reaction, and the reaction may be conducted at normal pressure, under pressure, or reduced pressure. In case of a gas phase reaction, a mixed alcohol gas alone may be in contact with hydroxyapatite, or it may be in contact with hydroxyapatite together with an inert carrier gas such as nitrogen or helium. By allowing to contact together with a carrier gas, unnecessary retention of raw material and products may be suppressed, and the reaction may be conducted more efficiently. At that time, in order to maintain the catalyst activity, reactive gas such as hydrogen, hydrocarbon, and water may be accompanied in the carrier gas. Further, in order to prevent that carbons are precipitated on the surface of hydroxyapatite, which may decrease the alcohol conversion rate and change the nature of reactions, it is preferred that a regeneration treatment wherein the hydroxyapatite is heated under oxygen atmosphere, is periodically conducted. In other words, it is preferred that a catalyst regeneration apparatus that is capable of conducting a regeneration treatment as above-mentioned is provided on the reactor.

It is not possible to determine categorically the contact time of alcohol and hydroxyapatite as it affects also the reaction temperature. Generally, in case of a gas phase reaction by a continuous method, the contact time is about 0.1-20 sec. and preferably about 0.4-5 sec. Further, the reaction temperature is generally 100-700° C., and preferably 200-600° C. Particularly, when synthesizing in good yield a linear alcohol by using ethanol and linear alcohol other than ethanol, the reaction temperature is preferably 250-450° C., and more preferably 300-450° C. Further, when synthesizing a branched-chain alcohol in good yield by using methanol and alcohol having 3 or more carbon atoms, the reaction temperature is preferably 250-500° C., and more preferably 300-450° C.

When conducting a gas phase reaction with 2 or more kinds of alcohol, it is preferred to vaporize the alcohol-mixed solution, and it is preferred to vaporize rapidly, without allowing the reaction of 2 or more kinds of alcohol to be conducted. Therefore, as for the vaporizing temperature, a temperature that is higher than the boiling point of the alcohol having the higher boiling point, and at which the alcohol with the lower boiling point does not react is preferred. Specifically, the preferred temperature is, in case of methanol and ethanol, 150-200° C., and in case of ethanol and 1-octanol, 200-250° C.

As the boiling points of 2 or more kinds of alcohol are different, 1 kind of alcohol having been vaporized may be firstly introduced to form a complex catalyst supporting alcohol, and then the other alcohol in form or liquid or gas may be introduced to start the reaction (liquid phase reaction, gas phase reaction). When using methanol or ethanol, it is preferred to firstly introduce methanol or ethanol having a low boiling point, and to form a complex catalyst supporting methanol or ethanol. Generally, the order of alcohol to be introduced may be determined according to the boiling point as in the above, while when using ethanol, it is preferred to introduce ethanol in the first order.

A mixture of organic compounds thus obtained, may be used as a fuel composition etc. directly in form of mixture. Alternatively, a desired organic compound may be separated or purified according to a conventional separation or purification method, for example by rectification, microporous membrane separation, extraction, or adsorption.

Further, as for a method for synthesizing an organic compound of the present invention (third synthesizing method), it is not particularly limited as long as it is a method allowing 2 or more kinds of alcohol to contact hydrotalcite. Organic compounds synthesized by the synthesizing method of the present invention, are similar to the above case using hydroxyapatite, and various organic compounds may be synthesized in good yield. Particularly, when ethanol and linear alcohol other than ethanol is used, a linear alcohol having 3 or more carbon atoms can be synthesized in good yield.

Hydrotalcite used in the present invention is a clay mineral having a composition of $Mg_6Al_2(OH)_{16}CO_3.4H_2O$. Similarly to the above-mentioned hydroxyapatite, it may support alcohol beforehand. In certain embodiments, hydrotalcite can be used in embodiments of the present invention without supporting an additional metal or metal ion. In some embodiments of this aspect of the present invention, the hydrotalcite supports metal catalysts or metal ion catalysts acting on alcohol, such as one or more of Ti, Mn, Fe, Co, Ni, Cu, Pt, Ir, Rh, Ag, Zn, Al and Sn.

Referring to Example 14 and FIG. 15, Another aspect of the present invention include the use of calcium phosphate catalysts, such as hydroxyapatite, or hydrotalcite, in processes and methods to synthesize normal cross-Guerbet alcohol products between ethanol and another normal alcohol. In certain embodiments, the other normal (i.e., unbranched) alcohol can include methanol, 1-propanol, 1-butanol, 1-pentanol, 1-hexanol, 1-heptanol, 1-octanol, or any other suitable normal alcohol. In some embodiments, the normal alcohols may include at least one unsaturated bond (i.e., alkenols or alkynols) as is understood in the art. In some embodiments of this aspect of the present invention, the calcium phosphate catalyst supports metal catalysts or metal ion catalysts acting on alcohol, such as one or more of Ti, Mn, Fe, Co, Ni, Cu, Pt, Ir, Rh, Ag, Zn, Al and Sn. In some embodiments, the calcium phosphate catalyst does not support another substantial metal or metal ion catalyst.

In some embodiments, the starting molar ratio between ethanol and the other normal alcohol is about 20:1, about 18:1, about 16:1, about 15:1, about 12:1, about 10:1, about 8:1, about 6:1, about 5:1, about 4:1, about 3:1, about 2.5:1, about 2:1, about 1.5:1, about 1:1, about 1:1.5, about 1:2, about 1:2.5, about 1:3, about 1:4, about 1:5, about 1:6, about 1:8, about 1:10, about 1:12, about 1:15, about 1:16, about 1:18 or about 1:20. In certain preferred embodiments, the starting molar ratio between ethanol and the other normal alcohol is about 1:20, about 1:4, about 1:1 or about 4:1.

Referring to FIG. 15, an analysis of the products resulting from the reaction of ethanol and 1-propanol under a variety of conditions and catalysts are shown. For each condition, the normal percentage ratio (i.e., the ratio of normal C5 alcohol product over the total normal and branched C5 alcohol products) and the yield of normal cross-Guerbet alcohol are shown. In these examples, the yield of normal cross-Guerbet alcohol in a reaction of ethanol and 1-propanol is the yield of 1-pentanol (the non-branched alcohol cross-product of ethanol and 1-propanol) as a percentage of total alcohols supplied. The results show that the use of calcium phosphate-based catalysts (i.e., hydroxyapatite) or hydrotalcite results in an unexpected increase in selectivity of the normal cross-product, particular in the higher temperature ranges of between at or about 300° C. to at or about 450° C. when compared to the other catalysts. Such increased selectivity is advantageous when used at these higher reaction temperatures, which are conditions that would have been expected to have a relatively higher percentage of corresponding or other branched alcohol products.

Referring to Examples 15 and 16, and FIGS. 16A-19B, another aspect of the present invention include the use of calcium phosphate catalysts, such as hydroxyapatite, or hydrotalcite, in processes and methods to synthesize alcohol products in increased yield and selectivity. In certain embodiments, these methods and processes include three alcohols in as starting reagents: a first and a second alcohol each having a length of at least two carbons, and a third alcohol, methanol. In preferred embodiments, the first alcohol is ethanol and the second alcohol has a length of at least three carbons. In certain preferred embodiments, the third alcohol of at least three carbons is unbranched. In certain embodiments, the third alcohol is selected from 1-propanol, 1-butanol, 1-pentanol, 1-hexanol, 1-heptanol, 1-octanol, or any other suitable normal alcohol. In some preferred embodiments, the third alcohol is preferably 1-propanol or 1-butanol. In some embodiments, the normal alcohols may include at least one unsaturated bond (i.e., alkenols or alkynols) as is understood in the art. In some embodiments of this aspect of the present invention, the calcium phosphate catalyst supports metal catalysts or metal ion catalysts acting on alcohol, such as one or more of Ti, Mn, Fe, Co, Ni, Cu, Pt, Ir, Rh, Ag, Zn, Al and Sn. In some embodiments of this aspect of the present invention, the calcium phosphate catalyst does not support another substantial metal or metal ion catalyst.

In some embodiments, the starting molar ratio between the first alcohol and the second alcohol is about 20:1, about 18:1, about 16:1, about 15:1, about 12:1, about 10:1, about 8:1, about 6:1, about 5:1, about 4:1, about 3:1, about 2.5:1, about 2:1, about 1.5:1, about 1:1, about 1:1.5, about 1:2, about 1:2.5, about 1:3, about 1:4, about 1:5, about 1:6, about 1:8, about 1:10, about 1:12, about 1:15, about 1:16, about 1:18 or about 1:20. In certain preferred embodiments, the starting molar ratio between the first alcohol and the second alcohol is about 1:1.

In some embodiments, the starting molar ratio between the first alcohol and the third alcohol is about 1:1, about 1:1.5, about 1:2, about 1:2.5, about 1:3, about 1:4, about 1:5, about 1:6, about 1:8, about 1:10, about 1:12, about 1:15, about 1:16, about 1:18 or about 1:20. In certain preferred embodiments, the starting molar ratio between the first alcohol and the third alcohol is about 1:5 or about 1:6.

Figure 16A:
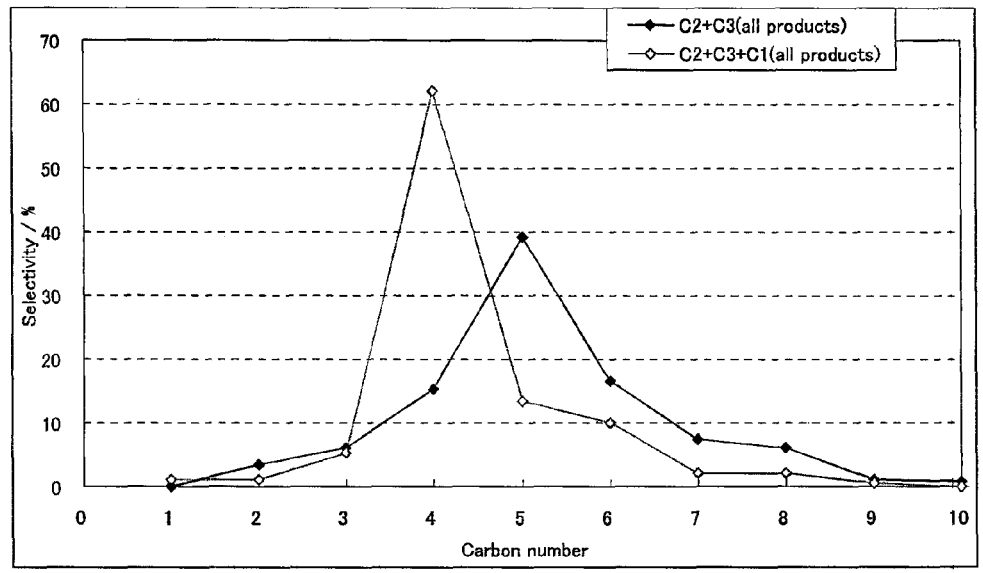
FIGS. 16A-19B are graphs showing distribution of products based on carbon number for certain exemplary conditions.
Figure 16B:
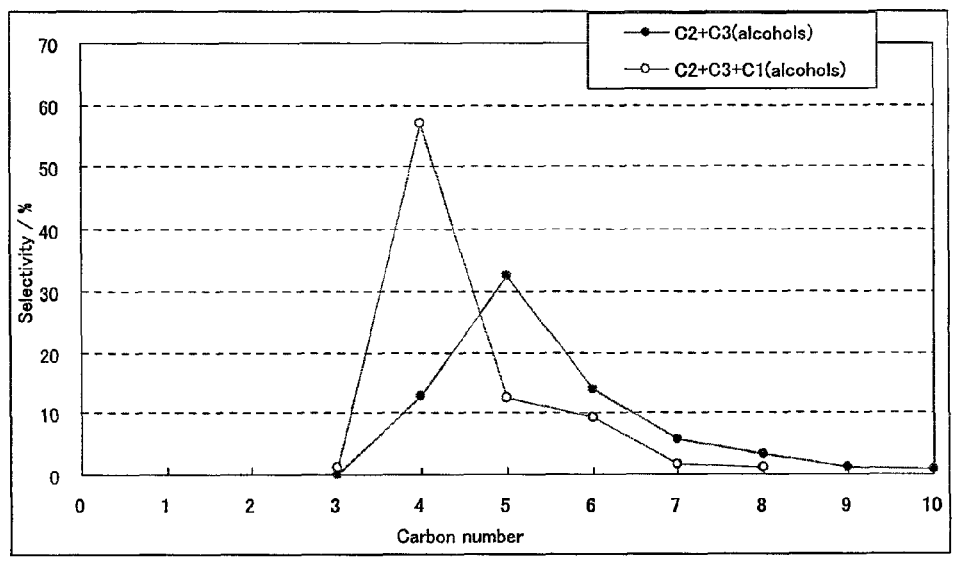

Referring to FIGS. 16A and 16B, as described in Example 15, an analysis of the products resulting from a reaction of ethanol, methanol and 1-propanol under a variety of conditions over hydroxyapatite is shown. In FIG. 16A, the reaction between ethanol and 1-propanol under the described conditions results in a relatively high yield (about ~40%) and high selectivity for five-carbon compounds with respect to the products of other sizes. In comparison, the reaction between ethanol, 1-propanol, and a several-fold molar excess of methanol resulted in the production of four-carbon compounds with an increase of both yield (>60%) and selectivity for products of this size. The distribution indicates that this apparent "shift" is evident over most of the distribution. As depicted in FIG. 16B, this "shift" of the products to a higher-yield and selectivity of four-carbon products remains true when only the alcohol products are measured.

Figure 17A:
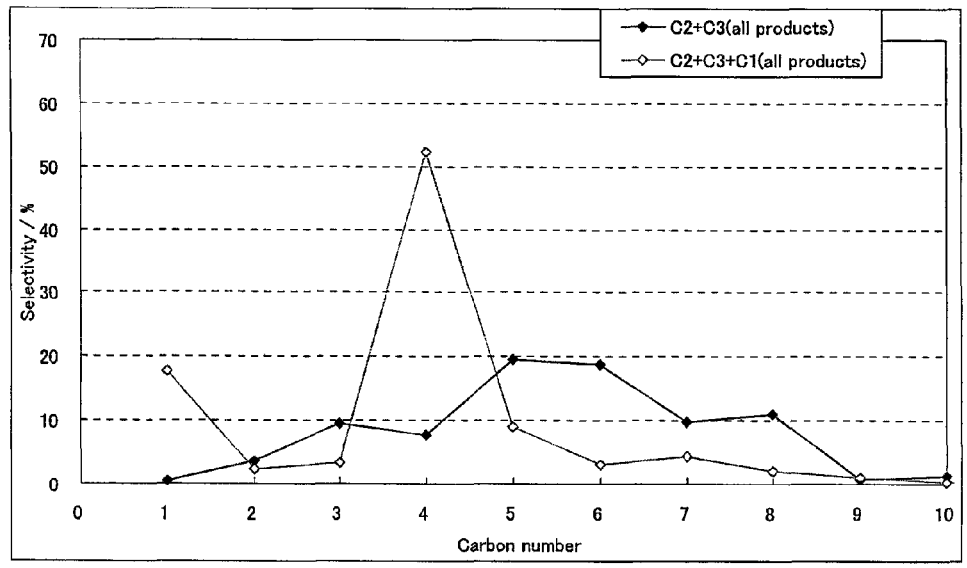
Figure 17B:
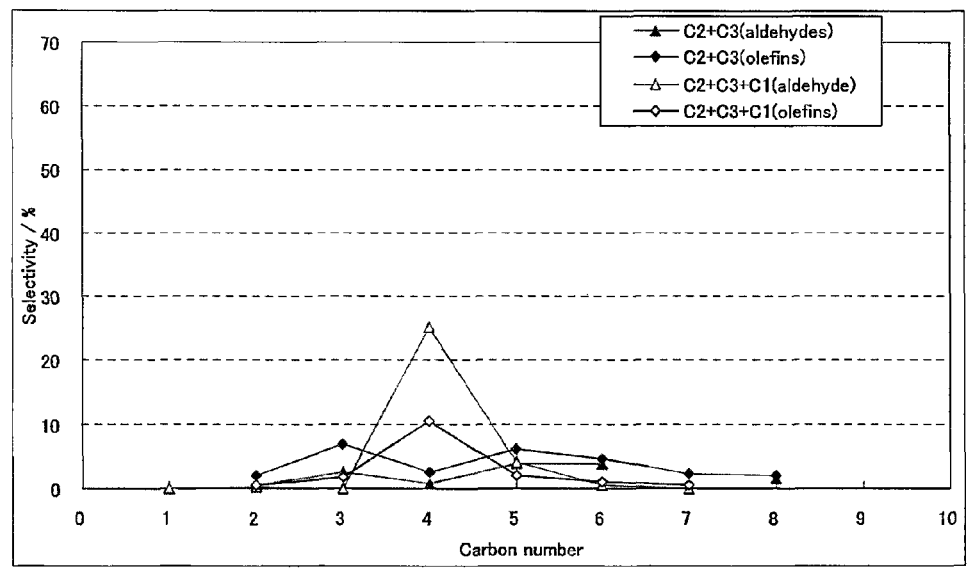

Referring to FIGS. 17A and 17B, the exemplary reactions depicted in FIGS. 16A and 16B and described in Example 15 are performed in essentially the same way at 500° C. Here, as shown in FIG. 17A, the increased selectivity and yield of four-carbon products in the three-alcohol reaction, relative to the two-alcohol reaction, remains evident. As shown in FIG. 17B, this apparent shift and increase in yield and selectivity cannot be completely attributed to side-products of aldehydes or olefins.

Figure 18A:
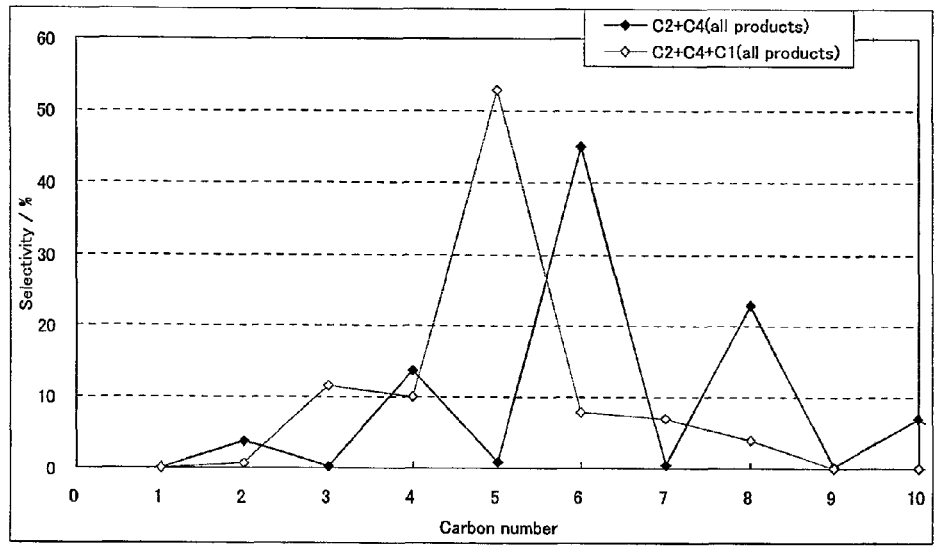
Figure 18B:
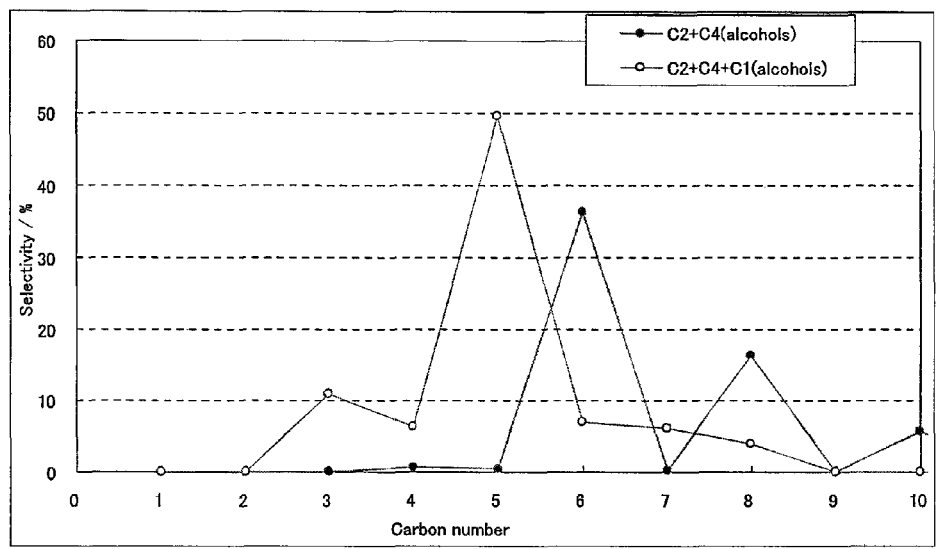

Referring to FIGS. 18A and 18B, as described in Example 16, an analysis of the products resulting from a reaction of ethanol, methanol and 1-butanol under a variety of conditions over hydroxyapatite is shown. In FIG. 18A, the reaction between ethanol and 1-butanol under the described conditions results in a relatively high yield (about ~45%) and high selectivity for six-carbon compounds with respect to the products of other sizes. In comparison, the reaction between ethanol, 1-butanol, and a several-fold molar excess of methanol resulted in the production of five-carbon compounds with an increase of both yield (>50%) and selectivity for products of this size. The distribution indicates that this apparent "shift" is evident over most of the distribution. As depicted in FIG. 18B, this "shift" of the products to a higher-yield and selectivity of five-carbon products remains true when only the alcohol products are measured.

Figure 19A:
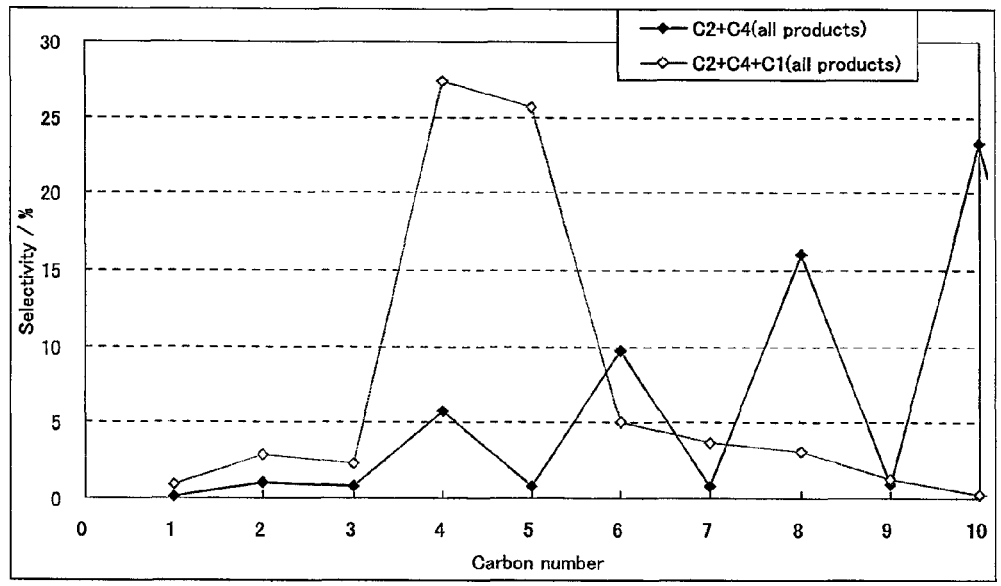
Figure 19B:
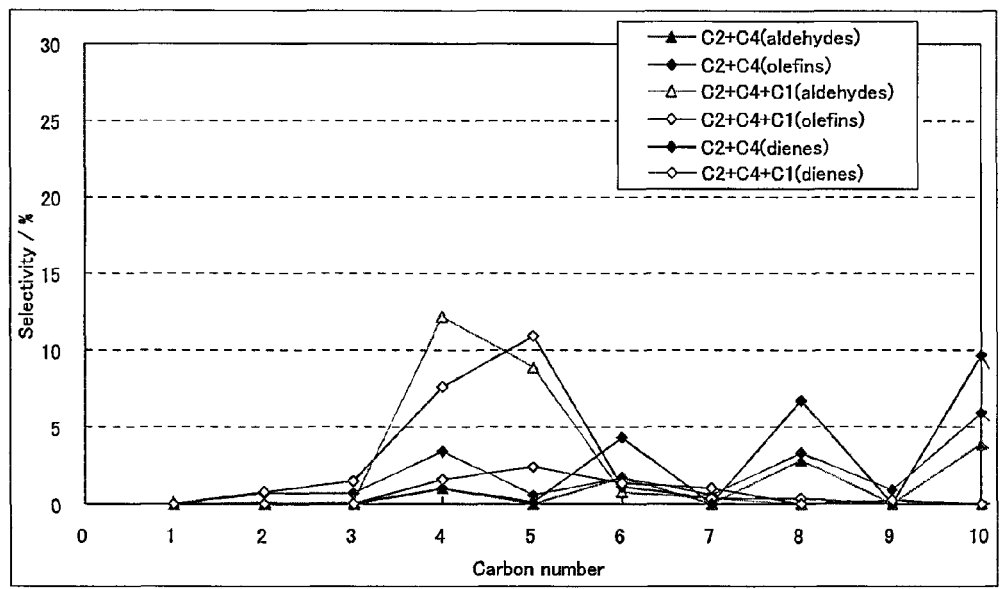

Referring to FIGS. 19A and 19B, the exemplary reactions depicted in FIGS. 18A and 18B and described in Example 15 are performed in essentially the same way at 500° C. Here, as shown in FIG. 17A, the increased selectivity and yield of five-carbon products in the three-alcohol reaction, relative to the two-alcohol reaction, remains evident. As shown in FIG. 19B, this apparent shift and increase in yield and selectivity cannot be completely attributed to side-products of aldehydes, dienes or olefins.

Thus, such increased and yield and selectivity resulting from the three-alcohol reaction shown in these examples are advantageous to obtain a desired product in both increased yield and specificity. Further, these examples of the present invention indicate that certain products that are typically difficult to obtain, such as products having an odd-number of carbons, can be obtained with increase yield and specificity. Further, another advantage of the present invention is that such increased yield and specificity can be achieved at relatively higher reaction temperatures.

Raw material alcohol or synthesizing method is similar to that of the above first or second synthesizing method, and thus the detailed explanation is abbreviated.

The present invention will be explained in more detail in the following by referring to the Examples, while the technical scope of the present invention shall not be limited to these exemplifications.

EXAMPLES

Example 1

First Synthesizing Method

Example 1-1

Catalyst

As for a catalyst used in the Example, a hydroxyapatite prepared by a common method was used. In the Table, "HAP1" denotes a hydroxyapatite which Ca/P molar ratio is 1.66, "HAP2" denotes a hydroxyapatite which Ca/P molar ratio is 1.64, and "HAP3" denotes a hydroxyapatite which Ca/P molar ratio is 1.61. As for a catalyst used in the comparative example, MgO reagent (Wako Pure Chemicals) boiled and hydrated in distilled water (see Ueda, W.; Kuwabara, T.; Ohshida, T.; Morikawa, Y. A Low-pressure Guerbet Reaction over Magnesium Oxide Catalyst. J. Chem. Soc., Chem. Commun., 1990, 1558-1559), as for $ZrO_2$, a reference catalyst of Catalyst (JRC-ZRO-5), and as for others, reagents from Wako Pure Chemicals were used, respectively.

Evaluation of Catalyst Property

A fixed bed gas flow catalytic reactor (Ohkura Riken) was used as a reactor. 0.2-4 cc of hydroxyapatite was filled in a silica reaction tube with a diameter of 5 mm. As a pretreatment, thermal dehydration treatment was conducted for 30 min under a carrier gas atmosphere (1% Ar/He base; flow 112 ml/min) at 500° C. Following the pretreatment, mixed alcohol gas diluted with helium (alcohol concentration 20 vol %) was introduced so that GHSV becomes 500-10000 (1/h) to allow reaction at normal pressure. For the reaction temperature, a sampling was conducted every 50° C. from 100-500° C. A gas chromatography mass spectrometer (GC-MS) was used for the identification of the components of the reaction gas, and a gas chromatography (GC) (detector: FID) was used for the measurement of the alcohol conversion rate and the selectivity of the synthetic gas, to quantify the amount of each component from the peak surface value of each component. For each test, the yield of organic compounds having 2 or more carbon atoms (C2+), organic compounds having 4 or more carbon atoms (C4+), alcohol (linear and branched-chain), and linear alcohol were measured. The results are shown in Tables 1-4. In the Tables, "n-C" denotes normal alcohol, "b-C" denotes branched chain alcohol, and "C=" denotes unsaturated alcohol.

Organic Compounds Having 2 or More Carbon Atoms (C2+)

Yield of organic compounds of C2 or more in various combinations of raw material alcohols is shown in Table 1.

TABLE 1

| | Yield of C2+ organic compounds (%) | | | | | | | | | |
|---|---|---|---|---|---|---|---|---|---|---|
| Test examples | 1 | 2 | 3 | 4 | 5 | 6 | 7 | 8 | 9 | 10 |
| catalysts | HAP1 | HAP1 | HAP1 | HAP2 | HAP1 | HAP1 | HAP1 | HAP1 | HAP3 | HAP2 |
| combination of alcohol | C1 C2 | C1 n-C3 | C1 n-C5 | C2 n-C3 | C2:n-C3 = 1:9 | C2:n-C3 = 1:4 | C2:n-C3 = 4:1 | C2:n-C3 = 9:1 | C2 b-C3 | C2 n-C4 |
| reaction temperature (° C.) | | | | | | | | | | |
| 100 | 0.2 | 0.1 | 0.0 | 0.1 | 0.1 | 0.1 | 0.2 | 0.1 | 0.2 | 0.2 |
| 150 | 1.1 | 1.3 | 1.4 | 1.7 | 1.3 | 1.3 | 1.6 | 1.0 | 2.1 | 1.6 |
| 200 | 2.2 | 2.6 | 2.9 | 2.8 | 2.5 | 2.4 | 2.8 | 2.9 | 3.5 | 2.5 |
| 250 | 5.4 | 4.3 | 5.8 | 4.6 | 6.8 | 5.2 | 6.3 | 6.0 | 7.7 | 4.1 |
| 300 | 14.8 | 13.3 | 20.8 | 9.8 | 20.6 | 16.0 | 18.8 | 19.9 | 31.7 | 8.8 |
| 350 | 18.0 | 29.4 | 37.6 | 19.4 | 41.2 | 27.2 | 26.2 | 26.8 | 84.0 | 14.1 |
| 400 | 40.6 | 58.5 | 66.1 | 41.7 | 81.9 | 61.2 | 56.7 | 57.6 | 96.9 | 32.8 |
| 450 | 82.1 | 86.6 | 96.6 | 86.6 | 97.3 | 93.9 | 93.3 | 89.2 | 99.7 | 79.0 |
| 500 | 95.7 | 95.8 | 99.2 | 98.2 | 99.2 | 99.2 | 99.0 | 99.4 | 99.5 | 99.4 |
| 550 | | | | | | | | | | |

| | Yield of C2+ organic compounds (%) | | | | | | | | | |
|---|---|---|---|---|---|---|---|---|---|---|
| Test examples | 11 | 12 | 13 | 14 | 15 | 16 | 17 | 18 | 19 | 20 |
| catalysts | HAP1 | HAP3 | HAP1 | HAP2 | HAP2 | HAP2 | HAP2 | HAP2 | HAP1 | HAP2 |
| combination of alcohol | C2 n-C4⁻ | C2 b-C4 | C2 n-C5 | C2 n-C6 | C2 b-C6 | C2 n-C8 | C2 b-C8 | n-C3 n-C4 | b-C3 b-C4 | n-C3 n-C5 |
| reaction temperature (° C.) | | | | | | | | | | |
| 100 | 1.6 | 0.1 | 0.1 | 0.1 | 0.1 | 0.1 | 0.1 | 0.1 | 0.2 | 0.1 |
| 150 | 9.0 | 1.3 | 1.6 | 1.8 | 1.5 | 1.9 | 0.8 | 1.7 | 2.6 | 1.9 |
| 200 | 15.9 | 2.4 | 2.7 | 2.9 | 1.8 | 2.6 | 1.7 | 2.5 | 3.3 | 2.7 |
| 250 | 25.7 | 4.6 | 6.1 | 7.4 | 3.6 | 8.8 | 2.3 | 6.6 | 9.5 | 8.6 |
| 300 | 46.8 | 9.5 | 21.8 | 12.5 | 5.8 | 13.3 | 7.4 | 16.8 | 24.2 | 18.6 |
| 350 | 82.2 | 17.4 | 30.8 | 27.2 | 12.7 | 31.0 | 15.9 | 28.6 | 60.9 | 29.2 |
| 400 | 90.6 | 70.5 | 60.9 | 64.2 | 24.5 | 67.7 | 26.2 | 55.7 | 67.2 | 57.7 |
| 450 | 98.2 | 99.1 | 93.7 | 90.1 | 64.8 | 91.2 | 63.6 | 91.1 | 83.0 | 94.4 |
| 500 | 99.8 | 99.9 | 99.6 | 99.6 | 96.8 | 99.5 | 96.0 | 98.6 | 97.6 | 99.7 |
| 550 | | | | | | | | | | |

TABLE 1-continued

| Comparative examples | 1 | 2 | 3 | 4-1 | 4-2 | 4-3 | 4-4 | 6 |
|---|---|---|---|---|---|---|---|---|
| catalysts | MgO | MgO | MgO | MgO | CaF$_2$ | CaSiO$_3$ | ZrO$_2$ | MgO |
| combination of alcohol | C1 C2 | C1 n-C3 | C1 n-C5 | C2 n-C3 | C2 n-C3 | C2 n-C3 | C2 n-C3 | C2:n-C3 = 1:4 |
| reaction temperature (° C.) | | | | | | | | |
| 100 | 0.0 | 0.0 | 0.0 | 0.0 | 0.1 | 0.1 | 0.0 | 0.0 |
| 150 | 0.1 | 0.1 | 0.4 | 0.1 | 0.3 | 0.2 | 0.0 | 0.1 |
| 200 | 0.2 | 0.1 | 0.7 | 0.1 | 0.2 | 0.2 | 0.1 | 0.1 |
| 250 | 0.3 | 0.3 | 1.0 | 0.3 | 0.2 | 0.2 | 0.5 | 0.2 |
| 300 | 2.1 | 2.1 | 3.8 | 1.9 | 1.0 | 0.4 | 4.6 | 1.3 |
| 350 | 9.0 | 12.0 | 15.3 | 8.3 | 6.1 | 2.3 | 15.9 | 5.9 |
| 400 | 24.1 | 29.5 | 29.3 | 24.1 | 16.1 | 8.8 | 36.7 | 20.7 |
| 450 | 51.7 | 51.6 | 53.6 | 42.3 | 11.6 | 22.0 | 58.4 | 41.9 |
| 500 | 72.7 | 65.9 | 74.3 | 70.8 | 22.9 | 47.9 | 76.1 | 70.0 |
| 550 | | | | | | | | |

| Comparative examples | 7 | 10-1 | 10-2 | 11 | 12 | 16 | 19 |
|---|---|---|---|---|---|---|---|
| catalysts | MgO | MgO | CaF$_2$ | MgO | MgO | CaSiO$_3$ | MgO |
| combination of alcohol | C2:n-C3 = 4:1 | C2 n-C4 | C2 n-C4 | C2 n-C4$^-$ | C2 b-C4 | C2 n-C8 | b-C3 b-C4 |
| reaction temperature (° C.) | | | | | | | |
| 100 | 0.0 | 0.0 | 0.0 | 0.5 | 0.0 | 0.0 | 0.1 |
| 150 | 0.1 | 0.1 | 0.1 | 1.3 | 0.1 | 0.1 | 0.6 |
| 200 | 0.1 | 0.2 | 0.1 | 1.8 | 0.1 | 0.1 | 1.2 |
| 250 | 0.3 | 0.5 | 0.1 | 2.5 | 0.3 | 0.3 | 2.9 |
| 300 | 2.3 | 2.2 | 0.2 | 10.2 | 1.5 | 0.5 | 3.7 |
| 350 | 11.8 | 7.8 | 1.7 | 27.6 | 3.6 | 1.8 | 12.0 |
| 400 | 27.8 | 19.8 | 7.6 | 45.7 | 13.5 | 5.6 | 24.8 |
| 450 | 47.0 | 45.0 | 12.1 | 63.1 | 41.8 | 15.9 | 36.3 |
| 500 | 75.7 | 73.4 | 24.9 | 81.8 | 75.4 | 42.3 | 61.0 |
| 550 | | | | | | | |

Organic Compounds Having 4 or More Carbon Atoms (C4+)

Yield of organic compounds of C4 or more in various combinations of raw material alcohols is shown in Table 2.

TABLE 2

| | Yield of C4+ organic compounds (%) | | | | | | | | | |
|---|---|---|---|---|---|---|---|---|---|---|
| Test examples | 1 | 2 | 3 | 4 | 5 | 6 | 7 | 8 | 9 | 10 |
| catalysts | HAP1 | HAP1 | HAP1 | HAP2 | HAP1 | HAP1 | HAP1 | HAP1 | HAP3 | HAP2 |
| combination of alcohol | C1 C2 | C1 n-C3 | C1 n-C5 | C2 n-C3 | C2:n-C3 = 1:9 | C2:n-C3 = 1:4 | C2:n-C3 = 4:1 | C2:n-C3 = 9:1 | C2 b-C3 | C2 n-C4 |
| reaction temperature (° C.) | | | | | | | | | | |
| 100 | 0.2 | 0.1 | 0.0 | 0.0 | 0.1 | 0.1 | 0.1 | 0.1 | 0.1 | 0.1 |
| 150 | 0.8 | 1.0 | 1.2 | 1.2 | 1.2 | 1.1 | 1.3 | 0.9 | 1.8 | 1.4 |
| 200 | 1.8 | 2.2 | 2.6 | 2.2 | 2.2 | 2.2 | 2.3 | 2.8 | 2.9 | 1.9 |
| 250 | 4.6 | 3.8 | 5.5 | 3.6 | 5.9 | 4.5 | 5.6 | 5.9 | 6.7 | 3.2 |
| 300 | 11.5 | 12.8 | 20.7 | 7.2 | 18.8 | 15.4 | 18.0 | 19.7 | 25.8 | 5.7 |
| 350 | 14.5 | 27.5 | 37.6 | 17.9 | 38.6 | 25.2 | 24.6 | 26.6 | 62.4 | 13.6 |
| 400 | 33.9 | 55.4 | 65.9 | 37.7 | 58.2 | 56.7 | 53.0 | 52.3 | 48.0 | 31.5 |
| 450 | 77.6 | 83.8 | 95.5 | 77.0 | 84.7 | 86.0 | 85.8 | 82.8 | 39.1 | 76.5 |
| 500 | 89.1 | 91.3 | 94.5 | 85.4 | 86.5 | 87.5 | 88.1 | 86.4 | 31.0 | 97.6 |
| 550 | | | | | | | | | | |

TABLE 2-continued

| | Yield of C4+ organic compounds (%) | | | | | | | | | |
|---|---|---|---|---|---|---|---|---|---|---|
| Test examples | 11 | 12 | 13 | 14 | 15 | 16 | 17 | 18 | 19 | 20 |
| catalysts | HAP1 | HAP3 | HAP1 | HAP2 | HAP2 | HAP2 | HAP2 | HAP2 | HAP1 | HAP2 |
| combination of | C2 | C2 | C2 | C2 | C2 | C2 | C2 | n-C3 | b-C3 | n-C3 |
| alcohol | n-C4⁻ | b-C4 | n-C5 | n-C6 | b-C6 | n-C8 | b-C8 | n-C4 | b-C4 | n-C5 |
| reaction temperature (° C.) | | | | | | | | | | |
| 100 | 1.5 | 0.0 | 0.0 | 0.0 | 0.0 | 0.0 | 0.0 | 0.1 | 0.1 | 0.0 |
| 150 | 8.9 | 1.2 | 1.5 | 1.7 | 1.4 | 1.8 | 0.7 | 1.6 | 2.6 | 1.8 |
| 200 | 15.5 | 2.3 | 2.5 | 2.7 | 1.7 | 2.5 | 1.5 | 2.2 | 3.3 | 2.4 |
| 250 | 25.5 | 4.4 | 5.8 | 7.2 | 3.5 | 8.6 | 2.1 | 6.1 | 9.5 | 6.9 |
| 300 | 46.0 | 9.2 | 21.7 | 12.3 | 5.7 | 13.1 | 7.2 | 15.4 | 24.2 | 16.7 |
| 350 | 80.6 | 16.1 | 30.4 | 27.0 | 12.5 | 30.4 | 15.5 | 26.7 | 60.8 | 26.9 |
| 400 | 88.9 | 63.7 | 60.1 | 64.0 | 23.5 | 67.5 | 25.2 | 46.3 | 66.1 | 48.4 |
| 450 | 95.7 | 82.4 | 92.3 | 89.8 | 62.4 | 89.7 | 62.5 | 80.1 | 79.0 | 81.7 |
| 500 | 95.7 | 98.9 | 95.0 | 98.9 | 93.6 | 99.1 | 92.8 | 87.6 | 92.5 | 89.3 |
| 550 | | | | | | | | | | |

| Comparative examples | 1 | 2 | 3 | 4-1 | 4-2 | 4-3 | 4-4 | 6 |
|---|---|---|---|---|---|---|---|---|
| catalysts | MgO | MgO | MgO | MgO | CaF₂ | CaSiO₃ | ZrO₂ | MgO |
| combination of | C1 | C1 | C1 | C2 | C2 | C2 | C2 | C2:n-C3 = |
| alcohol | C2 | n-C3 | n-C5 | n-C3 | n-C3 | n-C3 | n-C3 | 1:4 |
| reaction temperature (° C.) | | | | | | | | |
| 100 | 0.0 | 0.0 | 0.0 | 0.0 | 0.0 | 0.0 | 0.0 | 0.0 |
| 150 | 0.1 | 0.1 | 0.4 | 0.1 | 0.1 | 0.1 | 0.0 | 0.1 |
| 200 | 0.1 | 0.1 | 0.7 | 0.1 | 0.0 | 0.0 | 0.0 | 0.1 |
| 250 | 0.2 | 0.2 | 1.0 | 0.2 | 0.0 | 0.0 | 0.1 | 0.1 |
| 300 | 1.1 | 1.7 | 3.8 | 1.2 | 0.2 | 0.1 | 1.4 | 0.8 |
| 350 | 5.5 | 10.3 | 15.3 | 6.0 | 2.1 | 0.6 | 8.7 | 4.0 |
| 400 | 16.6 | 24.3 | 29.3 | 17.5 | 4.7 | 3.1 | 20.4 | 14.0 |
| 450 | 41.4 | 43.7 | 52.8 | 29.3 | 2.4 | 8.4 | 29.3 | 28.3 |
| 500 | 56.6 | 55.5 | 71.5 | 49.9 | 6.2 | 20.7 | 36.9 | 47.4 |
| 550 | | | | | | | | |

| Comparative examples | 7 | 10-1 | 10-2 | 11 | 12 | 16 | 19 |
|---|---|---|---|---|---|---|---|
| catalysts | MgO | MgO | CaF₂ | MgO | MgO | CaSiO₃ | MgO |
| combination of | C2:n-C3 = | C2 | C2 | C2 | C2 | C2 | b-C3 |
| alcohol | 4:1 | n-C4 | n-C4 | n-C4⁻ | b-C4 | n-C8 | b-C4 |
| reaction temperature (° C.) | | | | | | | |
| 100 | 0.0 | 0.0 | 0.0 | 0.4 | 0.0 | 0.0 | 0.1 |
| 150 | 0.0 | 0.1 | 0.1 | 1.2 | 0.1 | 0.1 | 0.5 |
| 200 | 0.0 | 0.1 | 0.1 | 1.7 | 0.1 | 0.1 | 1.0 |
| 250 | 0.2 | 0.4 | 0.1 | 2.3 | 0.2 | 0.3 | 2.6 |
| 300 | 1.4 | 1.8 | 0.1 | 10.0 | 1.4 | 0.5 | 1.7 |
| 350 | 8.7 | 6.4 | 1.3 | 27.1 | 3.4 | 1.7 | 4.6 |
| 400 | 21.2 | 16.3 | 5.7 | 44.9 | 12.6 | 5.5 | 10.8 |
| 450 | 33.2 | 37.5 | 8.7 | 62.5 | 38.2 | 15.7 | 16.6 |
| 500 | 50.3 | 62.1 | 17.2 | 80.2 | 64.8 | 41.9 | 34.6 |
| 550 | | | | | | | |

Alcohol (Linear and Branched-chain)

Yield of alcohol (linear and branched-chain) in various combinations of raw material alcohols is shown in Table 3.

TABLE 3

| Test examples | Yield of synthesized alcohol (%) | | | | | | | | | |
|---|---|---|---|---|---|---|---|---|---|---|
| | 1 | 2 | 3 | 4 | 5 | 6 | 7 | 8 | 9 | 10 |
| catalysts | HAP1 | HAP1 | HAP1 | HAP2 | HAP1 | HAP1 | HAP1 | HAP1 | HAP3 | HAP2 |
| combination of alcohol | C1 C2 | C1 n-C3 | C1 n-C5 | C2 n-C3 | C2:n-C3 = 1:9 | C2:n-C3 = 1:4 | C2:n-C3 = 4:1 | C2:n-C3 = 9:1 | C2 b-C3 | C2 n-C4 |
| reaction temperature (° C.) | | | | | | | | | | |
| 100 | 0.0 | 0.0 | 0.0 | 0.0 | 0.0 | 0.0 | 0.0 | 0.0 | 0.0 | 0.0 |
| 150 | 0.7 | 0.7 | 1.0 | 0.9 | 1.0 | 0.8 | 0.9 | 0.8 | 1.5 | 0.8 |
| 200 | 1.5 | 1.7 | 2.2 | 1.8 | 1.6 | 2.1 | 1.9 | 2.0 | 2.2 | 1.5 |
| 250 | 4.1 | 3.2 | 4.8 | 3.0 | 3.3 | 3.6 | 4.8 | 4.4 | 5.7 | 2.6 |
| 300 | 10.5 | 9.6 | 19.2 | 6.0 | 16.7 | 12.8 | 14.9 | 15.8 | 13.2 | 4.0 |
| 350 | 12.4 | 19.9 | 32.1 | 15.4 | 26.9 | 20.8 | 19.5 | 21.7 | 6.3 | 9.8 |
| 400 | 23.6 | 39.0 | 51.2 | 28.3 | 40.2 | 42.0 | 37.2 | 38.3 | 0.6 | 18.8 |
| 450 | 27.8 | 33.4 | 34.4 | 31.6 | 28.6 | 32.1 | 27.1 | 26.5 | 0.0 | 24.9 |
| 500 | 8.7 | 9.0 | 7.8 | 6.5 | 6.1 | 8.2 | 5.5 | 5.9 | 0.0 | 2.6 |
| 550 | | | | | | | | | | |

| Test examples | Yield of synthesized alcohol (%) | | | | | | | | | |
|---|---|---|---|---|---|---|---|---|---|---|
| | 11 | 12 | 13 | 14 | 15 | 16 | 17 | 18 | 19 | 20 |
| catalysts | HAP1 | HAP3 | HAP1 | HAP2 | HAP2 | HAP2 | HAP2 | HAP2 | HAP1 | HAP2 |
| combination of alcohol | C2 n-C4= | C2 b-C4 | C2 n-C5 | C2 n-C6 | C2 b-C6 | C2 n-C8 | C2 b-C8 | n-C3 n-C4 | b-C3 b-C4 | n-C3 n-C5 |
| reaction temperature (° C.) | | | | | | | | | | |
| 100 | 0.8 | 0.0 | 0.0 | 0.0 | 0.0 | 0.0 | 0.0 | 0.0 | 0.1 | 0.0 |
| 150 | 4.9 | 0.6 | 1.1 | 1.4 | 0.7 | 1.5 | 0.4 | 1.1 | 1.6 | 1.3 |
| 200 | 9.2 | 1.3 | 2.2 | 2.3 | 0.8 | 2.1 | 0.8 | 1.8 | 2.3 | 2.2 |
| 250 | 13.7 | 2.5 | 4.9 | 6.6 | 1.5 | 7.3 | 1.1 | 5.1 | 5.2 | 6.6 |
| 300 | 23.2 | 5.4 | 17.6 | 9.5 | 3.1 | 11.8 | 2.8 | 12.9 | 14.3 | 15.3 |
| 350 | 44.4 | 8.1 | 23.2 | 23.4 | 5.6 | 23.4 | 5.1 | 13.6 | 26.4 | 24.1 |
| 400 | 30.4 | 5.7 | 41.5 | 55.3 | 9.9 | 41.5 | 8.2 | 23.1 | 13.2 | 42.6 |
| 450 | 9.5 | 2.3 | 34.0 | 39.3 | 7.7 | 38.8 | 9.4 | 26.7 | 3.6 | 32.7 |
| 500 | 2.7 | 0.7 | 5.4 | 3.1 | 1.4 | 2.3 | 1.9 | 6.3 | 1.2 | 5.8 |
| 550 | | | | | | | | | | |

| Comparative examples | 1 | 2 | 3 | 4-1 | 4-2 | 4-3 | 4-4 | 6 |
|---|---|---|---|---|---|---|---|---|
| catalysts | MgO | MgO | MgO | MgO | CaF$_2$ | CaSiO$_3$ | ZrO$_2$ | MgO |
| combination of alcohol | C1 C2 | C1 n-C3 | C1 n-C5 | C2 n-C3 | C2 n-C3 | C2 n-C3 | C2 n-C3 | C2:n-C3 = 1:4 |
| reaction temperature (° C.) | | | | | | | | |
| 100 | 0.0 | 0.0 | 0.0 | 0.0 | 0.0 | 0.0 | 0.0 | 0.0 |
| 150 | 0.0 | 0.0 | 0.1 | 0.0 | 0.0 | 0.0 | 0.0 | 0.0 |
| 200 | 0.0 | 0.0 | 0.2 | 0.0 | 0.0 | 0.0 | 0.0 | 0.0 |
| 250 | 0.1 | 0.1 | 0.5 | 0.1 | 0.0 | 0.0 | 0.0 | 0.1 |
| 300 | 0.6 | 1.2 | 2.4 | 0.6 | 0.0 | 0.0 | 0.1 | 0.3 |
| 350 | 3.1 | 8.2 | 9.3 | 3.3 | 1.0 | 0.3 | 4.0 | 2.0 |
| 400 | 8.2 | 16.7 | 16.4 | 9.8 | 2.4 | 1.1 | 5.0 | 7.6 |
| 450 | 17.2 | 24.9 | 26.8 | 14.7 | 1.2 | 2.3 | 0.7 | 14.5 |
| 500 | 13.2 | 22.8 | 23.2 | 16.1 | 2.5 | 3.5 | 0.3 | 17.2 |
| 550 | | | | | | | | |

TABLE 3-continued

| | Comparative examples | 7 | 10-1 | 10-2 | 11 | 12 | 16 | 19 |
|---|---|---|---|---|---|---|---|---|
| | catalysts | MgO | MgO | CaF$_2$ | MgO | MgO | CaSiO$_3$ | MgO |
| | combination of alcohol | C2:n-C3 = 4:1 | C2 n-C4 | C2 n-C4 | C2 n-C4⁻ | C2 b-C4 | C2 n-C8 | b-C3 b-C4 |
| | reaction temperature (° C.) | | | | | | | |
| | 100 | 0.0 | 0.0 | 0.0 | 0.2 | 0.0 | 0.0 | 0.0 |
| | 150 | 0.0 | 0.0 | 0.0 | 0.7 | 0.0 | 0.0 | 0.0 |
| | 200 | 0.0 | 0.0 | 0.0 | 0.8 | 0.0 | 0.0 | 0.0 |
| | 250 | 0.1 | 0.1 | 0.0 | 0.9 | 0.1 | 0.0 | 0.0 |
| | 300 | 0.8 | 0.4 | 0.0 | 3.7 | 0.3 | 0.0 | 0.6 |
| | 350 | 4.7 | 2.0 | 0.1 | 12.8 | 1.3 | 0.4 | 1.8 |
| | 400 | 11.5 | 4.1 | 0.7 | 16.4 | 2.8 | 1.6 | 3.6 |
| | 450 | 15.7 | 7.4 | 0.6 | 14.9 | 3.8 | 2.8 | 3.5 |
| | 500 | 15.8 | 4.3 | 1.2 | 4.6 | 2.6 | 3.9 | 3.1 |
| | 550 | | | | | | | |

Linear Alcohol

Yield of linear alcohol in various combinations of raw material alcohol is shown in Table 4. Yield of linear alcohol in Table 4 shows the yield of linear alcohol synthesized directly from 2 kinds of raw material alcohol. For example, when methanol (C1) and ethanol (C2) are used as raw materials, yield of 1-propanol is shown. When ethanol (C2) and 1-propanol (C3) are used as raw materials, yield of 1-pentanol (C5) is shown.

TABLE 4

| | Yield of linear alcohol (%) | | | | | | | | | |
|---|---|---|---|---|---|---|---|---|---|---|
| Test examples | 1 | 2 | 3 | 4 | 5 | 6 | 7 | 8 | 9 | 10 |
| catalysts | HAP1 | HAP2 | HAP1 | HAP2 | HAP1 | HAP1 | HAP1 | HAP1 | HAP3 | HAP2 |
| combination of alcohol | C1 C2 | C1 n-C3 | C1 n-C5 | C2 n-C3 | C2:n-C3 = 1:9 | C2:n-C3 = 1:4 | C2:n-C3 = 4:1 | C2:n-C3 = 9:1 | C2 b-C3 | C2 n-C4 |
| reaction temperature (° C.) | | | | | | | | | | |
| 100 | 0.0 | 0.0 | 0.0 | 0.0 | 0.0 | 0.0 | 0.0 | 0.0 | 0.0 | 0.0 |
| 150 | 0.6 | 0.0 | 0.0 | 0.8 | 0.4 | 0.8 | 0.6 | 0.3 | 0.0 | 0.7 |
| 200 | 0.9 | 0.0 | 0.0 | 1.1 | 0.8 | 1.2 | 0.7 | 0.4 | 0.0 | 1.1 |
| 250 | 1.9 | 0.0 | 0.0 | 1.4 | 1.5 | 2.3 | 1.8 | 0.9 | 0.0 | 1.8 |
| 300 | 4.2 | 0.0 | 0.0 | 2.5 | 1.8 | 3.2 | 2.8 | 1.2 | 0.0 | 2.2 |
| 350 | 5.7 | 0.0 | 0.0 | 5.2 | 2.1 | 4.6 | 3.1 | 1.8 | 0.0 | 4.4 |
| 400 | 8.6 | 0.0 | 0.0 | 8.4 | 3.6 | 7.8 | 5.5 | 3.1 | 0.0 | 6.8 |
| 450 | 2.4 | 0.0 | 0.0 | 6.2 | 0.9 | 4.2 | 3.5 | 1.3 | 0.0 | 4.5 |
| 500 | 0.3 | 0.0 | 0.0 | 1.0 | 0.0 | 1.4 | 0.9 | 0.1 | 0.0 | 0.3 |
| 550 | | | | | | | | | | |

| | Yield of linear alcohol (%) | | | | | | | | | |
|---|---|---|---|---|---|---|---|---|---|---|
| Test examples | 11 | 12 | 13 | 14 | 15 | 16 | 17 | 18 | 19 | 20 |
| catalysts | HAP1 | HAP3 | HAP1 | HAP2 | HAP2 | HAP2 | HAP2 | HAP2 | HAP1 | HAP2 |
| combination of alcohol | C2 n-C4⁻ | C2 b-C4 | C2 n-C5 | C2 n-C6 | C2 b-C6 | C2 n-C8 | C2 b-C8 | n-C3 n-C4 | b-C3 b-C4 | n-C3 n-C5 |
| reaction temperature (° C.) | | | | | | | | | | |
| 100 | 0.0 | 0.0 | 0.0 | 0.0 | 0.0 | 0.0 | 0.0 | 0.0 | 0.0 | 0.0 |
| 150 | 0.2 | 0.0 | 0.9 | 1.2 | 0.0 | 1.4 | 0.0 | 0.0 | 0.0 | 0.0 |
| 200 | 0.3 | 0.0 | 1.5 | 1.7 | 0.0 | 1.5 | 0.0 | 0.0 | 0.0 | 0.0 |
| 250 | 0.5 | 0.0 | 2.3 | 3.1 | 0.0 | 3.3 | 0.0 | 0.0 | 0.0 | 0.0 |
| 300 | 1.6 | 0.0 | 5.7 | 3.8 | 0.0 | 3.7 | 0.0 | 0.0 | 0.0 | 0.0 |
| 350 | 2.2 | 0.0 | 6.7 | 6.2 | 0.0 | 4.9 | 0.0 | 0.0 | 0.0 | 0.0 |
| 400 | 1.8 | 0.0 | 8.3 | 11.6 | 0.0 | 6.3 | 0.0 | 0.0 | 0.0 | 0.0 |
| 450 | 1.2 | 0.0 | 2.5 | 7.3 | 0.0 | 6.7 | 0.0 | 0.0 | 0.0 | 0.0 |
| 500 | 0.4 | 0.0 | 0.7 | 0.1 | 0.0 | 0.0 | 0.0 | 0.0 | 0.0 | 0.0 |
| 550 | | | | | | | | | | |

TABLE 4-continued

| Comparative examples | 1 | 2 | 3 | 4-1 | 4-2 | 4-3 | 4-4 | 6 |
|---|---|---|---|---|---|---|---|---|
| catalysts | MgO | MgO | MgO | MgO | CaF$_2$ | CaSiO$_3$ | ZrO$_2$ | MgO |
| combination of alcohol | C1 C2 | C1 n-C3 | C1 n-C5 | C2 n-C3 | C2 n-C3 | C2 n-C3 | C2 n-C3 | C2:n-C3 = 1:4 |
| reaction temperature (° C.) | | | | | | | | |
| 100 | 0.0 | 0.0 | 0.0 | 0.0 | 0.0 | 0.0 | 0.0 | 0.0 |
| 150 | 0.0 | 0.0 | 0.0 | 0.0 | 0.0 | 0.0 | 0.0 | 0.0 |
| 200 | 0.0 | 0.0 | 0.0 | 0.0 | 0.0 | 0.0 | 0.0 | 0.0 |
| 250 | 0.1 | 0.0 | 0.0 | 0.0 | 0.0 | 0.0 | 0.0 | 0.0 |
| 300 | 0.7 | 0.0 | 0.0 | 0.2 | 0.0 | 0.0 | 0.0 | 0.1 |
| 350 | 2.7 | 0.0 | 0.0 | 0.9 | 0.6 | 0.1 | 0.9 | 0.4 |
| 400 | 4.2 | 0.0 | 0.0 | 2.1 | 1.2 | 0.6 | 0.8 | 1.4 |
| 450 | 3.6 | 0.0 | 0.0 | 2.5 | 0.5 | 1.1 | 0.4 | 1.9 |
| 500 | 2.3 | 0.0 | 0.0 | 1.8 | 1.1 | 1.6 | 0.0 | 1.5 |
| 550 | | | | | | | | |

| Comparative examples | 7 | 10-1 | 10-2 | 11 | 12 | 16 | 19 |
|---|---|---|---|---|---|---|---|
| catalysts | MgO | MgO | CaF$_2$ | MgO | MgO | CaSiO$_3$ | MgO |
| combination of alcohol | C2:n-C3 = 4:1 | C2 n-C4 | C2 n-C4 | C2 n-C4⁻ | C2 b-C4 | C2 n-C8 | b-C3 b-C4 |
| reaction temperature (° C.) | | | | | | | |
| 100 | 0.0 | 0.0 | 0.0 | 0.0 | 0.0 | 0.0 | 0.0 |
| 150 | 0.0 | 0.0 | 0.0 | 0.0 | 0.0 | 0.0 | 0.0 |
| 200 | 0.0 | 0.0 | 0.0 | 0.0 | 0.0 | 0.0 | 0.0 |
| 250 | 0.0 | 0.1 | 0.0 | 0.1 | 0.0 | 0.0 | 0.0 |
| 300 | 0.1 | 0.3 | 0.0 | 0.3 | 0.0 | 0.0 | 0.0 |
| 350 | 0.8 | 1.0 | 0.1 | 0.4 | 0.0 | 0.1 | 0.0 |
| 400 | 1.7 | 1.7 | 0.6 | 0.3 | 0.0 | 0.3 | 0.0 |
| 450 | 1.8 | 2.6 | 0.5 | 0.2 | 0.0 | 0.5 | 0.0 |
| 500 | 1.6 | 1.2 | 1.1 | 0.1 | 0.0 | 0.7 | 0.0 |
| 550 | | | | | | | |

As it is clear from Tables 1 and 2, according to the synthesizing method of the present invention, organic compounds useful as a chemical industry raw material can be synthesized in good yield. Further, as it is clear from Tables 3 and 4, when ethanol and linear alcohol other than ethanol are used, linear alcohol is synthesized in good yield. When methanol and alcohol having 3 or more carbon atoms are used, branched-chain alcohol is synthesized in good yield.

Example 1-2

Ethanol and 1-propanol were used as raw material alcohols, and by changing the mixing ratio, reaction was conducted similarly as Example 1-1. Yield of alcohol against the reaction temperature is shown in FIGS. 1-3.

As it is clear from FIGS. 1-3, kinds of alcohol produced vary depending on the mixing ratio (molar ratio). When the mixing ratio is 1:1, 1-pentanol which is a linear alcohol is synthesized the most. Therefore, when synthesizing linear alcohol having odd number of carbon atoms, such as 1-pentanol, when the converting ratio of raw material alcohol is almost equal, it is preferred that the mixing ratio is about 1:1.

Example 2

Second Synthesizing Method

Catalysts: The same catalysts as Example 1 were used.
Estimation of Catalyst Properties
Reaction was conducted similarly as Example 1, except for using 1 kind of alcohol having 3 or more carbon atoms as raw material alcohol. For each test, yield of organic compounds of C2 or more, organic compounds of C4 or more, alcohol (linear and branched-chain), and linear alcohol were measured. The results are shown in Tables 5-7. Linear alcohol was not produced in any of the Examples or Comparative Examples.

Organic Compounds Having 2 or More Carbon Atoms (C2+)
Yield of organic compounds of C2 or more for each raw material alcohol is shown in Table 5.

TABLE 5

| | Yield of C2+ organic compounds (%) | | | | |
|---|---|---|---|---|---|
| Test examples | 21 | 22 | 23 | 24 | 25 |
| catalysts | HAP2 | HAP2 | HAP2 | HAP1 | HAP2 |
| combination of alcohol | n-C3 | b-C3 | n-C4 | n-C4= | b-C4 |
| reaction temperature (° C.) | | | | | |
| 100 | 0.1 | 0.1 | 0.2 | 3.8 | 0.1 |
| 150 | 1.5 | 1.8 | 1.5 | 5.9 | 1.6 |
| 200 | 2.7 | 3.1 | 2.3 | 10.5 | 2.8 |
| 250 | 4.2 | 9.9 | 3.8 | 12.8 | 5.6 |
| 300 | 22.5 | 33.4 | 8.0 | 23.7 | 17.3 |
| 350 | 43.2 | 94.0 | 14.5 | 45.8 | 66.7 |
| 400 | 84.6 | 99.9 | 35.8 | 99.6 | 96.8 |
| 450 | 99.7 | 99.7 | 88.1 | 99.9 | 99.2 |
| 500 | 99.5 | 99.5 | 96.8 | 99.9 | 99.8 |
| 550 | | | | | |
| Comparative examples | 21 | 22 | 23 | 24 | 25 |
| catalysts | MgO | CaF$_2$ | ZrO$_2$ | MgO | CaSiO$_3$ |
| combination of alcohol | n-C3 | b-C3 | n-C4 | n-C4= | b-C4 |
| reaction temperature (° C.) | | | | | |
| 100 | 0.0 | 0.0 | 0.0 | 1.3 | 0.1 |
| 150 | 0.1 | 0.2 | 0.1 | 2.3 | 0.2 |
| 200 | 0.2 | 0.2 | 0.1 | 2.7 | 0.2 |
| 250 | 0.3 | 0.3 | 0.2 | 3.5 | 0.2 |
| 300 | 2.1 | 1.5 | 5.6 | 4.2 | 0.8 |
| 350 | 8.5 | 6.8 | 9.3 | 6.7 | 1.8 |
| 400 | 24.9 | 12.0 | 25.2 | 26.6 | 5.5 |
| 450 | 43.6 | 17.1 | 51.6 | 48.5 | 19.8 |
| 500 | 72.1 | 23.7 | 67.7 | 76.1 | 55.7 |
| 550 | | | | | |

Organic Compounds Having 4 or More Carbon Atoms (C4+)

Yield of organic compounds of C4 or more for each raw material alcohol is shown in Table 6.

TABLE 6

| | Yield of C4+ organic compounds (%) | | | | |
|---|---|---|---|---|---|
| Test examples | 21 | 22 | 23 | 24 | 25 |
| catalysts | HAP2 | HAP2 | HAP2 | HAP1 | HAP2 |
| combination of alcohol | n-C3 | b-C3 | n-C4 | n-C4= | b-C4 |
| reaction temperature (° C.) | | | | | |
| 100 | 0.1 | 0.1 | 0.2 | 3.6 | 0.1 |
| 150 | 1.4 | 1.2 | 1.4 | 5.8 | 1.6 |
| 200 | 2.6 | 2.3 | 2.2 | 10.3 | 2.7 |
| 250 | 4.0 | 6.2 | 3.7 | 12.5 | 5.5 |
| 300 | 21.8 | 23.6 | 7.9 | 23.3 | 17.1 |
| 350 | 38.8 | 63.7 | 14.4 | 45.2 | 66.6 |
| 400 | 65.2 | 37.9 | 35.7 | 98.3 | 96.7 |
| 450 | 61.2 | 22.3 | 87.4 | 98.5 | 99.0 |
| 500 | 55.5 | 17.2 | 94.6 | 97.7 | 99.2 |
| 550 | | | | | |
| Comparative examples | 21 | 22 | 23 | 24 | 25 |
| catalysts | MgO | CaF$_2$ | ZrO$_2$ | MgO | CaSiO$_3$ |
| combination of alcohol | n-C3 | b-C3 | n-C4 | n-C4= | b-C4 |
| reaction temperature (° C.) | | | | | |
| 100 | 0.0 | 0.0 | 0.0 | 1.2 | 0.0 |
| 150 | 0.1 | 0.1 | 0.1 | 2.2 | 0.1 |
| 200 | 0.1 | 0.1 | 0.1 | 2.5 | 0.1 |
| 250 | 0.2 | 0.2 | 0.2 | 3.1 | 0.2 |
| 300 | 1.1 | 0.7 | 5.5 | 3.6 | 0.7 |
| 350 | 6.3 | 4.2 | 9.1 | 6.2 | 1.6 |
| 400 | 17.4 | 5.4 | 24.6 | 25.3 | 5.3 |
| 450 | 27.6 | 8.6 | 57.7 | 46.1 | 18.3 |
| 500 | 43.7 | 11.4 | 64.2 | 73.8 | 52.6 |
| 550 | | | | | |

Alcohol (Linear and Branched-chain)

Yield of alcohol (linear and branched-chain) for each raw material alcohol is shown in Table 7.

TABLE 7

| | Yield of total synthesized alcohol (%) | | | | |
|---|---|---|---|---|---|
| Test examples | 21 | 22 | 23 | 24 | 25 |
| catalysts | HAP2 | HAP2 | HAP2 | HAP1 | HAP2 |
| combination of alcohol | n-C3 | b-C3 | n-C4 | n-C4= | b-C4 |
| reaction temperature (° C.) | | | | | |
| 100 | 0.0 | 0.0 | 0.0 | 1.1 | 0.0 |
| 150 | 1.2 | 1.0 | 1.2 | 2.3 | 0.8 |
| 200 | 2.2 | 1.7 | 1.8 | 2.8 | 1.2 |
| 250 | 3.5 | 3.2 | 2.7 | 3.2 | 2.3 |
| 300 | 18.4 | 5.6 | 3.8 | 4.6 | 3.5 |
| 350 | 28.2 | 2.5 | 5.3 | 15.6 | 6.0 |
| 400 | 14.9 | 0.8 | 8.8 | 27.9 | 2.0 |
| 450 | 2.4 | 0.2 | 17.4 | 8.6 | 0.7 |
| 500 | 1.8 | 0.0 | 18.0 | 3.0 | 0.0 |
| 550 | | | | | |
| Comparative examples | 21 | 22 | 23 | 24 | 25 |
| catalysts | MgO | CaF$_2$ | ZrO$_2$ | MgO | CaSiO$_3$ |
| combination of alcohol | n-C3 | b-C3 | n-C4 | n-C4= | b-C4 |
| reaction temperature (° C.) | | | | | |
| 100 | 0.0 | 0.0 | 0.0 | 0.2 | 0.0 |
| 150 | 0.0 | 0.0 | 0.0 | 0.3 | 0.0 |
| 200 | 0.1 | 0.0 | 0.1 | 0.2 | 0.0 |
| 250 | 0.2 | 0.0 | 0.2 | 0.2 | 0.0 |
| 300 | 0.7 | 0.2 | 0.7 | 0.3 | 0.1 |
| 350 | 3.2 | 0.6 | 0.9 | 1.5 | 0.2 |
| 400 | 7.7 | 0.7 | 1.7 | 2.6 | 0.3 |
| 450 | 11.4 | 1.2 | 3.9 | 4.4 | 0.5 |
| 500 | 14.6 | 1.5 | 5.5 | 1.3 | 0.7 |
| 550 | | | | | |

As it is clear from Tables 5-7, according to the synthesizing method of the present invention, organic compounds useful as a chemical industry raw material can be synthesized in good yield.

Example 3

Third Synthesizing Method

Catalyst: Hydrotalcite (Wako Pure Chemicals) was used as a catalyst.

Estimation of Catalyst Properties

Reaction was conducted similarly as Example 1, except for using hydrotalcite instead of hydroxyapatite. For each test, yield of organic compounds of C2 or more (C2+), organic compounds of C4 or more (C4+), alcohol (linear and branched-chain), and linear alcohol were measured. The results are shown in Table 8.

TABLE 8

| Test examples | 26 | 26 | 26 | 26 |
|---|---|---|---|---|
| Yield (%) catalysts combination of alcohol reaction temperature (° C.) | C2+ hydrotalcite C2 + n – C3 | C4+ hydrotalcite C2 + n – C3 | total alcohol hydrotalcite C2 + n – C3 | linear alcohol hydrotalcite C2 + n – C3 |
| 100 | 0.0 | 0.0 | 0.0 | 0.0 |
| 150 | 0.5 | 0.4 | 0.2 | 0.1 |
| 200 | 1.1 | 0.7 | 0.4 | 0.3 |
| 250 | 2.2 | 1.9 | 1.0 | 0.6 |
| 300 | 4.9 | 4.2 | 1.9 | 1.0 |
| 350 | 12.8 | 10.3 | 4.2 | 2.3 |
| 400 | 35.8 | 26.1 | 9.4 | 4.1 |
| 450 | 71.5 | 44.5 | 13.6 | 3.6 |
| 500 | 92.4 | 55.6 | 6.6 | 0.9 |
| 550 | | | | |
| Test examples | 27 | 27 | 27 | 27 |
| Yield (%) catalysts combination of alcohol reaction temperature (° C.) | C2+ hydrotalcite C2 + n – C4 | C4+ hydrotalcite C2 + n – C4 | total alcohol hydrotalcite C2 + n – C4 | linear alcohol hydrotalcite C2 + n – C4 |
| 100 | 0.0 | 0.0 | 0.0 | 0.0 |
| 150 | 1.4 | 1.2 | 0.8 | 0.5 |
| 200 | 2.0 | 1.7 | 1.1 | 0.6 |
| 250 | 3.4 | 3.1 | 1.3 | 0.8 |
| 300 | 5.1 | 4.8 | 1.6 | 1.0 |
| 350 | 14.7 | 13.6 | 3.1 | 2.2 |
| 400 | 31.6 | 27.5 | 5.2 | 3.4 |
| 450 | 69.6 | 58.5 | 6.4 | 2.6 |
| 500 | 88.7 | 76.8 | 2.7 | 0.8 |
| 550 | | | | |

As it is clear from Table 8, according to the synthesizing method of the present invention, organic compounds useful as a chemical industry raw material can be synthesized in good yield.

Example 4

Figure 4:
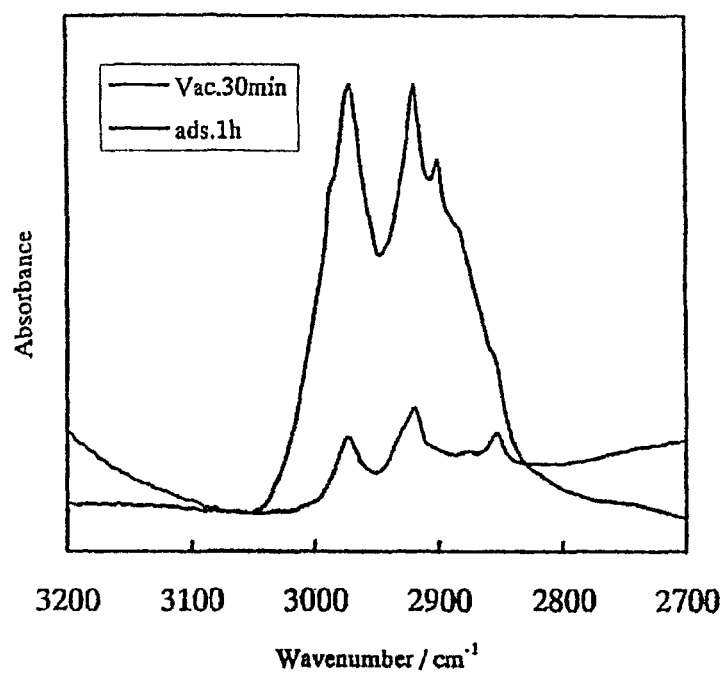
FIG. 4 is a figure showing the results of measurement of the inner state of the reactor by in situ FT-IR after 1 hour of exposure to ethanol/He mixed gas, followed by 30 min of emission.
Figure 5:
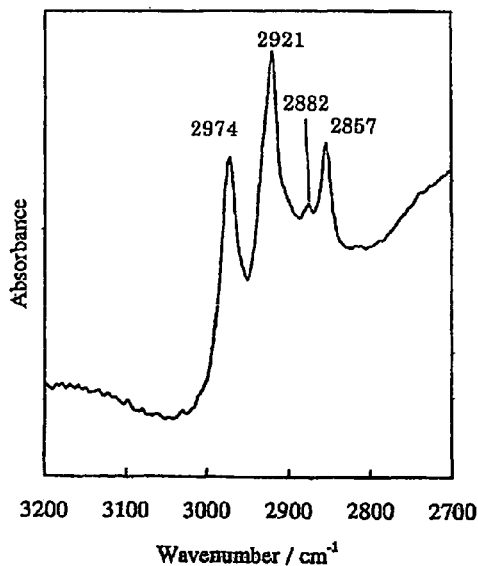
FIG. 5 is a figure showing the detailed results after 30 min of emission of FIG. 4.

Hydroxyapatite (HAP1) was exposed to about 7 vol % ethanol/He mixed gas for 1 hour in a reactor, and then emission was conducted. The inner state of the reactor after 1 hour of exposure to the mixed gas and the following 30 min of emission was measured by in situ FT-IR with a diffuse reflection method. The results are shown in FIGS. 4 and 5. In FIG. 4, the upper spectrum shows the state after 1 hour exposure to the mixed gas, and the lower spectrum shows the state after 30 min emission. As it is clear from FIGS. 4 and 5, it can be observed that ethanol is absorbed and supported by hydroxyapatite.

Example 5

Referring to the table of FIG. 6, hydroxyapatite (HAP1) catalyst is exposed to a mixed gas of ethanol and methanol at about 1:1 molar ratio and He, with the alcohols at about 20% of the mixture by volume. The mixed gas is exposed to the catalyst with a contact time of about 1.0 sec at various temperatures, as indicated in the depicted table. The selectivity of various specific products and product classes are determined, as also shown in the table.

Example 6

Referring to the table of FIG. 7, hydroxyapatite (HAP1) catalyst is exposed to a mixed gas of ethanol and methanol at about 1:20 molar ratio and He, with the alcohols at about 20% of the mixture by volume. The mixed gas is exposed to the catalyst with a contact time of about 1.0 sec at various temperatures, as indicated in the depicted table. The selectivity of various specific products and product classes are determined, as also shown in the table.

Example 7

Referring to the table of FIG. 8, hydroxyapatite (HAP1) catalyst is exposed to a mixed gas of ethanol and 1-propanol at about 4:1 molar ratio and He, with the alcohols at about 20% of the mixture by volume. The mixed gas is exposed to the catalyst with a contact time of about 1.0 sec at various temperatures, as indicated in the depicted table. The selectivity of various specific products and product classes are determined, as also shown in the table.

Example 8

Referring to the table of FIG. 9, hydroxyapatite (HAP1) catalyst is exposed to a mixed gas of ethanol and 1-propanol at about 1:1 molar ratio and He, with the alcohols at about 20% of the mixture by volume. The mixed gas is exposed to the catalyst with a contact time of about 1.0 sec at various temperatures, as indicated in the depicted table. The selectivity of various specific products and product classes are determined, as also shown in the table.

Example 9

Referring to the table of FIG. 10, hydroxyapatite (HAP1) catalyst is exposed to a mixed gas of ethanol and 1-propanol at about 1:4 molar ratio and He, with the alcohols at about 20% of the mixture by volume. The mixed gas is exposed to the catalyst with a contact time of about 1.0 sec at various temperatures, as indicated in the depicted table. The selectivity of various specific products and product classes are determined, as also shown in the table.

Example 10

Referring to the table of FIG. 11, hydroxyapatite (HAP1) catalyst is exposed to a mixed gas of ethanol, methanol and 1-propanol at about 1:5:1 molar ratio and He, with the alcohols at about 20% of the mixture by volume. The mixed gas is exposed to the catalyst with a contact time of about 1.0 sec at various temperatures, as indicated in the depicted table. The selectivity of various specific products and product classes are determined, as also shown in the table.

Example 11

Referring to the table of FIG. 12, MgO catalyst is exposed to a mixed gas of ethanol, methanol and 1-propanol at about 1:5:1 molar ratio and He, with the alcohols at about 20% of the mixture by volume. The mixed gas is exposed to the catalyst with a contact time of about 1.0 sec at various temperatures, as indicated in the depicted table. The selectivity of various specific products and product classes are determined, as also shown in the table.

Example 12

Referring to the table of FIG. 13, hydroxyapatite (HAP1) catalyst is exposed to a mixed gas of ethanol, methanol and 1-butanol at about 1:6:1 molar ratio and He, with the alcohols at about 20% of the mixture by volume. The mixed gas is exposed to the catalyst with a contact time of about 1.0 sec at various temperatures, as indicated in the depicted table. The selectivity of various specific products and product classes are determined, as also shown in the table.

Example 13

Referring to the table of FIG. 14, MgO catalyst is exposed to a mixed gas of ethanol, methanol and 1-butanol at about 1:6:1 molar ratio and He, with the alcohols at about 20% of the mixture by volume. The mixed gas is exposed to the catalyst with a contact time of about 1.0 sec at various temperatures, as indicated in the depicted table. The selectivity of various specific products and product classes are determined, as also shown in the table.

Example 14

Referring to the table of FIG. 15, the normal ratio percentage of C5 alcohol products are shown (i.e., the percentage of 1-pentanol product of the total saturated C5-alcohol products), in case beginning with the starting alcohols at a given ratio, and using the catalysts at the indicated temperatures, all as indicated on the table. Also shown is the percent-yield of the normal cross-Guerbet alcohols, which refers to the alcohols that are the product between the two different alcohol species (e.g., ethanol and propanol) rather than between two molecules of the same species.

Example 15

Referring to FIGS. 16A and 16B, the graphs show the distribution of products resulting from a reaction of two alcohols (ethanol and 1-propanol at about a 1:1 molar ratio) and a reaction of three alcohols (ethanol, methanol and 1-propanol at about a 1:5:1 respective molar ratio). Both reactions are performed at about 400° C. over hydroxyapatite, resulting in a conversion rate of the ethanol of about 50%. The graph depicted in FIG. 16A shows the distribution of all products from each reaction as a distribution based on the number of carbon atoms in the product. The graph depicted in FIG. 16B shows the distribution of alcohol products from each reaction as a distribution based on the number of carbon atoms in the alcohol.

Referring to FIGS. 17A and 17B, the graphs show the distribution of products resulting from a reaction of two alcohols (ethanol and 1-propanol at about a 1:1 molar ratio) and a reaction of three alcohols (ethanol, methanol and 1-propanol at about a 1:5:1 respective molar ratio). Both reactions are performed at about 500° C. over hydroxyapatite, resulting in a conversion rate of the ethanol of about 100%. The graph depicted in FIG. 17A shows the distribution of all products from each reaction as a distribution based on the number of carbon atoms in the product. The graph depicted in FIG. 17B shows the distribution of aldehyde and olefin products from each reaction as a distribution based on the number of carbon atoms in the aldehyde or olefin.

Example 16

Referring to FIGS. 18A and 18B, the graphs show the distribution of products resulting from a reaction of two alcohols (ethanol and 1-butanol at about a 1:1 molar ratio at about 400° C.) and a reaction of three alcohols (ethanol, methanol and 1-butanol at about a 1:6:1 respective molar ratio at about 350° C.). Both reactions are performed over hydroxyapatite, resulting in a conversion rate of the ethanol of about 50%. The graph depicted in FIG. 18A shows the distribution of all products from each reaction as a distribution based on the number of carbon atoms in the product. The graph depicted in FIG. 18B shows the distribution of alcohol products from each reaction as a distribution based on the number of carbon atoms in the alcohol.

Referring to FIGS. 19A and 19B, the graphs show the distribution of products resulting from a reaction of two alcohols (ethanol and 1-butanol at about a 1:1 molar ratio) and a reaction of three alcohols (ethanol, methanol and 1-butanol at about a 1:6:1 respective molar ratio). Both reactions are performed at about 500° C. over hydroxyapatite, resulting in a conversion rate of the ethanol of about 100%. The graph depicted in FIG. 19A shows the distribution of all products from each reaction as a distribution based on the number of carbon atoms in the product. The graph depicted in FIG. 19B shows the distribution of aldehyde and olefin products from each reaction as a distribution based on the number of carbon atoms in the aldehyde or olefin.

What is claimed is:

1. A method for synthesizing an alcohol having three or more carbon atoms comprising allowing a mixture of two or more kinds of starting alcohols to contact a catalyst comprising a calcium phosphate compound, wherein one of the two or more kinds of the starting alcohols is ethanol, and wherein the initial molar percentage of each of ethanol and a second starting alcohol is at least 5% of the total moles of the starting alcohols.

2. The method according to claim 1, wherein the calcium phosphate compound is hydroxyapatite.

3. The method according to claim 2, wherein the catalyst does not support a metal catalyst or metal ion catalyst.

4. The method according to claim 1 or 2, wherein the mixture of starting alcohols comprises ethanol and a linear alcohol other than ethanol to synthesize linear alcohol having three or more carbon atoms.

5. The method according to claim 4, wherein the linear alcohol is methanol, 1-propanol, 1-butanol, 1-pentanol, 1-hexanol, 1-heptanol, 1-octanol, or an unsaturated alcohol thereof.

6. The method according to claim 5, wherein the linear alcohol is 1-propanol.

7. The method according to claim 5, wherein the linear alcohol is 1-butanol.

8. The method according to claim 4, wherein the yield of the synthesized linear alcohol is 3C-mol % or more.

9. A method for synthesizing a branched alcohol comprising allowing a mixture of two or more kinds of starting alcohols to contact a catalyst comprising a calcium phosphate compound, wherein the mixture of starting alcohols comprises methanol and an alcohol having three or more carbon atoms.

10. The method according to claim 9, wherein the alcohol having three or more carbon atoms is a linear alcohol.

11. The method according to claim 10, wherein the linear alcohol is 1-propanol, 1-butanol, 1-pentanol, 1-hexanol, 1-heptanol, 1-octanol, or an unsaturated alcohol thereof.

12. A method for synthesizing an alcohol having six or more carbon atoms, comprising allowing one kind of starting alcohol having three or more carbon atoms to contact a catalyst comprising a calcium phosphate compound.

13. The method according to claim 12, wherein the calcium phosphate compound is hydroxyapatite.

14. The method according to claim 12 or 13, wherein the one kind of alcohol is propanol, butanol, pentanol, hexanol, heptanol, octanol, or unsaturated alcohols thereof.

15. The method according to any one of claims 1, 9 and 12, wherein the reaction is conducted at about 200° C. to about 600° C.

16. The method according to claim 12, wherein the calcium phosphate compound does not support a metal catalyst or metal ion catalyst.

\* \* \* \* \*